(12) United States Patent
Gelfand et al.

(10) Patent No.: US 7,160,681 B2
(45) Date of Patent: Jan. 9, 2007

(54) METHOD FOR REGULATING CELL GROWTH AND ASSAYS RELATED THERETO

(75) Inventors: Erwin W. Gelfand, Englewood, CO (US); Joseph J. Lucas, Evergreen, CO (US)

(73) Assignee: National Jewish Medical and Research Center, Denver, CO (US)

( * ) Notice: Subject to any disclaimer, the term of this patent is extended or adjusted under 35 U.S.C. 154(b) by 418 days.

(21) Appl. No.: 10/154,272

(22) Filed: May 22, 2002

(65) Prior Publication Data

US 2003/0039998 A1    Feb. 27, 2003

Related U.S. Application Data

(63) Continuation of application No. 09/672,864, filed on Sep. 28, 2000, now abandoned.

(60) Provisional application No. 60/156,906, filed on Sep. 30, 1999.

(51) Int. Cl.
   *C12Q 1/68* (2006.01)
(52) U.S. Cl. .......................................... 435/6; 435/7.23
(58) Field of Classification Search ............... 435/7.23, 435/7.21, 7.1, 6; 530/350, 388.8; 436/501, 436/65
See application file for complete search history.

(56) References Cited

U.S. PATENT DOCUMENTS

| | | | |
|---|---|---|---|
| 5,691,147 A | 11/1997 | Draetta et al. | 435/7.1 |
| 5,733,920 A | 3/1998 | Mansuri et al. | 514/337 |
| 5,856,094 A | 1/1999 | Sidransky et al. | 435/6 |
| 6,001,868 A | 12/1999 | Firestone et al. | 514/415 |
| 6,033,847 A | 3/2000 | Sherr et al. | 435/6 |
| 6,043,030 A | 3/2000 | Beach et al. | 435/6 |
| 6,048,693 A | 4/2000 | Bitter | 435/6 |

OTHER PUBLICATIONS

Timmermann et al. Cell Growth Differ. Apr. 1997; 8 (4): 361-370.*
Costello et al. Cancer Res. Apr. 1, 1997; 57 (7): 1250-1254.*
Lam et al. Br. J. Neurosurg. Feb. 2000; 14 (1): 28-32.*
Tang et al. Melanoma Res. Apr. 1999; 9 (2): 148-154.*
Sahl et al. Anticancer Res. Jan.-Feb. 1999; 19 (1B): 741-748.*
Brito-Babapulle et al. Hematologica. Apr. 2002; 87 (4): 357-362.*
Wolowiec et al. Br. J. Hematol. 1996; 95: 518-523.*
Timms et al. Oncogene. Sep. 26, 2002; 21 (43): 6573-6586.*
Taylor-Papadimitriou et al. J. Cell Sci. Nov. 1989; 94 (Pt 3): 403-413.*
Petersen et al. Proc. Natl. Acad. Sci. USA. Oct. 1992; 89: 9064-9068.*
Brandi et al. Cancer Res. Jul. 15, 2003; 63: 4028-4036.*
Hynes (Semin. Cancer Biol. Feb. 1993; 4 (1): 19-26).*
Koskinen et al. (Semin. Cancer Biol. Feb. 1993; 4 (1): 3-12).*
Chinni, et al., *Oncogene*, 20(23):2927-2936 (2001).
Covert et al., *J. Biol. Chem.*, 273(7):3838-3847 (1998).
Cram, et al., *J. Biol Chem*, 276(25):22332-22340 (2001).
Ellis et al., *EMBO J.*, 18(3):644-653 (1999).
Dauphinot, et al. *Oncogene*, 20(25):3258-3265. (abstract only Pub-Med database).
Lam, et al., *Br. J. Neurosurg.*, 14(1):28-32 (2000) (abstract only Pub-Med database).
Lucas et al., *J. Immunol.*, 154:6275-6284 (1995).
GenBank Accession No. 4502740 (Meyerson et al., *EMBO J.*, 11(8):2909-2917 (1992)).
Nagasawa et al., *J. Immunol.*, 158:5146-5154 (1997).
Nijjar et al., *Cancer Res.*, 59(20):5112-8 (1999) (Abstract).
Tang, et al., *Melanoma Res.*, 9(2):148-154 (1999) (abstract only Pub-Med database).

* cited by examiner

*Primary Examiner*—Stephen L. Rawlings
(74) *Attorney, Agent, or Firm*—Sheridan Ross PC

(57) ABSTRACT

Disclosed are methods for assessing tumor cell growth in a patient for the diagnosis, monitoring and/or staging of tumor development. The method include the identification of reduced cdk6 expression or biological activity as an indicator of increased cell growth in a cell sample. The methods further include the identification of compounds which regulate cdk6 and the use of such compounds in a method for the regulation of inappropriate cell growth.

13 Claims, 5 Drawing Sheets

METHOD FOR REGULATING CELL GROWTH AND ASSAYS RELATED THERETO

CROSS-REFERENCE TO RELATED APPLICATIONS

This application is a continuation of U.S. application Ser. No. 09/672,864, filed Sep. 28, 2000, now abandoned, which claims priority under 35 U.S.C. § 119(e) from U.S. Provisional Application Ser. No. 60/156,906, filed Sep. 30, 1999, and entitled "Differential Roles of cdk4 and cdk6 in Cell Growth." The entire disclosure of each of U.S. application Ser. No. 09/672,864 and U.S. Provisional Application Ser. No. 60/156,906 is incorporated herein by reference.

GOVERNMENT RIGHTS

This invention was made in part with government support under NIH Grant Nos. HL-36577 AI-42246, AI-36676 and AI-23764, all awarded by the National Institutes of Health. The government has certain rights to this invention.

FIELD OF THE INVENTION

The present invention relates to a method for assessing tumor cell growth, for identifying compounds that inhibit such tumor growth, and for using such compounds to inhibit cell growth.

BACKGROUND OF THE INVENTION

Passage through the animal cell cycle is regulated at least in part by the cyclin-dependent kinases, at least nine of which have been so far identified (Meyerson et al., *EMBO J.*, 11:2909–2917, 1992; Pines, *Semin. Cell Biol.*, 5:339–408,1994; Tassan et al., *Proc. Natl. Acad. Sci. USA*, 92:8871–8875, 1995; de Falco and Girdano, *J. Cell. Physiol.*, 177:501–506, 1998). The functions of three of them, cdk1 (cdc2), cdk2 and cdk4, have been delineated in most detail. In brief, cdk1 plays a role in regulating the G2 to M-phase transition (Lohka et al., *Proc. Natl. Acad. Sci. USA*, 85:3009–3013, 1988; Draetta et al., *Cell*, 56:829–838, 1989; Labbe et al., *EMBO J.*, 8:3053–3058, 1989; Nigg, *Curr. Opin. Cell Biol.*, 5:187–193, 1993); cdk2 is involved in S-phase entry and progression (Dulic et al., *Science*, 257:1958–1961, 1992; Koff et al., *Science*, 257:1689–1693, 1992; Ohtsubo and Roberts, *Science*, 259:1908–1912, 1993; Sherr, *Science*, 274:1672–1677, 1996); and cdk4, by inactivating the growth-suppressing functions of the Rb-protein, appears to permit passage through G1 phase (Matsushima et al., *Cell*, 71:323–334, 1992; Kato et al., *Genes & Develop.*, 7:331–342,1993; Sherr and Roberts, *Genes & Develop.*, 9:1149–1163, 1995; Weinberg, *Cell*, 81:323–330, 1995). Perhaps the most direct demonstration for the roles of cdk1 and cdk2 was derived from experiments using dominant-negative forms of the proteins, which were mutated in their ATP-binding sites but could still form complexes with appropriate cyclins. Expression of the dominant-negative forms of cdc2 or cdk2 blocked cells in the G2 and G1 phases of the cycle, respectively (van den Heuvel and Harlow, *Science*, 262:2050–2054, 1993). Though it is less direct, other evidence supports a role for cdk4 in G1-phase progression through regulation of Rb function. For example, over-expression of D-type cyclins, which activate cdk4, shortens G1-phase length (Quelle et al., *Genes & Develop.*, 7:1559–1571, 1993). It appears that certain cell lines which lack the Rb protein no longer require cyclin D-associated kinase activity for growth (Lukas et al., *Molec. Cell. Biol.*, 15:2600–2611, 1995). Also, it was shown that microinjection of active cyclin D1-cdk4 complexes into quiescent human diploid fibroblasts induced a portion of the cells to enter S-phase (Connell-Crowley et al., *Curr. Biol.*, 8:65–68, 1998).

More recently, the notion that cdk4 is essential for cell proliferation has been challenged by the finding that mice strains generated to be devoid of cdk4 are viable (Rane et al., *Nature Genetics*, 22:44–52, 1999; Tsutsui et al., *Molec. Cell. Biol.*, 19:7011–7019, 1999). However, such mice are small in size, infertile and prone to the development of diabetes associated with a degeneration of pancreatic islets. In light of many previous in vitro studies, it was surprising to find that cdk4-deficient embryonic fibroblasts derived from such mice appeared to proliferate normally in culture. However, when such cells were growth-arrested in culture and then stimulated to re-enter the cell cycle, their entry into S-phase was markedly delayed when compared to wild-type, cdk4-containing cells (Rane et al., *Nature Genetics*, 22:44–52, 1999; Tsutsui et al., *Molec. Cell. Biol.*, 19:7011–7019, 1999). Similar growth properties had in fact previously been observed in cells (derived from the U2OS line) having reduced cdk4 activity levels due to enforced expression of a dominant-negative form of cdk4 (Jiang et al., *Molec. Cell. Biol.*, 18:5284–5290, 1998). Like the cdk4-negative embryonic fibroblasts, the cell line showed a reduced entry into S-phase after release from growth arrest, but appeared otherwise normal in growth properties. Taken together, the latter studies suggest that cdk4 may not be essential for cell growth and that its functions may be more important in some cell types than in others. Alternatively, it is possible that the normal functions of cdk4 have been at least partially assumed by another kinase, such as cdk6, in the absence of cdk4. The severity of the effects of cdk4 absence on certain organs or cell types may be in part a reflection of the normal balance of cdk4 and cdk6 in the particular cell types. Such a partial assumption of function is not unprecedented. A notable example is observed in Lck-deficient mice, in which a related Src-family kinase, Fyn, appears to partially substitute for Lck. Mice deficient in both Fyn and Lck unmask the essential roles of the two kinases in T cell development and signaling (Appleby et al., *Cell*, 70:751–763, 1992; Molina et al., *Nature*, 357:161–164, 1992; Groves et al., *Cell*, 5:417–428, 1996).

Among the cdk family, cdk4 and cdk6 form a sub-group extremely homologous in structure. Then their entire primary structures are compared, nearly 70% homology is observed (Meyerson et al., *EMBO J.*, 11:2909–2917, 1992; Hanks, *Proc. Natl Acad. Sci. USA*, 84:388–392, 1987). Furthermore, the two proteins share numerous other similarities. Both are activated by binding to D-type cyclins (Bates et al., *Oncogene*, 9:71–79, 1994; Matsushime et al., *Molec. Cell. Biol.*, 14:2066–2076, 1994; Meyerson and Harlow, *Molec. Cell. Biol.*, 14:2077–2086, 1994; Lucas et al., *J. Immunol.*, 154:6275–6284, 1995). Unlike cdk1 and cdk2, neither will phosphorylate the histone H1 protein in vitro, but will utilize the Rb protein as a substrate (Matsushime et al., *Molec. Cell. Biol.*, 14:2066–2076, 1994; Meyerson and Harlow, *Molec. Cell. Biol.*, 14:2077–2086, 1994). Unlike cdk1 and cdk2, cdk4 and cdk6 lack a regulatory threonine residue in their ATP binding sites (Meyerson et al., *EMBO J.*, 11:2909–2917, 1992; Hanks, *Proc. Natl. Acad. Sci. USA*, 84:388–392, 1987; Morgan, *Nature*, 374:131–134, 1995). All animal cells yet examined contain both cdk4 and cdk6, but the ratio of the two proteins varies among cell types (Meyerson et al., *EMBO J,* 11:2909–2917, 1992). For example, T lymphocytes are an especially rich source of cdk6 activity (Meyerson and Harlow, *Molec. Cell. Biol.,* 14:2077–2086, 1994; Lucas et al., *J. Immunol.,* 154: 6275–6284, 1995), while, as shown below, fibroblast cells, such as the 3T3 line, have very high levels of cdk4. Because of their many similarities in structure and activity, it has been presumed, prior to the present invention, that cdk4 and cdk6 perform very similar functions in cells, with either cdk4 or cdk6 predominating in certain cell types and tissues. That cdk6 likely plays role(s) in G1 phase, like cdk4, has been suggested by analysis of lines with excess or deficient cdk6 activities due to expression of wild-type or dominant-negative forms of the kinase (Grossel et al., *J. Biol. Chem.,* 274:29960–29967, 1999; Ojala et al., *Cancer Res.,* 59:4984–4989, 1999). Enforced expression of wild-type cdk6, either alone (Grossel et al., *J. Biol. Chem.,* 274: 29960–29967, 1999) or together with cyclin D1 (Ojala et al., *Cancer Res.,* 59:4984–4989, 1999) appeared to shorten G1 phase length whereas the dominant-negative form delayed S-phase entry (Grossel et al., *J. Biol. Chem.,* 274:29960–29967, 1999). These studies were both performed with the U2OS cell line, which is defective in production of the p16$^{INK4a}$ cdk inhibitor (Koh et al., *Nature,* 375:506–510, 1995; Lukas et al., *Nature,* 375:503–506, 1995; Medema et al., *Proc. Natl. Acad. Sci. USA,* 92:6289–6293, 1995). Furthermore, the level of enhancement or abrogation of cdk6 in the transfected U2OS cells was not demonstrated in those studies.

From examinations of cdk4 and cdk6 activities in T lymphocytes, similarities in the regulation of the two activities emerged. When normal resting T cells were stimulated to enter the cell cycle, cdk4 and cdk6 activities were the first to be detected (Meyerson and Harlow, *Molec. Cell. Biol.,* 14:2077–2086, 1994; Lucas et al., *J. Immunol.,* 154:6275–6284, 1995; Lucas et al., *J. Cell. Physiol.,* 165: 406–416, 1995). Each kinase formed two different complexes, with cyclin D2-associated activities preceding by many hours the appearance of cyclin D3-associated activities (Meyerson and Harlow, *Molec. Cell. Biol.,* 14:2077–2086, 1994; Lucas et al., *J. Immunol.,* 154:6275–6284, 1995). Increases in cdk4, cdk6 and cyclin D2 protein levels and in both cdk4 and cdk6 kinase activities occurred very early in G1-phase, before synthesis of IL-2, the major T-cell "progression" factor and thus before IL-2/ IL-2 receptor interactions which are essential for progression through the restriction point and cell proliferation (Lucas et al., *J. Immunol.,* 154:6275–6284, 1995; Lucas et al., *J. Cell. Physiol.,* 165:406–416, 1995; Modiano et al., *J. Biol. Chem.* 269:32972–32978, 1994). However, differences in the properties of the two kinases also emerged. Thus, cdk6 protein was readily detected in resting T cells (Lucas et al., *J. Immunol.,* 154:6275–6284, 1995). Increases in the levels of this protein and its kinase activity preceded by at least two hours those of cdk4 (Lucas et al., *J. Immunol.,* 154:6275–6284, 1995; Lucas et al., *J. Cell. Physiol.,* 165: 406–416, 1995). It was further demonstrated by immunofluorescence microscopy that the resting population of T-cells contained cdk6 and that within minutes of T-cell activation it was translocated to the nucleus (Nagasawa et al., *J. Immunol.,* 158:5146–5154, 1997), suggesting a very early role for the protein in cell cycle entry or early G1-phase progression. The T-cell derived Jurkat cell line, like its normal counterpart, contains a high level of cdk6 protein. Cdk6 kinase activity can be detected in high amount in the normal proliferative state of the cell line. However, when the line is stimulated by agents which stimulate IL-2 production, such as a combination of anti-CD3 and anti-CD28 monoclonal antibodies, there is a dramatic and rapid (within 15 minutes) increase in cdk6 kinase activity and a translocation of cdk6 and cyclin D2 proteins to the cell nuclei (Nagasawa et al., *J. Immunol.,* 158:5146–5154, 1997). Taken together, the latter observations suggested that cdk6 is performing important functions very soon after cells are stimulated through receptors which initiate signal transduction pathways leading to cell growth and/or the production of growth factors involved in cell cycle progression.

It is therefore of interest to determine the effects of both cdk4 and cdk6 in various cell systems, especially since it appears likely that the functions of cdk4 and cdk6, and their relative importance, may differ in various cell types, as discussed further below.

Many different molecular defects have been observed in breast cancer cells. Although the outcome is malignant cell growth, no one defect or set of defects is seen in all breast tumors. However, as knowledge of signal transduction and cell cycle pathways has increased, it has become clear that these defective molecules are components of basic regulatory networks and that defects in any of a number of them can lead to the same or very similar phenotypes (Hunter, *Cell,* 88:333–346, 1997). Two key components of the fundamental cell-growth regulatory networks are the Rb and p53 proteins (Weinberg, *Cell,* 81:323–330,1995; Levine, *Cell,* 88:323–331,1997). Both are growth-suppressing molecules and defects in either protein or in proteins controlling their activities are seen in virtually all human tumors (Levine, *Cell,* 88:323–331, 1997; Hollstein et al., *Nucleic Acids Res.,* 22:3551–3555, 1994). Rb activity is regulated in part by the G1-phase cyclin-dependent kinases, such as cdk4, which are in turn regulated by CDKIs (cyclin-dependent kinase inhibitors of the Cip/Kip and Ink4 families), cyclin D-family members, and cdc25 phosphatases (Sherr, *Science,* 274:1672–1677, 1996; Morgan, *Nature,* 374:131–134, 1995). Overproduction of cyclin D1 has been observed in a relatively high portion of human breast tumor samples (Buckley, et al., *Oncogene,* 8:2127–2133, 1993; Gillett et al., *Cancer Res.,* 54:1812–1817, 1994; Sutherland et al., *Acta Oncologica,* 34:651–656, 1995; Weinstat-Saslow et al., *Nature Medicine,* 1:1257–1260,1995); decreased production of the CDKIs p16 (ink4a) orp27 (kip1) has been seen in others (Cairns et al., *Nature Genetics,* 11:210–212., 1995; Tan et al., *Cancer Res.,* 57:1259–1263, 1997); and dysregulatien of cdc25A has been seen in some tumor cell lines (Galaktionov et al., *Science,* 269:1575–1577, 1995). In turn, p53 regulates production of p21 (cip1), also an inhibitor of cdks (E1-Diery et al., *Cell,* 75:817–825, 1993; Sherr and Roberts, *Genes & Develop.,* 9:1149–1163, 1995), and Bax (Miyashita and Reed, *Cell,* 80:293–299, 1995), an inducer of programmed cell death. Production of mutant p53 has been seen in many breast tumors (Levine, *Cell,* 88:323–331, 1997; Hollstein et al., *Nucleic Acids Res.,* 22:3551–3555, 1994; Bartek et al., *Int. J. Cancer,* 46:839–844, 1990); decreased Bax production has also been observed in some (Krajewski et al., *Cancer Res.,* 55:4471–4478, 1995).

As noted above, cdk4 is a major regulator of Rb function (Sherr, *Science,* 274:1672–1677, 1996) and cellular alterations or mutations which interfere with its activity are likely candidates for oncogenic events. However, such defects may also interfere with cdk6 activity, which, as discussed above, is a kinase which is highly related to cdk4 in structure (Hanks, *Proc. Natl. Acad. Sci. USA,* 84:388–292,1987; Meyerson et al., *EMBO J.,* 11:2909–2917, 1992) and regulated by the same basic set of molecules, that is Cip/Kip and Ink4-family CDKIs, D-type cyclins, and cdc25 phosphatases (Morgan, *Nature,* 374: 131–134, 1995; Sherr and Roberts, *Genes & Develop.,* 9:1149–1163, 1995). Amplification of cdk6 DNA and increased cdk6 enzyme levels have been seen in some human gliomas and squamous cell carcinoma lines, respectively (Costello et al., *Cancer Res.,* 57:1250–1254, 1997; Timmermann et al., *Cell Growth Different.,* 8:361–371, 1997), but the possible clinical significance of these observations remains to be elucidated.

Therefore, there is a need to further elucidate the functions of cell cycle regulators such as cdk4 and cdk6 and to use such information to develop a better understanding of cell cycle events in tumor cells so that therapeutic strategies can be devised.

SUMMARY OF THE INVENTION

One embodiment of the present invention is a method for assessing tumor cell growth in a patient. The method includes the steps of: (a) detecting cdk6 expression or biological activity in a cell sample from a patient; and, (b) comparing the cdk6 expression or biological activity as detected in step (a) to a baseline level of cdk6 expression or biological activity established from a control sample. Detection of reduced cdk6 expression or reduced cdk6 biological activity as compared to the baseline level of cdk6 expression or biological activity, is an indicator of increased cell growth or potential therefor in the cell sample as compared to the control sample; and, detection of increased or substantially similar cdk6 expression or cdk6 biological activity as compared to the baseline level of cdk6 expression or biological activity, is an indicator of decreased cell growth or potential therefor in the cell sample as compared to the control sample.

In one aspect, the step (a) of detecting comprises detecting cdk6 mRNA transcription in the cell sample. Such a step of detecting can be achieved by a method including, but not limited to, polymerase chain reaction (PCR), reverse transcriptase-PCR (RT-PCR), in situ hybridization, Northern blot, sequence analysis and detection of a reporter gene. In another aspect, the step (a) of detecting comprises detecting cdk6 translation in the cell sample. Such a step can be achieved by a method including, but not limited to, immunoblot, enzyme-linked immunosorbant assay (ELISA), radioimmunoassay (RIA), immunoprecipitation, immunohistochemistry and immunofluorescence. In another aspect, the step (a) of detecting comprises detecting cdk6 biological activity in the cell sample. Such a method can be achieved by a method including, but not limited to a kinase method to detect cdk6 kinase activity.

In a one aspect, the cell sample is from mammary tissue in the patient. Preferably, the cell sample is from a mammary epithelial cell.

In one aspect, detection of a statistically significant change in cdk6 expression or biological activity in the cell sample as compared to the baseline level for the control sample, with a confidence of $p<0.05$, indicates a change in cell growth or potential therefor in the sample as compared to the control sample. In another aspect, detection of an at least about 30% change in cdk6 expression or biological activity in the cell sample as compared to the baseline level for the control sample, with a confidence of $p<0.05$, indicates a change in cell growth or potential therefor in the sample as compared to the control sample. In yet another aspect, detection of an at least about 50% change in cdk6 expression or biological activity in the cell sample as compared to the baseline level for the control sample, with a confidence of $p<0.05$, indicates a change in cell growth or potential therefor in the sample as compared to the control sample. In yet another aspect, detection of an at least about 1.5 fold change in cdk6 expression or biological activity in the cell sample as compared to the baseline level for the control sample, with a confidence of $p<0.05$, indicates a change in cell growth or potential therefor in the sample as compared to the control sample.

In one aspect, the cell sample is from a patient being diagnosed for cancer, the baseline level is from a negative-control sample, and detection of reduced cdk6 expression or reduced cdk6 biological activity as compared to the baseline level of cdk6 expression or biological activity is indicative of tumor cell growth or potential therefor in the cell sample. In this method, when the cdk6 expression or biological activity detected in step (a) is reduced as compared to the baseline level, the method further comprises the steps of (c) comparing the cdk expression or biological activity as detected in step (a) to levels of cdk6 expression or biological activity from a panel of tumor control samples, wherein each of the tumor control samples is correlated with a different stage of tumor development; and, (d) identifying a level of cdk6 expression of biological activity from one of the tumor control samples which is statistically significantly most similar to the level of cdk6 expression or biological activity detected in step (a), to diagnose a stage of tumor development in the patient. In a further embodiment, the sample is preferably from mammary tissue of the patient, and the panel of tumor control samples comprises one tumor control sample from each of a stage I, stage II, stage III, and stage IV, breast cell tumor.

In another aspect, the cell sample is from a patient who is known to have cancer, and the baseline level is from a previous tumor cell sample from the patient. In this aspect, the method further comprises a step (c) of modifying cancer treatment for the patient based on whether an increase or decrease in cell growth is indicated in step (b).

The baseline of the present method can be established by a method including, but not limited to: (1) establishing a baseline level of cdk6 expression or biological activity in an autologous control sample from the patient, wherein the autologous sample is from a same cell type, tissue type or bodily fluid type as the sample of step (a); (2) establishing a baseline level of cdk6 expression or biological activity from at least one previous detection of cdk6 expression or biological activity in a previous sample from the patient, wherein the previous sample was of a same cell type, tissue type or bodily fluid type as the sample of step (a); and, (3) establishing a baseline level of cdk6 expression or biological activity from an average of control samples of a same cell type, tissue type or bodily fluid type as the sample of step (a), the control samples having been obtained from a population of matched individuals. In one aspect, the baseline level of (2) is established from a sample previously diagnosed as being positive for tumor cell growth.

Yet another embodiment of the present invention relates to an assay kit for diagnosing tumor cell growth or a potential for tumor cell growth in a patient. The assay kit includes: (a) a means for detecting cdk6 expression or biological activity in a cell sample; and, (b) a means for detecting a control marker characteristic of a cell type in the cell sample. In one aspect, the means of (a) is selected from the group consisting of: a hybridization probe of at least about 8 nucleotides that hybridizes under stringent hybridization conditions to a nucleic acid molecule encoding cdk6 or a fragment thereof; an oligonucleotide primer for amplification of mRNA encoding cdk6 or a fragment thereof; and an antibody that selectively binds to cdk6. In one aspect, the means of (b) is selected from the group consisting of: a hybridization probe of at least about 8 nucleotides that hybridizes under stringent hybridization conditions to a nucleic acid molecule encoding the control marker or a fragment thereof; an oligonucleotide primer for amplification of mRNA encoding the control marker or a fragment thereof; and an antibody that selectively binds to the control marker. Preferably, the means of (a) and (b) are suitable for use in a method of detection selected from the group consisting of immunohistochemistry and immunofluorescence.

In a preferred embodiment, the cell sample is a breast tissue sample. In this aspect, the means of (b) can include, but is not limited to, an antibody that selectively binds to a cytokeratin. In a particularly preferred embodiment, the cytokeratin is selected from the group consisting of cytokeratin 14, cytokeratin 19 and vimentin.

Yet another embodiment of the present invention relates to a method to identify a compound useful for inhibition of cell growth. Such a method includes the steps of: (a) detecting an initial level of cdk6 expression or biological activity in a cell; (b) contacting the cell with a test compound; (c) detecting a level of cdk6 expression or biological activity in the cell after contact of the cell with the compound; and, (d) selecting a compound that increases the expression or biological activity of cdk6 in the cell as compared to the initial level as being useful for inhibition of cell growth. In one aspect, the method further includes a step of detecting whether the compound selected in (d) inhibits growth of the cell. In one aspect the cell is a tumor cell. In another aspect, the method further comprises a step of detecting whether the compound decreases p57KIP2 expression or biological activity in the cell. In yet another aspect, the method further includes steps of: (e) detecting a level of cdk4 expression in the cell prior to and after contact with the compound; and, (f) selecting a compound that does not substantially increase the expression or biological activity of cdk4 in the cell after contact with the compound as compared to prior to contact with the compound.

In one embodiment, the steps of detecting comprise detecting cdk6 mRNA transcription. Such methods have been described above. In another embodiment, the steps of detecting comprise detecting cdk6 translation. Such methods have also been described above. In another embodiment, the steps of detecting comprise detecting cdk6 kinase activity.

Yet another embodiment of the present invention relates to a method to regulate cell growth. Such a method includes the step of increasing cyclin dependent kinase 6 (cdk6) expression or biological activity in the cell to inhibit growth of the cell. In one aspect, such a method includes overexpressing cdk6 in the cell. In one aspect, such a method comprises translecting the cell with a recombinant nucleic acid molecule encoding cdk6 operatively linked to a transcription control sequence, wherein the recombinant cdk6 is expressed by the cell. Preferably, the recombinant nucleic acid molecule comprises a recombinant viral vector. In another aspect, the method comprises increasing the activity of a cdk6 gene promoter in the cell such that expression of endogenous cdk6 in the cell is increased. In another aspect, the method comprises increasing enzymatic activity of cdk6 in the cell. In yet another embodiment, the method comprises contacting the cell with a compound which increases cdk6 expression or biological activity. In another embodiment, the method comprises decreasing the expression or biological activity of p57KIP2 in the cell. Preferably, cdk6 expression or biological activity is increased in a targeted cell. In one embodiment, the targeted cell is a tumor cell. In yet another embodiment, the method further comprises inhibiting the expression or biological activity of cdk4.

DETAILED DESCRIPTION OF THE INVENTION

Figure 1:
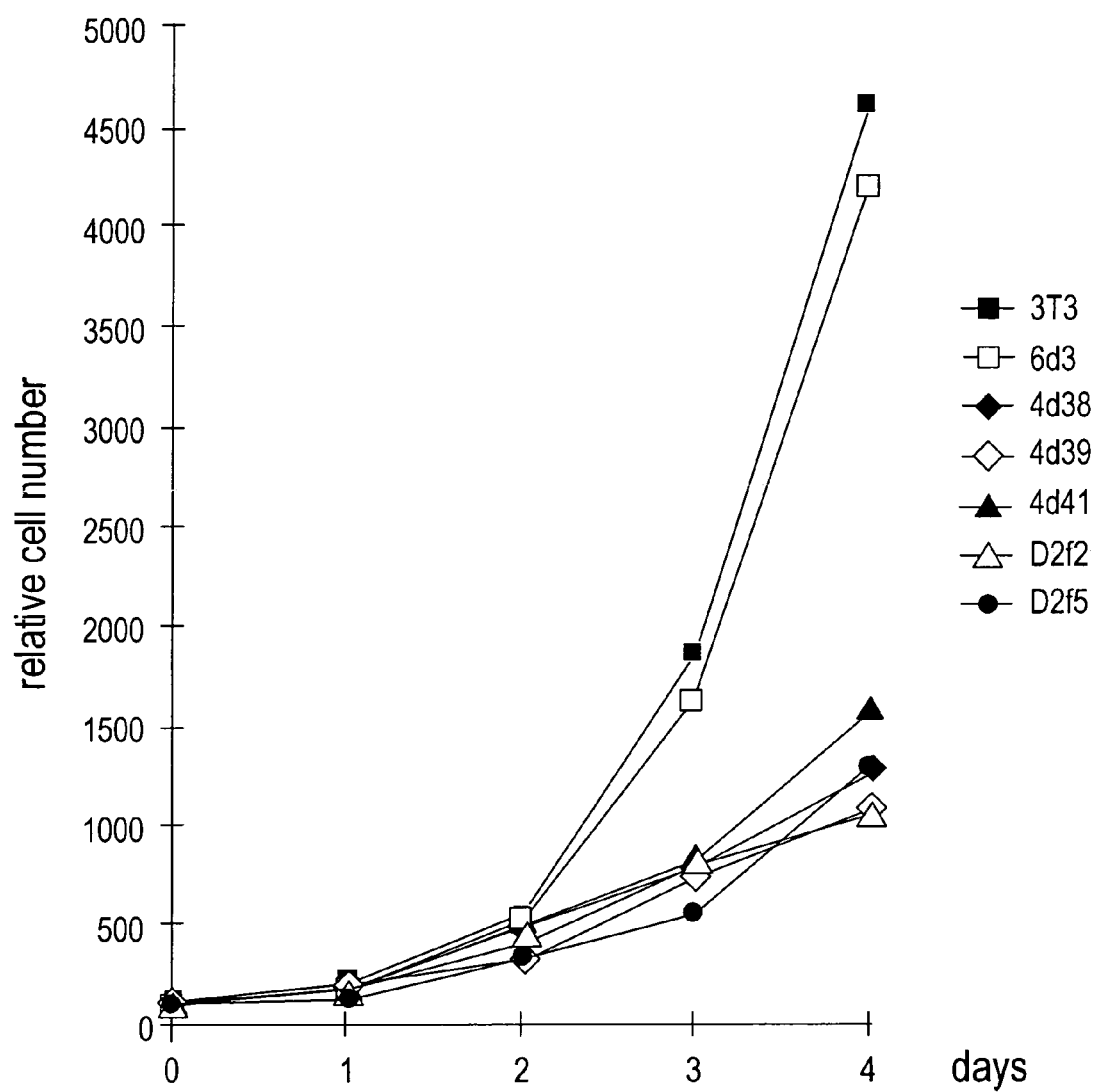
FIG. 1 is a line graph showing growth curves of parental 3T3 cells and of cell lines expressing the dn forms of cdk2 (lines D2f2 and D2f5), of cdk6 (lines 6d3) or cdk4 (lines 4d38, 4d39 and 4d41) in 10% serum.

The present invention is generally directed to methods which make use of the present inventors' discovery that cyclin dependent kinase 6 (cdk6) plays a previously unknown role in the cell cycle. Specifically, the present inventors have demonstrated that the functions of cdk4 and cdk6 are distinct, despite the high degree of homology between the two proteins. Whereas cdk4 is essential for optimal growth of some cell types, it appears that cdk6 is not. Taken together, the data presented herein indicate that cdk6, which is activated soon after cell growth is induced after quiescence, may act to induce genes which can cause withdrawal from the cell cycle, if growth is inappropriate at the time.

More particularly, the present invention relates to the surprising discovery by the present inventors that, contrary to the previously presumption that cdk4 and cdk6 perform very similar functions in cells, cdk4 and cdk6 proteins perform differential roles in cells. Specifically, the present inventors have made the following discoveries. First, the present inventors demonstrate herein that abrogation of cdk4 has dramatic effects on cell cycle progression and growth-control properties, whereas cdk6 abrogation has virtually no affect, indicating that cdk6 activity may not be a requirement for cell cycle progression, at least in 3T3 cells. Second, cell lines stably over-expressing cdk6 not only had elevated cdk6 levels but kinase activity was now detected and maintained throughout the cell cycle. These cell lines had a markedly reduced growth rate, now stably over-produced the p53 growth-suppressing proteins, and exhibited enhanced sensitivity to ultraviolet light, indicating that cdk6 plays a significant role in the cells' ability to respond to environmental stimuli and that, after cells enter the proliferative state, cdk6 may be involved in halting cell cycle progression if growth is inappropriate. Third, a comparative analysis of normal human mammary epithelial cells and tumor-derived cell lines revealed that, whereas most cell cycle proteins varied greatly in amount among the cell types, cdk6 was always present in lower amount in the tumor cell lines as compared to normal breast cells, and in several breast tumor cell lines, cdk6 could not be detected, indicating that reduced cdk6 levels in breast epithelial cells could contribute to a malignant phenotype. Fourth, cdk6 transiently and selectively interacts with Fyn, but not Lck, within minutes of T-cell activation. Following this initial interaction, cdk6, but not Fyn, migrates to the T-cell nucleus. Taken together, the present inventors have discovered a previously unknown function for cdk6 in several cell types, which has led the present inventors to develop novel methods of regulating cell growth, monitoring cell growth, and detecting the potential for inappropriate cell growth, as well as methods for identifying compounds useful in such methods.

Previously, the use of dominant-negative forms of cdk family members has indicated important roles for cdks 1, 2 and 3 in cell growth (van den Heuvel et al., 1993, *Science* 262:2050–2054). Inhibition of the endogenous enzymes by expression of dominant-negative forms inhibited cell growth. The present inventors describe herein that the expression of dominant negative forms of cdk4 and cdk6 in 3T3 cells demonstrates a dramatic difference between the two kinases. Whereas abrogation of cdk4 activity extended G1-phase and reduced entry into S-phase, reduction of the burst of cdk6 activity seen after cells re-entered the cell cycle had virtually no effect on cell growth. These observations indicated that cdk6 may not have a direct growth-promoting function. In fact, analysis of stable transfectants overexpressing cdk6 indicated that such cells overproduced growth-suppressing molecules such as p53 and the Rb family member p130, had a reduced growth rate and were more susceptible to apoptosis induced by irradiation with ultraviolet light. These results indicate that, whereas cdk4 promotes cell growth, its homologue, cdk6, is involved in pathways which negatively regulate growth. Without being bound by theory, the present inventors believe that cdk6 is involved in a pathway which responds to environmental factors which indicate that further growth is inappropriate. Thus, its absence or impaired function may lead to unrestrained growth.

The present inventors have discovered that cdk6 functions very early in G1 phase, perhaps determining whether or not cells will continue in the cell cycle after being activated to re-enter it. As described in Examples 1–3, the present inventors determined the effects of reduced cdk2, cdk4 or cdk6 kinase in 3T3 cells. In contrast to previous studies (van den Heuvel, 1993, supra), the efficacy of all three dominant-negative forms in specifically inhibiting endogenous levels of the corresponding kinases was demonstrated. Since cdk4 and cdk6 are regulated by the same D-type cyclins (cyclins D1 and D2 in 3T3 cells), it was initially expected that expression of one dominant-negative form (either cdk4 or cdk6) would also inhibit the other kinase. The dominant-negative forms do not have kinase activity because they are mutated in their ATP-binding sites, but presumably can still bind, and thus sequester cognate cyclins. Surprisingly), however, it was found that over-expression of the cdk6 dn protein had little effect on cdk4 activity in proliferating cells. This might have indicated that the cyclins are present in sufficient excess to prevent inhibition of cdk4, or alternatively, that at least some cdk6 is present in a form which is not binding cyclin, that cdk4 and cdk6 are utilizing different cyclin D members at different times in the cell cycle, or that the pools of cyclins utilized by the kinases are in different cellular compartments. However, as discussed below, a combination of data provided by the present inventors indicates that when cells are exposed to prolonged serum starvation, the dn form of cdk6 may in fact interfere with cdk4 function.

The present inventors have further demonstrated that overexpression of cdk6 in cells results in elevated cdk6 levels, kinase activity that is detected and maintained throughout the cell cycle, markedly decreased growth rate, over-production of the p53 and p130 growth-suppressing proteins and enhanced sensitivity to ultraviolet light.

The present inventors have also demonstrated that cdk6 was always present in lower amount in breast cell tumor cell lines as compared to normal breast cells, and in several breast tumor cell lines, cdk6 could not be detected, indicating that reduced cdk6 levels in breast epithelial cells could contribute to a malignant phenotype. This strict pattern of appearance was in marked contrast to any other molecule studied. Although the results presented here were observed when comparing cellular extracts prepared from the same numbers of cells, the same pattern for cdk6 was seen when samples containing the same protein amount were analyzed. Therefore, the present inventors have discovered a novel basis for the evaluation of breast cell tumors which has led to the ability to develop powerful diagnostic, monitoring and staging assays for breast tumors.

One embodiment of the present invention relates to a method (i.e., an assay) for assessing tumor cell growth in a patient. Such a method includes the steps of: (a) detecting cdk6 expression or biological activity in a cell sample from a patient; and, (b) comparing the cdk6 expression or biological activity as detected in step (a) to a baseline level of cdk6 expression or biological activity for the sample. Detection of reduced cdk6 expression or reduced cdk6 biological activity as compared to the baseline level of cdk6 expression or biological activity, is an indicator of increased cell growth or potential therefor in the patient. Additionally, detection of increased cdk6 expression or increased cdk6 biological activity as compared to the baseline level of cdk6 expression or biological activity as compared to the baseline level of cdk6 expression or biological activity, is an indicator of decreased cell growth or potential therefor in the patient. Detection of substantially the same cdk6 expression or biological activity (i.e., differences between sample and baseline control are not statistically significant with a degree of confidence of $p<0.05$) indicates no significant change or difference in cell growth in the patient (i.e., relative to the baseline control). The method of the present invention can be used for any type of tumor wherein cdk6 activity is found to be statistically significantly lower in tumor cells than in the corresponding normal cells. In a preferred embodiment, the method is used to assess breast (i.e., mammary) tumor growth in a patient. In this embodiment, the sample is preferably a mammary epithelial cell sample.

According to the present invention, the phrase "tumor cell growth" refers primarily to neoplastic transformation of a cell, which is a change of a cell or population of cells from a normal to malignant state. The change typically involves cellular proliferation at a rate which is more rapid than the growth observed for normal cells under the same conditions, and which is typically characterized by one or more of the following traits: continued growth even after the instigating factor (e.g., carcinogen, virus) is no longer present; a lack of structural organization and/or coordination with normal tissue, and typically, a formation of a mass of tissue, or tumor. A tumor, therefore, is most generally described as a proliferation of cells (e.g., a neoplasia, a growth, a polyp) resulting from neoplastic growth and is most typically a malignant tumor. In the case of a neoplastic transformation, a neoplasia is malignant or is predisposed to become malignant. Malignant tumors are typically characterized as being anaplastic (primitive cellular growth characterized by a lack of differentiation), invasive (moves into and destroys surrounding tissues) and/or metastatic (spreads to other parts of the body). As used herein, reference to a "potential for neoplastic transformation" or a "potential for tumor cell growth" refers to an expectation or likelihood that, at some point in the future, a cell or population of cells will display characteristics of neoplastic transformation, including rapid cellular proliferation characterized by anaplastic, invasive and metastatic growth. In the present invention, the expectation or likelihood of malignant tumor cell growth (i.e., a positive diagnosis of neoplastic transformation) is determined based on a detection of decreased cdk6 expression or biological activity in a cell as compared to a baseline (i.e., control) level of cdk6 expression or biological activity that is considered to be representative of cdk expression or biological activity in a normal (not neoplastically transformed) cell, as discussed in detail below.

This method of the present invention has several different uses. First, the method can be used to diagnose tumor growth, or the potential for tumor growth, in a patient. The patient can be an individual who is suspected of having a tumor, or an individual who is presumed to be healthy, but who is undergoing a routine screening for tumor growth. The patient can also be an individual who has previously been diagnosed with cancer and treated, and who is now under routine surveillance for recurring tumor growth. The terms "diagnose", "diagnosis", "diagnosing" and variants thereof refer to the identification of a disease or condition on the basis of its signs and symptoms. As used herein, a "positive diagnosis" indicates that the disease or condition, or a potential for developing the disease or condition, has been identified. In contrast, a "negative diagnosis" indicates that the disease or condition, or a potential for developing the disease or condition, has not been identified. Therefore, in the present invention, a positive diagnosis (i.e., a positive assessment) of tumor growth (i.e., malignant or inappropriate cell growth or neoplastic transformation), or the potential therefor, means that the indicators (e.g., signs, symptoms) of tumor growth according to the present invention (i.e., reduced cdk6 expression or biological activity as compared to a baseline control) have been identified in the sample obtained from the patient. Such a patient can then be prescribed treatment to reduce or eliminate the tumor growth. Similarly, a negative diagnosis (i.e., a negative assessment) for tumor growth or a potential therefor means that the indicators of tumor growth or a likelihood of developing tumor growth as described herein (i.e., reduced cdk6 expression or biological activity as compared to a baseline control) have not been identified in the sample obtained from the patient. In this instance, the patient is typically not prescribed any treatment, but may be reevaluated at one or more timepoints in the future to again assess tumor growth. Baseline levels for this particular embodiment of the method of tumor growth assessment of the present invention are typically based on a "normal" or "healthy" sample from the same bodily source as the test sample (i.e., the same tissue, cells or bodily fluid), as discussed in detail below.

In a second embodiment, the method of the present invention can be used more specifically to "stage" a tumor in a patient. Therefore, the patient can be diagnosed as having a tumor by the method as discussed above, or by any other suitable method (e.g, physical exam, X-ray, CT scan, blood test for a tumor antigen, surgery), and then (or at the same time, when the present method is also used as a diagnostic), the method of the present invention can be used to determine the stage of progression of tumor growth in an individual. For most cancer types, standard staging criteria exist and are known in the art. For example, in breast tumors, there are five different general stages of tumor development which are known and acknowledged in the art as stages 0, I, II, III and IV (although these stages can be grouped into more complex subgroups based on more specific indicators). In this embodiment of the method of tumor growth assessment of the present invention, the cdk6 expression and/or biological activity in the patient sample is compared to a panel of several different "baseline" levels of cdk6 expression or biological activity, wherein each baseline level represents a previously established level for a given stage of the cancer being diagnosed. For example, for a breast tumor staging assay, baseline levels of cdk6 expression and/or biological activity can be established for Stages I, II, III and IV of breast tumor cells (e.g., using an average level determined from a random sampling of tumors from different patients at the various stages). Therefore, in this embodiment, the level of expression of cdk6 expression or biological activity in the patient sample is compared to the various baseline levels corresponding to the different stages of tumor growth to identify the baseline level that is statistically closest to the level of cdk6 expression or biological activity detected in the patient. The ability to "stage" a tumor in the method of the present invention allows the physician to more appropriately prescribe treatment for the patient.

In a third embodiment of this method of the present invention, the method is used to monitor the success, or lack thereof, of a treatment for cancer in a patient that has been diagnosed as having cancer. In this embodiment, the baseline level of cdk6 expression or biological activity typically includes the previous level of cdk6 expression or biological activity in a sample of the patient's tumor, so that a new level of cdk6 expression or biological activity can be compared to determine whether tumor cell growth is decreasing, increasing, or substantially unchanged as compared to the previous, or first sample (i.e., the initial sample which presented a positive diagnosis). In addition, or alternatively, a baseline established as a "normal" or "healthy" level of cdk6 expression or biological activity can be used in this embodiment. This embodiment allows the physician to monitor the success, or lack of success, of a treatment that the patient is receiving for cancer, and can help the physician to determine whether the treatment should be modified. In one embodiment of the present invention, the method includes additional steps of modifying cancer treatment for the patient based on whether an increase or decrease in cell growth is indicated by evaluation of cdk6 expression and/or biological activity in the patient.

The first step of the method of the present invention includes detecting cdk6 expression or biological activity in a cell sample from a patient. According to the present invention, the term "cell sample" can be used generally to refer to a sample of any type which contains cells to be evaluated by the present method, including but not limited to, a sample of isolated cells, a tissue sample and/or a bodily fluid sample. According to the present invention, a sample of isolated cells is a specimen of cells, typically in suspension or separated from connective tissue which may have connected the cells within a tissue in vivo, which have been collected from an organ, tissue or fluid by any suitable method which results in the collection of a suitable number of cells for evaluation by the method of the present invention. The cells in the cell sample are not necessarily of the same type, although purification methods can be used to enrich for the type of cells which are preferably evaluated. Cells can be obtained, for example, by scraping of a tissue, processing of a tissue sample to release individual cells, or isolation from a bodily fluid. A tissue sample, although similar to a sample of isolated cells, is defined herein as a section of an organ or tissue of the body which typically includes several cell types and/or cytoskeletal structure which holds the cells together. One of skill in the art will appreciate that the term "tissue sample" may be used, in some instances, interchangeably with a "cell sample", although it is preferably used to designate a more complex structure than a cell sample. A tissue sample can be obtained by a biopsy, for example, including by cutting, slicing, or a punch. A bodily fluid sample, like the tissue sample, contains the cells to be evaluated for cdk6 expression or biological activity, and is a fluid obtained by any method suitable for the particular bodily fluid to be sampled. Bodily fluids suitable for sampling include, but are not limited to, blood, mucous, seminal fluid, saliva, breast milk, bile and urine.

In general, the sample type (i.e., cell, tissue or bodily fluid) is selected based on the accessibility and structure of the organ or tissue to be evaluated for tumor cell growth and/or on what type of cancer is to be evaluated. For example, if the organ/tissue to be evaluated is the breast, the sample cap be a sample of epithelial cells from a biopsy (i.e., a cell sample) or a breast tissue sample from a biopsy (a tissue sample). The sample that is most useful in the present invention will be cells or tissues isolated from a patient by a biopsy or surgery.

Once a sample is obtained from the patient, the sample is evaluated for detection of cdk6 expression or biological activity in the cells of the sample. The phrase "cdk6 expression" can generally refer to cdk6 mRNA transcription or cdk6 protein translation. Preferably, the method of detecting cdk6 expression or biological activity in the patient is the same or qualitatively equivalent to the method used for detection of cdk6 expression or biological activity in the sample used to establish the baseline level.

Methods suitable for detecting cdk6 transcription include any suitable method for detecting and/or measuring mRNA levels from a cell or cell extract. Such methods include, but are not limited to: polymerase chain reaction (PCR), reverse transcriptase PCR (RT-PCR), in situ hybridization, Northern blot, sequence analysis, and detection of a reporter gene. Such methods for detection of transcription levels are well known in the art, and many of such methods are described in detail below (See Northern blot analysis described in Examples), in Sambrook et al., *Molecular Cloning: A Laboratory Manual*, Cold Spring Harbor Labs Press, 1989 and/or in Glick et al., *Molecular Biotechnology: Principles and Applications of Recombinant DNA*, ASM Press, 1998; Sambrook et al., ibid., and Glick et al., ibid. are incorporated by reference herein in their entireties. The nucleotide and amino acid sequence for cdk6 in different mammalian species can be found in public databases, such as GenBank® in the National Center for Biotechnology Information. For example, the nucleotide and amino acid sequence for human cdk6 can be found in the NCBI database under Primary Accession No. NM_001259 (GenBank® No. 4502740). Measurement of cdk6 transcription is suitable when the sample is a cell or tissue sample; therefore, when the sample is a bodily fluid sample containing cells or cellular extracts, the cells are typically isolated from the bodily fluid to perform the expression assay.

cdk6 expression can also be identified by detection of cdk6 translation. Methods suitable for the detection of cdk6 protein include any suitable method for detecting and/or measuring proteins from a cell or cell extract. Such methods include, but are not limited to, immunoblot (e.g., Western blot), enzyme-linked immunosorbant assay (ELISA), radioimmunoassay (RIA), immunoprecipitation, immunohistochemistry and immunofluorescence. Particularly preferred methods for detection of proteins include any single-cell assay, including immunohistochemistry and immunofluorescence assays. Such methods are well known in the art. Furthermore, antibodies against cdk6 are known in the art and are publicly available, for example, from Santa Cruz Biotechnology (Santa Cruz, Calif.). Detection of cdk6 in a cell by immunoblot analysis, by way of example, is demonstrated in the Examples section.

The term, "cdk6 biological activity" refers to any biological action of the cdk6 protein, including, but not limited to, cdk6 enzymatic activity (i.e., kinase activity). Methods to detect cdk6 biological activity are also well known in the art and include, but are not limited to, assays for the detection of cdk6 kinase activity. Procedures for the isolation and assay of several cdk's, including cdk6 have been described in the art (Matsushime et al., 1994, *Mol. Cell. Biol.* 14:2066–2076; Meyerson et al., 1994, *Mol. Cell. Biol.* 14:2077–2086; Lucas et al., 1995, *J. Immunol.* 154:6275–6284; and Lucas et al., 1995, *J. Cell. Physiol.* 165:406–416; all are incorporated by reference in their entireties). The method for cdk6 kinase assay is also described in detail in the Examples section. Other methods for detection of cdk6 biological activity, including alternate methods of detecting kinase activity, will be known to those of skill in the art and are encompassed by the present invention.

The method of the present invention includes a step of comparing the level of cdk6 expression or biological activity detected in step (a) to a baseline level of cdk6 expression or biological activity. According to the present invention, a "baseline level" is a control level, and in some embodiments, a normal level, of cdk6 expression or activity against which a test level of cdk6 expression or biological activity (i.e., in the patient sample) can be compared. Therefore, it can be determined, based on the control or baseline level of cdk6 expression or biological activity, whether a sample to be evaluated for tumor cell growth has a measurable increase, decrease, or no change in cdk6 expression or biological activity, as compared to the baseline level. As discussed above, the baseline level can be indicative of different states of cell growth, depending on the primary use of the assay. For example, the baseline level can be indicative of the cell growth expected in a normal (i.e., healthy or negative control) cell sample. Therefore, the term "negative control" used in reference to a baseline level of cdk6 expression or biological activity refers to a baseline level established in a cell sample from the patient or from a population of individuals which is believed to be normal (i.e., non-tumorous, not undergoing neoplastic transformation, not exhibiting inappropriate cell growth). It is noted that the "negative control" is typically actually a higher level of cdk6 than would be detected in an experimental cell having inappropriate, increased cell growth, because the cdk6 expression/biological activity and cell growth are inversely related. In another embodiment, a baseline can be indicative of a positive diagnosis of tumor cell growth. Such a baseline level, also referred to herein as a "positive control" baseline, refers to a level of cdk6 expression or biological activity established in a cell sample from the patient, another patient, or a population of individuals, wherein the sample was believed to be neoplastically transformed (i.e., tumorous, exhibiting inappropriate cell growth, cancerous). It is noted that this "positive control" will typically actually represent a lower level of cdk6 than in a normal cell, again due to the inverse relationship between cdk6 and cell growth. In one aspect of this embodiment, the baseline can be indicative of a particular stage of tumor cell growth, which will allow a patient's sample to be "staged" (i.e., the stage of the cancer in the patient can be identified). In yet another embodiment, the baseline level can be established from a previous sample from the patient being tested, so that the tumor growth of a patient can be monitored over time. Methods for detecting cdk6 expression or biological activity are described in detail above.

The method for establishing a baseline level of cdk6 expression or activity is selected based on the sample type, the tissue or organ from which the sample is obtained, the status of the patient to be evaluated, and, as discussed above, the focus or goal of the assay (e.g., diagnosis, staging, monitoring). Preferably, the method is the same method that will be used to evaluate the sample in the patient.

In one embodiment, the baseline level of cdk6 expression or biological activity is established in an autologous control sample obtained from the patient. The autologous control sample can be a sample of isolated cells, a tissue sample or a bodily fluid sample, and is preferably a cell sample or tissue sample. According to the present invention, and as used in the art, the term "autologous" means that the sample is obtained from the same patient from which the sample to be evaluated is obtained Preferably, the control sample is obtained from the same organ or tissue as the sample to be evaluated, such that the control sample serves as the best possible baseline for the sample to be evaluated. In one embodiment, when the goal of the assay is diagnosis of abnormal cell growth, it is desirable to take the control sample from a population of cells or a tissue which is believed to represent a "normal" cell or tissue, or at a minimum, a cell or tissue which is least likely to be undergoing or potentially be predisposed to develop tumor cell growth. For example, if the sample to be evaluated is an area of apparently abnormal cell growth, such as a tumorous mass, the control sample is preferably obtained from a section of apparently normal tissue (i.e., an area other than and preferably a reasonable distance from the tumorous mass) in the tissue or organ where the tumorous mass is growing. In one aspect, if a tumor to be evaluated is in the breast, the test sample would be obtained from the suspected tumor mass and the control sample would be obtained from a different section of the breast (or a different breast), which is separate from the area where the mass is located and which does not show signs of uncontrolled cellular proliferation.

In another embodiment, when the goal is to monitor tumor cell growth in the patient, the autologous baseline sample will be a previous sample from the patient which was taken from an apparent or confirmed tumorous mass, and/or from apparently normal (i.e., non-tumor) tissue in the patient. Therefore, a second method for establishing a baseline level of cdk6 expression or biological activity is to establish a baseline level of cdk6 expression or biological activity from at least one measurement of cdk6 expression or biological activity in a previous sample from the same patient. Such a sample is also an autologous sample, but is taken from the patient at a different time point than the sample to be tested. Preferably, the previous sample(s) were of a same cell type, tissue type or bodily fluid type as the sample to be presently evaluated. In one embodiment, the previous sample resulted in a negative diagnosis (i.e., no tumor cell growth, or potential therefor, A was identified). In this embodiment, a new sample is evaluated periodically (e.g., at annual physicals), and as long as the patient is determined to be negative for tumor development, an average or other suitable statistically appropriate baseline of the previous samples can be used as a "negative control" for subsequent evaluations. For the first evaluation, an alternate control can be used, as described below, or additional testing may be performed to confirm an initial negative diagnosis, if desired, and the value for cdk6 expression or biological activity can be used thereafter. This type of baseline control is frequently used in other clinical diagnosis procedures where a "normal" level may differ from patient to patient and/or where obtaining an autologous control sample at the time of diagnosis is either not possible, not practical or not beneficial. For example, for a patient who has periodic mammograms, the previous mammograms serve as baseline controls for the mammary tissue of the individual patient. Similarly, for a patient who is regularly screened for prostate cancer by evaluation of levels of prostate cancer antigen (PCA), previous PCA levels are frequently used as a baseline for evaluating whether the individual patient experiences a change.

In another embodiment, the previous sample from the patient resulted in a positive diagnosis (i.e., tumor growth was positively identified). In this embodiment, the baseline provided by the previous sample is effectively a positive control for tumor growth, and the subsequent samplings of the patient are compared to this baseline to monitor the progress of the tumor growth and/or to evaluate the efficacy of a treatment which is being prescribed for the cancer. In this embodiment, it may also be beneficial to have a negative baseline level of cdk6 expression or biological activity, so that a baseline for remission or regression of the tumor can be set. Monitoring of a patient's tumor growth can be used by the clinician to modify cancer treatment for the patient based on whether an increase or decrease in cell growth is indicated.

It will be clear to those of skill in the art that some samples to be evaluated will not readily provide an obvious autologous control sample, or it may be determined that collection of autologous control samples is too invasive and/or causes undue discomfort to the patient. In these instances, an alternate method of establishing a baseline level of cdk6 expression or biological activity should be used, examples of which are described below.

A third method for establishing a baseline level of cdk6 expression or biological activity is to establish a baseline level of cdk6 expression or biological activity from control samples, and preferably control samples that were obtained from a population of matched individuals. It is preferred that the control samples are of the same sample type as the sample type to be evaluated for cdk6 expression or biological activity. According to the present invention, the phrase "matched individuals" refers to a matching of the control individuals on the basis of one or more characteristics which are suitable for the type of cell or tumor growth to be evaluated. For example, control individuals can be matched with the patient to be evaluated on the basis of gender, age, race, or any relevant biological or sociological factor that may affect the baseline of the control individuals and the patient (e.g., preexisting conditions, consumption of particular substances, levels of other biological or physiological factors). For example, levels of cdk6 expression in the breast of a normal individual (i.e., having breast tissue that is not neoplastically transformed or predisposed to such transformation) may be higher in individuals of a given classification (e.g., elderly vs. teenagers, smokers vs. non-smokers) (although such variation in groups is not currently known). To establish a control or baseline level of cdk6 expression or biological activity, samples from a number of matched individuals are obtained and evaluated for cdk6 expression or biological activity. The sample type is preferably of the same sample type and obtained from the same organ, tissue or bodily fluid as the sample type to be evaluated in the test patient. The number of matched individuals from whom control samples must be obtained to establish a suitable control level (e.g., a population) can be determined by those of skill in the art, but should be statistically appropriate to establish a suitable baseline for comparison with the patient to be evaluated (i.e., the test patient). The values obtained from the control samples are statistically processed to establish a suitable baseline level using methods standard in the art for establishing such values.

A baseline such as that described above can be a negative control baseline, such as a baseline established from a population of apparently normal control individuals. Alternatively, as discussed above, such a baseline can be established from a population of individuals that have been positively diagnosed as having cancer, and particularly, cancer of a specified stage, as set forth by the medical community, so that one or more baseline levels can be established for use in staging a cancer in the patient to be evaluated. Therefore, in one embodiment, the baseline level is one or more breast tumor control samples that is correlated with a particular stage of breast tumor development. For example, tumor samples from an appropriate number of individuals which have been diagnosed as having a particular stage of a given cancer (e.g., Stage I breast cancer) are tested for cdk6 expression or biological activity. The values obtained from these control samples are statistically processed to establish a suitable baseline level using methods standard in the art for establishing such values, and the baseline is noted as being indicative of that particular stage of cancer. Preferably, a similar value is determined for each of the established stages of the given cancer, so that a panel of baseline values, each representing a different stage of the cancer, is formed. The level of cdk6 expression or biological activity in the patient sample is then compared to each of the baseline levels to determine to which baseline the cdk6 level of the patient is statistically closest. It will be appreciated that a given patient sample may fall between baseline levels of two different stages such that the best diagnosis is that the patient tumor is at least at the lower stage, but is perhaps in the process of advancing to the higher stage. The data provided by this method can be used in conjunction with current cancer staging methods to assist the physician in the evaluation of the patient and in prescribing suitable treatment for the cancer.

It will be appreciated by those of skill in the art that a baseline need not be established for each assay as the assay is performed but rather, a baseline can be established by referring to a form of stored information regarding a previously determined baseline level of cdk6 expression for a given control sample, such as a baseline level established by any of the above-described methods. Such a form of stored information can include, for example, but is not limited to, a reference chart, listing or electronic file of population or individual data regarding "normal" (negative control) or tumor positive (including staged tumors) cdk6 expression; a medical chart for the patient recording data from previous evaluations; or any other source of data regarding baseline cdk6 expression that is useful for the patient to be diagnosed.

After the level of cdk6 expression or biological activity is detected in the sample to be evaluated for tumor cell growth, such level is compared to the established baseline level of cdk6 expression or biological activity, determined as described above. Also, as mentioned above, preferably, the method of detecting used for the sample to be evaluated is the same or qualitatively and/or quantitatively equivalent to the method of detecting used to establish the baseline level, such that the levels of the test sample and the baseline can be directly compared. In comparing the test sample to the baseline control, it is determined whether the test sample has a measurable decrease or increase in cdk6 expression or biological activity over the baseline level, or whether there is no statistically significant difference between the test and baseline levels. After comparing the levels of cdk6 expression or biological activity in the samples, the final step of making a diagnosis, monitoring, or staging of the patient can be performed.

Detection of a decreased level of cdk6 expression or biological activity in the sample to be evaluated (i.e., the test sample) as compared to the baseline level indicates that, as compared to the baseline sample, increased cell growth or a potential therefor is indicated in the test cells. This indication of increased cell growth is evaluated based on what the baseline represents, and can mean: (1) a positive diagnosis of tumor cell growth (neoplastic transformation) or potential for tumor cell growth in the patient; (2) continued or increased tumor cell growth in a patient previously diagnosed with a cancer; and/or (3) a higher stage of tumor growth than that represented by the baseline. More specifically, if the baseline is a normal or negative control sample (i.e., autologous or otherwise established, such as from a population control), a detection of decreased cdk6 expression or biological activity in the test sample as compared to the control sample indicates that the cells in the test sample are undergoing (or are at risk of undergoing) increased, and likely inappropriate (i.e., tumorous, neoplastic) cell growth. If the baseline sample is a previous sample from the patient (or a population control) and is representative of a positive diagnosis of tumor cell growth in the patient (i.e., a positive control), a detection of decreased cdk6 expression or biological activity in the sample as compared to the baseline indicates that the cells in the test sample are experiencing increased tumor growth or a potential therefor, which would suggest to a clinician that a treatment currently being prescribed, for example, is not controlling the tumor growth or that tumor growth in the patient has recurred. If the baseline sample is representative of a particular stage of tumor, a detection of decreased cdk6 expression or biological activity in the sample as compared to the baseline indicates that the cells in the test sample are at a higher stage of tumor growth than the stage represented by the baseline sample (e.g., if the baseline represented a stage I breast tumor, the test sample is likely to be higher than stage I, and should be compared to a stage II, III or IV baseline).

Detection of an increased level of cdk6 expression or biological activity in the sample to be evaluated (i.e., the test sample) as compared to the baseline level indicates that, as compared to the baseline sample, decreased cell growth or a potential therefor is indicated in the test cells. This indication of decreased cell growth is evaluated based on what the baseline represents, and can mean: (1) a negative diagnosis of tumor cell growth (neoplastic transformation)

or potential for tumor cell growth in the patient; (2) reduced tumor cell growth in a patient previously diagnosed with a cancer; and/or (3) a lower stage of tumor growth than that represented by the baseline. More specifically, if the baseline is a normal or negative control (autologous or otherwise established, such as from a population control), a detection of increased cdk6 expression or biological activity in the test sample as compared to the control sample indicates that the cells in the test sample are also normal and are not predicted to be at risk of undergoing inappropriate (i.e., tumorous, neoplastic) cell growth. If the baseline sample is a previous sample from the patient (or from a population control) and is representative of a positive diagnosis of tumor cell growth in the patient (i.e., a positive control), a detection of increased cdk6 expression or biological activity in the sample as compared to the baseline indicates that the cells in the test sample are experiencing decreased tumor growth or a potential therefor, which suggests to a clinician, for a patient that has cancer, that a treatment currently being prescribed, for example, is successfully controlling the tumor growth or that a tumor in the patient is in remission or eliminated. If the baseline sample is representative of a particular stage of tumor, a detection of increased cdk6 expression or biological activity in the sample as compared to the baseline indicates that the cells in the test sample are at a lower stage of tumor growth than the stage represented by the baseline sample (e.g., if the baseline represented a stage II breast tumor, the test sample is likely to be lower than stage I, and should be compared to a stage I and negative (normal) baseline).

Finally, detection of cdk6 expression that is not statistically significantly different than the cdk6 expression or biological activity in the baseline sample indicates that, as compared to the baseline sample, no difference in cell growth or a potential therefor is indicated in the test cells. This indication of effectively a "baseline level" of cell growth in the test cell is evaluated based on what the baseline represents, and can mean: (1) a negative or positive diagnosis of tumor cell growth (neoplastic transformation) or potential therefor in the patient; (2) unchanged tumor cell growth in a patient previously diagnosed with a cancer; and/or (3) a correlation with a stage of tumor growth that is represented by the baseline. More specifically, if the baseline is a normal or negative control (autologous or otherwise established, such as from a population control), a detection of cdk6 expression or biological activity in the test sample that is not statistically significantly different than the baseline sample indicates that the cells in the test sample are also normal and are not predicted to be at risk of undergoing inappropriate (i.e., tumorous, neoplastic) cell growth. If the baseline sample is a previous sample from the patient (or from a population control) and is representative of a positive diagnosis of tumor cell growth in the patient (i.e., a positive control), a detection of cdk6 expression or biological activity in the sample that is not statistically significantly different than the baseline indicates that the cells in the test sample are experiencing tumor cell growth or a potential therefor, and the patient should be further evaluated for cancer. In a patient who has cancer and is being monitored for tumor progression, a detection of cdk6 expression or biological activity in the test sample that is not statistically significantly different than the baseline sample indicates that the tumor is neither increasing (progressing) or decreasing (regressing). Such a diagnosis might suggest to a clinician that a treatment currently being prescribed, for example, is ineffective in controlling the tumor growth. Finally, if the baseline sample is representative of a particular stage of tumor, a detection of cdk6 expression or biological activity in the test sample that is not statistically significantly different than the baseline sample indicates that the cells in the test sample are at substantially the same stage of tumor growth as the stage represented by the baseline sample.

As discussed above, a positive diagnosis indicates that increased cell growth, and possibly tumor cell growth (neoplastic transformation), has occurred, is occurring, or is statistically likely to occur in the cells or tissue from which the sample was obtained. In order to establish a positive diagnosis, the level of cdk6 activity is decreased (or in the case of a negative diagnosis, increased) over the established baseline by an amount that is statistically significant (i.e., with at least a 95% confidence level, or $p<0.05$). Preferably, detection of at least about a 30% decrease in ckd6 expression or biological activity in the sample as compared to the baseline level results in a positive diagnosis of increased cell growth for said sample, as compared to the baseline. More preferably, detection of at least about a 50% decrease, and more preferably at least about a 70% decrease, and more preferably at least about a 90% decrease in ckd6 expression or biological activity in the sample as compared to the baseline level results in a positive diagnosis of increased cell growth for said sample. In one embodiment, a 1.5 fold decrease in ckd6 expression or biological activity in the sample as compared to the baseline level results in a positive diagnosis of increased cell growth for said sample. More preferably, detection of at least about a 3 fold decrease, and more preferably at least about a 6 fold decrease, and even more preferably, at least about a 12 fold decrease, and even more preferably, at least about a 24 fold decrease in ckd6 expression or biological activity as compared to the baseline level results in a positive diagnosis of increased cell growth for said sample. As discussed in detail above, if the level of cdk6 expression or biological activity in the test sample is greater than the baseline level of cdk6 expression or biological activity (with statistical significance as described above), then a negative diagnosis of decreased cell growth, as compared to the baseline, is indicated. As discussed above, a negative diagnosis typically refers to a determination that neoplastic transformation has not occurred in the cells or tissue from which the sample was obtained and that there is no indication that neoplastic transformation is or will occur in such cells as of the time the evaluation is performed, or that reduced tumor cell growth is occurring in the cells or tissue from which the sample was obtained as compared to the baseline. A negative diagnosis may be used in future evaluations to establish a negative baseline for the patient and/or be used to assist with the establishment of a population control level when combined with results from other patients considered to be normal. Finally, if the level of cdk6 expression or biological activity in the test sample is statistically significantly the same as the baseline level of cdk6 expression or biological activity (using the confidence levels set forth above), then the test cells are believed to be experiencing substantially the same cell growth as the baseline sample, and the diagnosis is dependent on what the baseline sample represents (i.e., a positive or negative control, or a stage of tumor development). It will be appreciated that in any embodiment, the final evaluation of what is indicated by a change in cdk6 expression or biological activity as compared to the baseline, beyond the established indication of increased, decreased, or unchanged cell growth, is dependent upon what the baseline represents.

In one embodiment, a positive diagnosis of neoplastic transformation in a sample obtained from a patient can be indicative of the development, or potential for development, of neoplastic transformation of the cell type, tissue and/or organ from which the sample was obtained. For example, a positive diagnosis in a sample obtained from the breast is indicative of breast cancer, or the potential therefor, in the patient. Once a positive diagnosis is made using the present method, the diagnosis can be substantiated, if desired, using any suitable alternate method of detection of tumor cell growth, including pathology screening, blood screening for tumor antigens, and surgery. In one embodiment of the present invention, the method can include an additional step of confirming the diagnosis of tumor cell growth using such an alternate form of detection of neoplastic transformation such as surgery, tumor antigen screening, biopsy and/or pathology/histology. A positive diagnosis of tumor cell growth in an individual allows for the commencement of appropriate treatment protocols. Since the method of the present invention is useful for the early detection of inappropriate cell growth in an individual, treatment protocols are expected to be more effective and result in prolonged survival rates.

Yet another embodiment of the present invention relates to an assay kit for diagnosing tumor cell growth or a potential for tumor cell growth in a patient. The assay kit includes: (a) a means for detecting cdk6 expression or biological activity in a cell sample; and (b) a means for detecting a control marker characteristic of the cell type that is being sampled.

This assay kit, and the diagnostic method of the present invention are believed to be superior and more powerful than previously described markers for tumors, and particularly, for breast cell tumors. Diagnostic assays described prior to the present invention typically rely on markers which are not necessarily present in all patients that have or are at risk of developing tumors (i.e., genetic markers that are predictive of only a subset of cancer patients, such as BRACI for breast cell tumors). Moreover, such markers are typically detected as an "all or nothing" response, and therefore provide only a "yes or no" answer and are not useful for staging tumors, for example. In contrast, the method of the present invention is believed to be effective for the detection of tumor cell growth or a potential therefor in all breast tumor cells, regardless of whether other genetic markers have predisposed an patient to the cancer. Moreover, the method of the present invention is designed to test for varying levels of cdk6 expression and/or biological activity as a marker of neoplastic transformation, and therefore provides more than a "yes/no" answer in that tumor development in a patient can be staged using the assay kit and method of the present invention. Therefore, the assay kit and diagnostic method of the present invention are believed to be significantly more powerful and useful than previously described tumor assays, particularly for the diagnosis of breast tumors.

According to the present invention, a means for detecting cdk6 expression or biological activity can be any suitable reagent which can be used in a method for detection of cdk6 expression or biological activity as described previously herein. Such reagents include, but are not limited to: a probe that hybridizes under stringent hybridization conditions to a nucleic acid molecule encoding cdk6 or a fragment thereof; RT-PCR primers for amplification of mRNA encoding cdk6 or a fragment thereof; and/or an antibody that selectively binds to cdk6. Preferred means for detection of cdk6 expression or biological activity include any reagents useful for immunohistochemistry and/or immunofluorescence, including antibodies against cdk6.

According to the present invention, a probe is a nucleic acid molecule which typically ranges in size from about 8 nucleotides to several hundred nucleotides in length. Such a molecule is typically used to identify a target nucleic acid sequence in a sample by hybridizing to such target nucleic acid sequence under stringent hybridization conditions. As used herein, stringent hybridization conditions refer to standard hybridization conditions under which nucleic acid molecules are used to identify similar nucleic acid molecules. Such standard conditions are disclosed, for example, in Sambrook et al., *Molecular Cloning: A Laboratory Manual*, Cold Spring Harbor Labs Press, 1989. Sambrook et al., ibid., is incorporated by reference herein in its entirety (see specifically, pages 9.31–9.62). In addition, formulae to calculate the appropriate hybridization and wash conditions to achieve hybridization permitting varying degrees of mismatch of nucleotides are disclosed, for example, in Meinkoth et al., 1984, *Anal. Biochem.* 138, 267–284; Meinkoth et al., ibid., is incorporated by reference herein in its entirety.

More particularly, stringent hybridization and washing conditions, as referred to herein, refer to conditions which permit isolation of nucleic acid molecules having at least about 70% nucleic acid sequence identity with the nucleic acid molecule being used to probe in the hybridization reaction, more particularly at least about 80%, and more particularly at least about 85%, and most particularly at least about 90%. Such conditions will vary, depending on whether DNA:RNA or DNA:DNA hybrids are being formed. Calculated melting temperatures for DNA:DNA hybrids are 10° C. less than for DNA:RNA hybrids. In particular embodiments, stringent hybridization conditions for DNA:DNA hybrids include hybridization at an ionic strength of 6×SSC (0.9 M Na$^+$) at a temperature of between about 20° C. and about 35° C., more preferably, between about 28° C. and about 40° C., and even more preferably, between about 35° C. and about 45° C. In particular embodiments, stringent hybridization conditions for DNA:RNA hybrids include hybridization at an ionic strength of 6×SSC (0.9 M Na$^+$) at a temperature of between about. 30° C. and about 45° C., more preferably, between about 38° C. and about 50° C., and even more preferably, between about 45° C. and about 55° C. These values are based on calculations of a melting temperature for molecules larger than about 100 nucleotides, 0% formamide and a G+C content of about 40%. Alternatively, $T_m$ can be calculated empirically as set forth in Sambrook et al., supra, pages 9.31 TO 9.62.

PCR primers are also nucleic acid sequences, although PCR primers are typically oligonucleotides of fairly short length which are used in polymerase chain reactions. PCR s primers and hybridization probes can readily be developed and produced by those of skill in the art, using sequence information from the target sequence. (See, for example, Sambrook et al., supra or Glick et al., supra).

Antibodies that selectively bind to cdk6 in the sample can be produced using cdk6 protein information available in the art. As used herein, the term "selectively binds to" refers to the ability of such an antibody to preferentially bind to a specific antigen, which in this embodiment, is cdk6. Antibodies useful in the assay kit and methods of the present invention can be either polyclonal or monoclonal antibodies. Such antibodies include functional equivalents such as antibody fragments and genetically-engineered antibodies, including single chain antibodies, that are capable of selectively binding to at least one of the epitopes of the protein used to obtain the antibodies. Such antibodies can include chimeric antibodies in which at least a portion of the heavy chain and/or light chain of an antibody is replaced with a corresponding portion from a different antibody. For example, a chimeric antibody of the present invention can include an antibody having an altered heavy chain constant region (e.g., altered isotype), an antibody having protein sequences derived from two or more different species of animal, and an antibody having altered heavy and/or light chain variable regions (e.g., altered affinity or specificity).

Generally, in the production of an antibody, a suitable experimental animal, such as a rabbit, hamster, guinea pig or mouse, is exposed to an antigen against which an antibody is desired. Typically, an animal is immunized with an effective amount of antigen that is injected into the animal. An effective amount of antigen refers to an amount needed to induce antibody production by the animal. The animal's immune system is then allowed to respond over a predetermined period of time. The immunization process can be repeated until the immune system is found to be producing antibodies to the antigen. In order to obtain polyclonal antibodies specific for the antigen, serum is collected from the animal that contains the desired antibodies. Such serum is useful as a reagent. Polyclonal antibodies can be further purified from the serum by, for example, treating the serum with ammonium sulfate. In order to obtain monoclonal antibodies, the immunized animal is sacrificed and B lymphocytes are recovered from the spleen. The B lymphocytes are then fused with myeloma cells to obtain a population of hybridoma cells capable of continual growth in suitable culture medium. Hybridomas producing a desired antibody are selected by testing the ability of an antibody produced by a hybridoma to bind to the antigen.

The means for detecting a control marker characteristic of the cell type that is being sampled can generally be any type of reagent that can be used in a method of detecting the presence of a known marker in a sample, such as by a method for detecting the presence of cdk6 described previously herein. Specifically, the means is characterized in that it identifies a specific marker of the cell type being analyzed that positively identifies the cell type. For example, in a breast tumor assay, it is desirable to screen breast epithelial cells for the level of cdk6 expression and/or biological activity. Therefore, the means for detecting a control marker identifies a marker that is characteristic of an epithelial cell and preferably, a breast epithelial cell, so that the cell is distinguished from other cell types, such as a fibroblast. Such a means increases the accuracy and specificity of the assay of the present invention. Such a means for detecting a control marker include, but are not limited to: a probe that hybridizes under stringent hybridization conditions to a nucleic acid molecule encoding a protein marker; PCR primers which amplify such a nucleic acid molecule; and/or an antibody that selectively binds to the control marker in the sample. Nucleic acid and amino acid sequences for many cell markers are known in the art and can be used to produce such reagents for detection. Examples of cell markers for epithelial cells include, but are not limited to any cytokeratin molecule. Examples of cell markers for breast epithelial cells include, but are not limited to cytokeratin 14, cytokeratin 19 and vimentin (see detailed discussion below).

The means for detecting of part (a) and or part (b) of the assay kit of the present invention can be conjugated to a detectable tag. Such a tag can be any suitable tag which allows for detection of the means of part (a) or (b) and includes, but is not limited to, a fluorescent tag, a chemiluminescent tag, a radioactive tag, a calorimetric tag, an enzyme, or other such detectable tags which are commonly used in detection assays such as those described herein.

In addition, the means for detecting of part (a) and or part (b) of the assay kit of the present invention can be immobilized on a substrate. Such a substrate can include any suitable substrate for immobilization of a detection reagent such as would be used in any of the previously described methods of detection. Briefly, a substrate suitable for immobilization of a means for detecting includes any solid support, such as any solid organic, biopolymer or inorganic support that can form a bond with the means for detecting without significantly effecting the activity and/or ability of the detection means to detect the desired target molecule. Exemplary organic solid supports include polymers such as polystyrene, nylon, phenol-formaldehyde resins, acrylic copolymers (e.g., polyacrylamide), stabilized intact whole cells, and stabilized crude whole cell/membrane homogenates. Exemplary biopolymer supports include cellulose, polydextrans (e.g., Sephadex®), agarose, collagen and chitin. Exemplary inorganic supports include glass beads (porous and nonporous), stainless steel, metal oxides (e.g., porous ceramics such as $ZrO_2$, $TiO_2$, $Al_2O_3$, and $NiO$) and sand.

In a preferred embodiment of the present invention, the assay kit is specifically formulated to test breast epithelial cells for cdk6 expression or biological activity, as a diagnostic kit for the detection of breast tumors. In this embodiment, the means for detecting cdk6 expression or biological activity can be the same as for the general assay kit (described above). The means for detecting a control marker characteristic of the cell type that is being sampled is a means for detecting a control marker characteristic of a breast epithelial cell. This means will ensure that the cell being evaluated for cdk6 expression and/or biological activity is a cell that is likely to form a tumor (i.e., a breast epithelial cell) and is not another cell, such as a fibroblast cell. Since preferred methods of analysis of the markers according to this embodiment are immunohistochemistry and immunofluorescent assays, the confirmation of the appropriate cell type is important. Preferred epithelial cell markers to identify using the means in part (b) include a cytokeratin, which is an epithelial-specific marker. There are at least 40 different cytokeratins that are expressed by epithelial cells; however, pan-specific cytokeratin antibodies are publicly available that can recognize any of the known cytokeratins. Such an antibody is available, for example, from Dako. Therefore, in a preferred embodiment, the test kit includes as the means of (b) an antibody that selectively binds to a cytokeratin. In a particularly preferred embodiment, such an antibody is a pan-specific cytokeratin antibody. Other embodiments include antibodies that selectively bind to a particular cytokeratin. Preferred control markers to detect in this embodiment are cytokeratins that are specifically expressed by breast epithelial cells, and include, but are not limited to, cytokeratin 19 (expressed by breast luminal epithelial cells), vimentin (expressed by breast basal epithelial cells) and cytokeratin 14 (expressed by breast myoepithelial cells). In another embodiment, this assay for breast tumor cells could include a third component of a normal cell control (i.e., a tissue sample from normal breast epithelium) which is suitable for screening using the other reagents in the kit.

According to the present invention, the method for assessing tumor growth in a patient, as well as other methods disclosed herein, is suitable for use in a patient that is a member of the Vertebrate class, Mammalia, including, without limitation, primates, livestock and domestic pets (e.g., a companion animal). Most typically, a patient will be a human patient.

Another embodiment of the present invention relates to a method to identify a compound useful for the inhibition of cell growth. Such a method includes the steps of: (a) detecting an initial level of cdk6 expression or biological activity in a cell; (b) contacting the cell with a test compound; (c) detecting a level of cdk6 expression or biological activity in the cell after contact of the cell with the compound; and, (d) selecting a compound that increases the expression or biological activity of cdk6 in the cell as compared to the initial level as being useful for inhibition of cell growth. The method can include a further step of detecting whether a compound selected in (d) inhibits growth of a cell.

Steps (a) and (c) of the method of the present invention require detection of cdk6 expression and/or biological activity in a cell. Detection of cdk6 expression and/or biological activity can include, but is not limited to: detecting cdk6 mRNA transcription (e.g., by polymerase chain reaction (PCR), reverse transcriptase-PCR (RT-PCR), in situ hybridization, Northern blot, sequence analysis or detection of a reporter gene); detecting cdk6 translation (e.g., by immunoblot, enzyme-linked immunosorbant assay (ELISA), radioimmunoassay (RIA), immunoprecipitation, immunohistochemistry and immunofluorescence); and/or detecting cdk6 biological activity (e.g., by detecting cdk6 kinase activity). Such methods for detection of cdk6 expression and biological activity have been discussed in detail above with regard to the method for assessing tumor cell growth, and that discussion applies to the detection cdk6 expression and biological activity here. The step of detection in step (a) is the control level of cdk6 expression or biological activity to which the detection in step (c) is to be compared and evaluated. The step of detection in step (c) is the experimental level of cdk6 expression or biological activity which indicates whether the test compound can change the level of cdk6 expression or biological activity in the cell, as compared to the level determined in step (a).

A cell suitable for use in the present method is any cell which expresses or can be induced to express, a detectable level of cdk6. A detectable level of cdk6 is a level which can be detected using any of the methods for cdk6 detection described herein. Since cdk6 is expressed by all mammalian cell types, virtually any cell could be selected. However, it will be appreciated by those of skill in the art that some cell types are more suitable for use in an in vitro assay (e.g., easy to maintain in culture, easy to obtain), and that cdk6 is more readily detectable in some cell types, and therefore, such cell types are preferable for use in the present invention. A preferred cell type to use in the method of the present invention is any cell type that has a naturally low expression of cdk6, so that an increase in cdk6 is readily detectable. Some preferred cells to use in the method of the present invention include, but are not limited to: fibroblasts and breast tumor cells. In one embodiment, the cell is a mammary cell, including a mammary epithelial cell. In another embodiment, the cell is a mammary tumor cell. In one embodiment, a cell suitable for use in the present method is a cell which has been transfected with a recombinant nucleic acid molecule encoding cdk6 and operatively linked to a transcription control sequence so that cdk6 is expressed by the cell. As discussed above, the nucleic acid sequence for human cdk6, as well as other mammalian cdk6 sequences, are known in the art. Methods and reagents for preparing recombinant cells are known in the art and are described for cdk6 in the Examples section.

As used herein, the term "putative regulatory compound" refers to compounds having an unknown or previously unappreciated regulatory activity in a particular process. The above-described method for identifying a compound of the present invention includes a step of contacting a test cell (which can be a test cell lysate or a live test cell) with a compound being tested for its ability to increase the expression or biological activity of cdk6. For example, test cells can be grown in liquid culture medium or grown on solid medium in which the liquid medium or the solid medium contains the compound to be tested. In addition, as described above, the liquid or solid medium contains components necessary for cell growth, such as assimilable carbon, nitrogen and micro-nutrients.

The above described methods, in one aspect, involve contacting cells with the compound being tested for a sufficient time to allow for interaction of the putative regulatory compound with an element that affects cdk6 expression and/or biological activity in a cell. Such elements can include, but are not limited to: a nucleic acid molecule encoding cdk6 (including regulatory regions of such a molecule), cdk6 protein, cdk6 inhibitors, cdk6 stimulators, and cdk6 substrates. The period of contact with the compound being tested can be varied depending on the result being measured, and can be determined by one of skill in the art. For example, for binding assays, a shorter time of contact with the compound being tested is typically suitable, than when activity or expression is assessed. As used herein, the term "contact period" refers to the time period during which cells are in contact with the compound being tested. The term "incubation period" refers to the entire time during which cells are allowed to grow prior to evaluation, and can be inclusive of the contact period. Thus, the incubation period includes all of the contact period and may include a further time period during which the compound being tested is not present but during which growth is continuing (in the case of a cell based assay) prior to scoring. The incubation time for growth of cells can vary but is sufficient to allow for the upregulation of cdk6 expression or biological activity in a cell. It will be recognized that shorter incubation times are preferable because compounds can be more rapidly screened. A preferred incubation time is between about 1 hour to about 48 hours.

The conditions under which the cell or cell lysate of the present invention is contacted with a putative regulatory compound, such as by mixing, are any suitable culture or assay conditions and includes an effective medium in which the cell can be cultured or in which the cell lysate can be evaluated in the presence and absence of a putative regulatory compound. Cells of the present invention can be cultured in a variety of containers as including, but not limited to, tissue culture flasks, test tubes, microtiter dishes, and petri plates. Culturing is carried out at a temperature, pH and carbon dioxide content appropriate for the cell. Such culturing conditions are also within the skill in the art. Cells are contacted with a putative regulatory compound under conditions which take into account the number of cells per container contacted, the concentration of putative regulatory compound(s) administered to a cell, the incubation time of the putative regulatory compound with the cell, and the concentration of compound administered to a cell. Determination of effective protocols can be accomplished by those skilled in the art based on variables such as the size of the container, the volume of liquid in the container, conditions known to be suitable for the culture of the particular cell type used in the assay, and the chemical composition of the putative regulatory compound (i.e., size, charge etc.) being tested. A preferred amount of putative regulatory compound(s) comprises between about 1 nM to about 10 mM of putative regulatory compound(s) per well of a 96-well plate.

In one aspect, the present method also makes use of non-cell based assay systems to identify compounds that can regulate cdk6 expression or biological activity and thereby are predicted to be useful for regulating cell growth. For example, cdk6 proteins and nucleic acid molecules encoding cdk6 may be recombinantly expressed and utilized in non-cell based assays to identify compounds that bind to the protein or nucleic acid molecule, respectively. In non-cell based assays the recombinantly expressed cdk6 or nucleic acid encoding cdk6 is attached to a solid substrate such as a test tube, microtitre well or a column, by means well known to those in the art.

In one embodiment, DNA encoding a reporter molecule can be linked to a regulatory element of the cdk6 gene (or a gene encoding a protein that directly regulates cdk6) and used in appropriate intact cells, cell extracts or lysates to identify compounds that modulate cdk6 gene expression, respectively. Appropriate cells or cell extracts are prepared from any cell type that normally expresses cdk6, thereby ensuring that the cell extracts contain the transcription factors required for in vitro or in vivo transcription. The screen can be used to identify compounds that modulate the expression of the reporter construct. In such screens, the level of reporter gene expression is determined in the presence of the test compound and compared to the level of expression in the absence of the test compound.

Following steps (a), (b) and (c) of the present method is a step (d) of selecting a compound that increase the expression or biological activity of cdk6 in the test cell as compared to the initial level of cdk6 expression or biological activity prior to contact with the compound. In other words, compounds which cause an increase in the level of cdk6 expression or biological activity as detected in step (c) and as compared to the level detected in step (a) are selected by the present method as being compounds that are predicted to be useful for the inhibition of cell growth. Preferably, compounds which are selected in step (d) are compounds for which, after the test cell was contacted with the compound in step (b), the level of cdk6 expression or biological activity detected in step (c) was statistically significantly (i.e., with at least a 95% confidence level, or $p<0.05$) increased as compared to the initial level of cdk6 expression or biological activity detected in step (a). Preferably, detection of at least about a 30% increase in ckd6 expression or biological activity in the cell as compared to initial level results in selection of the compound as being useful for inhibition of cell growth. More preferably, detection of at least about a 50% increase and more preferably at least about a 70% increase, and more preferably at least about a 90% increase in cdk6 expression or biological activity in the cell as compared to the initial level results in selection of the compound as being useful for inhibition of cell growth. In one embodiment, a 1.5 fold increase in ckd6 expression or biological activity in the cell as compared to the initial level results in selection of the compound as being useful for inhibition of cell growth. More preferably, detection of at least about a 3 fold increase, and more preferably at least about a 6 fold increase, and even more preferably, at least about a 12 fold increase, and even more preferably, at least about a 24 fold increase in ckd6 expression or biological activity as compared to the initial level, results in selection of the compound as being useful for inhibition of cell growth.

It is to be understood that either of steps (a) and (c) of detection can result in no detection of cdk6 expression or biological activity or detection of cdk6. More specifically, since the level of cdk6 expression or biological activity in step (a) (i.e., the initial level) is the baseline or control level of cdk6 for the assay, if step (a) reveals no detectable cdk6 expression or biological activity, then any detectable level of cdk6 expression or biological activity in step (c) is considered to be a positive result and indicative of increased cdk6 activity in the cell. If the initial level of cdk6 expression or biological activity in step (a) is a detectable level, then the level of cdk6 expression or biological activity detected in step (c) is evaluated to determine whether it is statistically significantly greater than that of step (a). It is possible that the level of cdk6 expression or biological activity in step (c) could be no detectable level, which would indicate that the compound did not increase cdk6 activity. In this scenario, however, it should be determined that the test cell can display an increase in cdk6 expression or biological activity under some conditions (i.e., by contact with a compound known to increase cdk6 activity in the test cell), so that false negatives are not identified.

In one embodiment of this method of the present invention, the method further includes the step of detecting whether the compound selected in step (d) can inhibit cell growth. In this embodiment, the test cell is contacted with the compound as in step (b), and the growth of the cell before and after contact with the cell are evaluated. Evaluation of cell growth can be by any suitable method in the art, including, but not limited to, proliferation assays (e.g., by measuring uptake of [$^3$H]-thymidine, viewing cells morphologically) and/or evaluating markers of cell growth (e.g., measurement of changes in cell surface markers, measurement of intracellular indicators of cell growth). Such methods are known in the art and are exemplified in the Examples section.

In another embodiment of this method of the present invention, the method further includes a step of detecting whether the compound decreases p57KIP2 expression or biological activity in the cell. p57KIP2 is believed to be an inhibitor of cdk6. Therefore, in one embodiment, it is desirable to detect whether the compound inhibits the p57KIP2 inhibitor, so that cdk6 can be released, thereby increasing cdk6 activity. The present inventors have discovered that in T lymphocytes, where cdk6 expression is high, p57KIP2 and cdk6 interact, and p57KIP2 is also present in high amounts. The present inventors have additionally discovered that p57KIP2 is present in very high amounts in normal breast epithelial cells, and although it has not currently been determined whether p57KIP2 in normal breast epithelial cells interacts with cdk6, based on the T lymphocyte data, the present inventors believe that it is likely the cdk6 binds to p57KIP2 in these cells. Without being bound by theory, the present inventors additionally believe that it is possible that p57KIP2 will be found to be reduced in expression in breast epithelial tumor cells. Therefore, p57KIP2 may be a second marker for tumor cell growth in breast tumors (i.e., see the diagnostic method of the present invention described above).

In yet another embodiment of this method, the method further includes the steps of: (e) detecting a level of cdk4 expression in the cell prior to and after contact with the compound; and, (f) selecting a compound that does not substantially increase the expression or biological activity of cdk4 in the cell after contact with the compound as compared to prior to contact with the compound. In this embodiment, the step of detecting a level of cdk4 expression can be performed in substantially the same ways as for detecting cdk6 levels, with the reagents being suitable for the detection of cdk4. Such methods are described in detail in the Examples, and the reagents useful for such detection methods are known in the art. Additionally, the nucleic acid and amino acid sequences for cdk4 are known (See, NCBI Accession No. NM_000075; GenBank® No. 4502734). Preferably, compounds selected by the present method increase the expression and/or biological activity of cdk6, but do not increase the expression and/or biological activity of cdk4. The expression and/or biological activity can remain unchanged as compared to after contact of the cell with the compound or in a preferred embodiment, decreases after contact of the cell with the compound, as compared to the initial cdk4 levels.

Compounds suitable for testing and use in the methods of the present invention include any known or available proteins, nucleic arid molecules, and as well as products of drug design, including peptides, oligonucleotides, carbohydrates and/or synthetic organic molecules. Such an agent can be obtained, for example, from molecular diversity strategies (a combination of related strategies allowing the rapid construction of large, chemically diverse molecule libraries), libraries of natural or synthetic compounds, in particular from chemical or combinatorial libraries (i.e., libraries of compounds that differ in sequence or size but that have the same building blocks) or by rational drug design. See for example, Maulik et al., 1997, *Molecular Biotechnology: Therapeutic Applications and Strategies*, Wiley-Liss, Inc., which is incorporated herein by reference in its entirety. Candidate compounds initially identified by drug design methods can be screened for the ability to increase the expression and/or biological activity of cdk6 using the methods described herein.

In a molecular diversity strategy, large compound libraries are synthesized, for example, from peptides, oligonucleotides, carbohydrates and/or synthetic organic molecules, using biological, enzymatic and/or chemical approaches. The critical parameters in developing a molecular diversity strategy include subunit diversity, molecular size, and library diversity. The general goal of screening such libraries is to utilize sequential application of combinatorial selection to obtain high-affinity ligands against a desired target, and then optimize the lead molecules by either random or directed design strategies. Methods of molecular diversity are described in detail in Maulik, et al., supra.

In a rational drug design procedure, the three-dimensional structure of a regulatory compound can be analyzed by, for example, nuclear magnetic resonance (NMR) or X-ray crystallography. This three-dimensional structure can then be used to predict structures of potential compounds, such as potential regulatory agents by, for example, computer modeling. The predicted compound structure can be used to optimize lead compounds derived, for example, by molecular diversity methods. In addition, the predicted compound structure can be produced by, for example, chemical synthesis, recombinant DNA technology, or by isolating a mimetope from a natural source (e.g., plants, animals, bacteria and fungi).

Various other methods of structure-based drug design are disclosed in Maulik et al., 1997, supra. Maulik et al. disclose, for example, methods of directed design, in which the user directs the process of creating novel molecules from a fragment library of appropriately selected fragments; random design, in which the user uses a genetic or other algorithm to randomly mutate fragments and their combinations while simultaneously applying a selection criterion to evaluate the fitness of candidate ligands; and a grid-based approach in which the user calculates the interaction energy between three dimensional receptor structures and small fragment probes, followed by linking together of favorable probe sites.

Compounds identified by the method described above can be used in a method to regulate cell growth, as described below and any such compounds are encompassed for use in the method described below.

Yet another embodiment of the present invention is a method to regulate cell growth. Such a method includes the step of increasing the expression and/or biological activity of cdk6 in a cell to inhibit growth of the cell. Preferably, the cell in which growth is inhibited is a cell which, prior to the application of the present method, is exhibiting inappropriate cell growth or a potential therefor. Preferred cells to regulate according to the present invention include tumor cells. Particularly preferred cells to regulate according to the present invention are mammary tumor cells. Cells in which it is desirable to inhibit cell growth can be identified, for example, using the method for assessing tumor growth of the present invention as described in detail above. Such a method is particularly useful in patients where increased cell growth is, or predicted to become, problematic. Therefore, such a method is particularly useful to treat patients that have, or are at a risk of developing, tumor cell growth (i.e., a cancer), or to treat any other patients having a condition characterized by undesirable cell growth (e.g., lymphoproliferative disorders). Other diseases and conditions in which inhibition of cell growth would be desirable will be apparent to those of skill in the art and are intended to be encompassed by the present invention.

The method of the present invention includes a step of increasing cdk6 expression and/cr biological activity in a patient that has; or is at risk of developing, inappropriate or unregulated cell growth. Increasing cdk6 expression or biological activity according to the present invention can be accomplished by directly affecting cdk6 expression (transcription or translation) or biological activity, or by directly affecting the ability of a regulator (inhibitor or stimulator) of cdk6 to bind to cdk6 or to activate cdk6. Preferably, the method of the present invention is targeted to a particular type of cell or tissue or region of the body in which inhibition of cell growth is desired. A targeted cell, for example, could include a tumor cell, wherein the method is targeted to tumor cells, and does not affect cdk6 expression or biological activity in non-tumor cells, or in cells of a different type that the tumor cell type. Therefore, the method of the present invention is intended to be specifically targeted to cdk6 expression and/or biological activity for the purpose of inhibiting cell growth by increasing cdk6 expression and/or biological activity.

An increase in cdk6 expression and/or biological activity is defined herein as any measurable (detectable) increase (i.e., upregulation, stimulation, enhancement) of the expression or activity of cdk6. As used herein, to increase cdk6 expression and/or biological activity to inhibit cell growth refers to any measurable increase in cdk6 expression and/or biological activity which results in any measurable inhibition of cell growth in a patient. An increase in cdk6 expression or biological activity can be assessed using the method of the present invention as described above. Preferably, cell growth, or the potential therefor, is inhibited (i.e., decreased, reduced), optimally, to an extent that the animal no longer suffers discomfort and/or altered function resulting from or associated with the inappropriate (i.e., excessive, tumorous) cell growth prior to treatment.

Accordingly, one embodiment of the present invention includes the use of a variety of agents (i.e., regulatory compounds) which, by acting directly on cdk6 (or the gene encoding cdk6) or on inhibitors or stimulators of cdk6, increase the expression and/or biological activity of cdk6 in a cell such that cell growth is reduced in an animal. Agents useful in the present invention include, for example, proteins, nucleic acid molecules, antibodies, and compounds that are products of rational drug design (i.e., drugs). Such compounds can be identified using the method of identifying compounds for regulating cell growth as described above. Moreover, the expression or biological activity of cdk6 in a cell can be determined using the methods described above.

Therefore, in one embodiment, the method of the present invention increases the transcription and/or the translation of cdk6 by a cell in the patient that naturally expresses cdk6 and that is the target for growth regulation. Methods for increasing the expression of cdk6 include, but are not limited to, administering an agent that increases the expression, and overexpressing cdk6 in the target cells of the patient. In one aspect of this embodiment, cdk6 can be effectively overexpressed in a cell by increasing the activity of a cdk6 gene promoter in the cell such that expression of endogenous cdk6 in the cell is increased. For example, the activity of the cdk6 gene promoter can be increased by methods which include, contacting the promoter with a transcriptional activator, inhibiting a cdk6 inhibitor, such as members of the CIP/KIP and INK4 families of CDKI's (e.g., p57KIP2, p16Ink4A), and increasing the activity of a cdk6 stimulator, such as cyclin D family members (D1, D2 and D3). Methods by which such compounds (e.g., transcriptional activators) can be administered to a cell are described below.

In one aspect of this embodiment of the present invention, the expression and/or biological activity of cdk6 is increased by overexpressing cdk6 in the cell in which growth is to be regulated. Overexpression of cdk6 refers to an increase in expression of cdk6 over a normal, endogenous level of cdk6 expression. For some cell types, which do not express detectable levels of cdk6 under normal conditions, such expression can be any detectable level. For cell types which do express detectable levels of cdk6 under normal conditions, an overexpression is any statistically significant increase in expression of cdk6 ($p<0.05$) (or constitutive expression where expression is normally not constitutive) over endogenous levels of expression. One method by which cdk6 overexpression can be achieved is by transfecting the cell with a recombinant nucleic acid molecule encoding cdk6 operatively linked to a transcription control sequence, wherein the recombinant cdk6 is expressed by the cell. This method has been exemplified in the Examples section. As discussed previously herein, the nucleic acid sequence encoding cdk6, vectors suitable for expressing such a molecule, and methods of transfection of a cell with such a molecule, including in vivo methods, are known and are described in detail below.

A recombinant nucleic acid molecule expressing cdk6 is a molecule that can include at least one of any nucleic acid sequence encoding a protein having cdk6 biological activity operatively linked to at least one of any transcription control sequence capable of effectively regulating expression of the nucleic acid molecule(s) in the cell to be transfected, examples of which are disclosed herein. Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably, especially with respect to a nucleic acid molecule, or a nucleic acid sequence, being capable of encoding a protein. In addition, the phrase "recombinant molecule" primarily refers to a nucleic acid molecule operatively linked to a transcription control sequence, but can be used interchangeably with the phrase "nucleic acid molecule" which is administered to an animal.

Preferably, a recombinant nucleic acid molecule is produced using recombinant DNA technology (e.g., polymerase chain reaction (PCR) amplification, cloning). Suitable nucleic acid sequences encoding cdk6 for use in a recombinant nucleic acid molecule of the present invention include any nucleic acid sequence that encodes a cdk6 having cdk6 biological activity and suitable for use in the target host cell. For example, when the target host cell is a human cell, human cdk6-encoding nucleic acid sequences are preferably used, although the present invention is not limited to strict use of naturally occurring sequences or same-species sequences. One example of a nucleic acid sequence encoding a biologically active cdk6 protein is described in the Examples section.

Knowing the nucleic acid sequences of certain nucleic acid molecules of the present invention allows one skilled in the art to, for example, (a) make copies of those nucleic acid molecules and/or (b) obtain nucleic acid molecules including at least a portion of such nucleic acid molecules (e.g., nucleic acid molecules including full-length genes, full-length coding regions, regulatory control sequences, truncated coding regions). Such nucleic acid molecules can be obtained in a variety of ways including traditional cloning techniques using oligonucleotide probes to screen appropriate libraries or DNA and PCR amplification of appropriate libraries or DNA using oligonucleotide primers. Preferred libraries to screen or from which to amplify nucleic acid molecule include mammalian genomic DNA libraries. Techniques to clone and amplify genes are disclosed, for example, in Sambrook et al., ibid.

A recombinant nucleic acid molecule includes a recombinant vector, which is any nucleic acid sequence, typically a heterologous sequence, which is operatively linked to the isolated nucleic acid molecule encoding a cdk6 protein, which is capable of enabling recombinant production of the cdk6 protein, and which is capable of delivering the nucleic acid molecule into a host cell according to the present invention. Such a vector can contain nucleic acid sequences that are not naturally found adjacent to the isolated nucleic acid molecules to be inserted into the vector. The vector can be either RNA or DNA, either prokaryotic or eukaryotic, and preferably in the present invention, is a virus or a plasmid. Recombinant vectors can be used in the cloning, sequencing, and/or otherwise manipulating of nucleic acid molecules. Recombinant vectors are preferably used in the expression of nucleic acid molecules, and can also be referred to as expression vectors. Preferred recombinant vectors are capable of being expressed in a transfected host cell, and particularly, in a transfected mammalian host cell in vivo.

In a recombinant molecule of the present invention, nucleic acid molecules are operatively linked to expression vectors containing regulatory sequences such as transcription control sequences, translation control sequences, origins of replication, and other regulatory sequences that are compatible with the host cell and that control the expression of nucleic acid molecules of the present invention. In particular, recombinant molecules of the present invention include nucleic acid molecules that are operatively linked to one or more transcription control sequences. The phrase "operatively linked" refers to linking a nucleic acid molecule to a transcription control sequence in a manner such that the molecule is able to be expressed when transfected (i.e., transformed, transduced or transfected) into a host cell.

Transcription control sequences are sequences which control the initiation, elongation, and termination of transcription. Particularly important transcription control sequences are those which control transcription initiation, such as promoter, enhancer, operator and repressor sequences. Suitable transcription control sequences include any transcription control sequence that can function in a host cell according to the present invention. A variety of suitable transcription control sequences are known to those skilled in the art. Preferred transcription control sequences include those which function in mamialian cells, with cell- or tissue-specific transcription control sequences being particularly preferred. Examples of preferred transcription control sequences include, but are not limited to, transcription control sequences useful for expression of a protein in breast epithelial cells and tumor cells and the naturally occurring cdk6 promoter. Particularly preferred transcription control sequences include inducible promoters, cell-specific promoters, tissue-specific promoters (e.g., insulin promoters) and enhancers. Suitable promoters for these and other cell types will be easily determined by those of skill in the art. Transcription control sequences of the present invention can also include naturally occurring transcription control sequences naturally associated with the protein to be expressed prior to isolation. In one embodiment, a transcription control sequence includes an inducible promoter.

One type of recombinant vector useful in a recombinant nucleic acid molecule of the present invention is a recombinant viral vector. Such a vector includes a recombinant nucleic acid sequence encoding a cdk6 protein of the present invention that is packaged in a viral coat that can be expressed in a host cell in an animal or ex vivo after administration. A number of recombinant viral vectors can be used, including, but not limited to, those based on alphaviruses, poxviruses, adenoviruses, herpesviruses, lentiviruses, adeno-associated viruses and retroviruses. Particularly preferred viral vectors are those based on adenoviruses and adeno-associated viruses. Viral vectors suitable for gene delivery are well known in the art and can be selected by the skilled artisan for use in the present invention. A detailed discussion of current viral vectors is provided in "Molecular Biotechnology," Second Edition, by Glick and Pasternak, ASM Press, Washington D.C., 1998, pp. 555–590, the entirety of which is incorporated herein by reference.

For example, a retroviral vector, which is useful when it is desired to have a nucleic acid sequence inserted into the host genome for long term expression, can be packaged in the envelope protein of another virus so that it has the binding specificity and infection spectrum that are determined by the envelope protein (e.g., a pseudotyped virus). In addition, the envelope gene can be genetically engineered to include a DNA element that encodes and amino acid sequence that binds to a cell receptor to create a recombinant retrovirus that infects a specific cell type. Expression of the gene (i.e., the cdk6 gene) can be further controlled by the use of a cell or tissue-specific promoter. Retroviral vectors have been successfully used to transfect cells with a gene which is expressed and maintained in a variety of ex vivo systems An adenoviral vector is a preferred vector for use in the present method. An adenoviral vector infects a wide range of human cells and has been used extensively in live vaccines. Adenoviral vectors used in gene therapy do not integrate into the host genome, and therefore, gene therapy using this system requires periodic administration, although methods have been described which extend the expression time of adenoviral transferred genes, such as administration of antibodies directed against T cell receptors at the site of expression (Sawchuk et al., 1996, *Hum. Gene. Ther.* 7:499–506). The efficiency of adenovirus-mediated gene delivery can be enhanced by developing a virus that preferentially infects a particular target cell. For example, a gene for the attachment fibers of adenovirus can be engineered to include a DNA element that encodes a protein domain that binds to a cell-specific receptor. Examples of successful in vivo delivery of genes has been demonstrated and is discussed in more detail below.

Yet another type of viral vector is based on adeno-associated viruses, which are small, nonpathogenic, single-stranded human viruses. This virus can integrate into a specific site on chromosome 19. This virus can carry a cloned insert of about 4.5 kb, and has typically been successfully used to express proteins in vivo from 70 days to at least 5 months. Demonstrating that the art is quickly advancing in the area of gene therapy, however, a recent publication by Bennett et al. reported efficient and stable transgene expression by adeno-associated viral vector transfer in vivo for greater than 1 year (Bennett et al., 1999, *Proc. Natl. Acad. Sci. USA* 96:9920–9925).

Another type of viral vector that is suitable for use in the present invention is a herpes simplex virus vector. Herpes simplex virus type 1 infects and persists within nondividing neuronal cells, and is therefore a suitable vector for targeting and transfecting cells of the central and peripheral nervous system with a cdk6 protein of the present invention. Preclinical trials in experimental animal models with such a vector has demonstrated that the vector can deliver genes to cells of both the brain and peripheral nervous system that are expressed and maintained for long periods of time.

Suitable host cells to transfect with a recombinant nucleic acid molecule according to the present invention include any mammalian cell that can be transfected. Host cells can be either untransfected cells or cells that are already transfected with at least one nucleic acid molecule. Host cells according to the present invention can be any cell capable of producing a cdk6 protein as described herein. A preferred host cell includes any mammalian cell, and more preferably, mammalian mammary epithelial cells, tumor cells, fibroblasts, and lymphocytes.

According to the present invention, a host cell can also be referred to as a target cell or a targeted cell in vivo, in which a recombinant nucleic acid molecule encoding a cdk6 protein having cdk6 biological activity is to be expressed. As used herein, the term "target cell" or "targeted cell" refers to a cell to which a recombinant nucleic acid molecule of the present invention is selectively designed to be delivered. The term target cell does not necessarily restrict the delivery of a recombinant nucleic acid molecule only to the target cell and no other cell, but indicates that the delivery of the recombinant molecule, the expression of the recombinant molecule, or both, are specifically directed to a preselected host cell. Targeting delivery vehicles, including liposomes and viral vector systems are known in the art. For example, a liposome can be directed to a particular target cell or tissue by using a targeting agent, such as an antibody, soluble receptor or ligand, incorporated with the liposome, to target a particular cell or tissue to which the targeting molecule can bind. Targeting liposomes are described, for example, in Ho et al., 1986, *Biochemistry* 25: 5500–6; Ho et al., 1987a, *J Biol Chem* 262: 13979–84; Ho et al., 1987b, *J Biol Chem* 262: 13973–8; and U.S. Pat. No. 4,957,735 to Huang et al., each of which is incorporated herein by reference in its entirety). Ways in which viral vectors can be modified to deliver a nucleic acid molecule to a target cell have been discussed above. Alternatively, the route of administration, as discussed below, can be used to target a specific cell or tissue. For example, intracoronary administration of an adenoviral vector has been show.,n to be effective for the delivery of a gene cardiac myocytes (Maurice et al., 1999, *J. Clin. Invest.* 104:21–29). Intravenous delivery of cholesterol-containing cationic liposomes has been shown to preferentially target pulmonary tissues (Liu et al., *Nature Biotechnology* 15:167, 1997), and effectively mediate transfer and expression of genes in vivo. Other examples of successful targeted in vivo delivery of nucleic acid molecules are known in the art. Finally, a recombinant nucleic acid molecule can be selectively (i.e., preferentially, substantially exclusively) expressed in a target cell by selecting a transcription control sequence, and preferably, a promoter, which is selectively induced in the target cell and remains substantially inactive in non-target cells.

According to the method of the present invention, a host cell is preferably transfected in vivo (i.e., in a mammal) as a result of administration to a mammal of a recombinant nucleic acid molecule, or ex vivo, by removing cells from a mammal and transfecting the cells with a recombinant nucleic acid molecule ex vivo. Transfection of a nucleic acid molecule into a host cell according to the present invention can be accomplished by any method by which a nucleic acid molecule administered into the cell in vivo, and includes, but is not limited to, transfection, electroporation, microinjection, lipofection, adsorption, viral infection, naked DNA injection and protoplast fusion. Methods of administration are discussed in detail below.

It may be appreciated by one skilled in the art that use of recombinant DNA technologies can improve expression of transfected nucleic acid molecules by manipulating, for example, the duration of expression of the gene (i.e., recombinant nucleic acid molecule), the number of copies of the nucleic acid molecules within a host cell, the efficiency with which those nucleic acid molecules are transcribed, the efficiency with which the resultant transcripts are translated, and the efficiency of post-translational modifications. Recombinant techniques useful for increasing the expression of nucleic acid molecules of the present invention include, but are not limited to, operatively linking nucleic acid molecules to high-copy number plasmids, integration of the nucleic acid molecules into one or more host cell chromosomes, addition of vector stability sequences to plasmids, increasing the duration of expression of the recombinant molecule, substitutions or modifications of transcription control signals (e.g., promoters, operators, enhancers), substitutions or modifications of translational control signals (e.g., ribosome binding sites, Shine-Dalgarno sequences), modification of nucleic acid molecules of the present invention to correspond to the codon usage of the host cell, and deletion of sequences that destabilize transcripts. The activity of an expressed recombinant protein of the present invention may be improved by fragmenting, modifying, or derivatizing nucleic acid molecules encoding such a protein.

In one embodiment of the present invention, a recombinant nucleic acid molecule of the present invention is administered to a patient in a liposome delivery vehicle, whereby the nucleic acid sequence encoding the cdk6 protein enters the host cell (i.e., the target cell) by lipofection. A liposome delivery vehicle contains the recombinant nucleic acid molecule and delivers the molecules to a suitable site in a host recipient. According to the present invention, a liposome delivery vehicle comprises a lipid composition that is capable of delivering a recombinant nucleic acid molecule of the present invention, including both plasmids and viral vectors, to a suitable cell and/or tissue in a patient. A liposome delivery vehicle of the present invention comprises a lipid composition that is capable of fusing with the plasma membrane of the target cell to deliver the recombinant nucleic acid molecule into a cell.

A liposome delivery vehicle of the present invention can be modified to target a particular site in a mammal (i.e., a targeting liposome), thereby targeting and making use of a nucleic acid molecule of the present invention at that site. Suitable modifications include manipulating the chemical formula of the lipid portion of the delivery vehicle. Manipulating the chemical formula of the lipid portion of the delivery vehicle can elicit the extracellular or intracellular targeting of the delivery vehicle. For example, a chemical can be added to the lipid formula of a liposome that alters the charge of the lipid bilayer of the liposome so that the liposome fuses with particular cells having particular charge characteristics. Other targeting mechanisms include targeting a site by addition of exogenous targeting molecules (i.e., targeting agents) to a liposome (e.g., antibodies, soluble receptors or ligands).

A liposome delivery vehicle is preferably capable of remaining stable in a patient for a sufficient amount of time to deliver a nucleic acid molecule of the present invention to a preferred site in the patient (i.e., a target cell). A liposome delivery vehicle of the present invention is preferably stable in the patient into which it has been administered for at least about 30 minutes, more preferably for at least about 1 hour and even more preferably for at least about 24 hours. A preferred liposome delivery vehicle of the present invention is from about 0.01 microns to about 1 microns in size.

Suitable liposomes for use with the present invention include any liposome. Preferred liposomes of the present invention include those liposomes commonly used in, for example, gene delivery methods known to those of skill in the art. Preferred liposome delivery vehicles comprise multilamellar vesicle (MLV) lipids and extruded lipids. Methods for preparation of MLV's are well known in the art and are described, for example, in the Examples section. According to the present invention, "extruded lipids" are lipids which are prepared similarly to MLV lipids, but which are subsequently extruded through filters of decreasing size, as described in Templeton et al., 1997, *Nature Biotech.*, 15:647–652, which is incorporated herein by reference in its entirety. Small unilamellar vesicle (SUV) lipids can also be used in the composition and method of the present invention. In one embodiment, liposome delivery vehicles comprise liposomes having apolycationic lipid composition (i.e., cationic liposomes) and/or liposomes having a cholesterol backbone conjugated to polyethylene glycol. In a preferred embodiment, liposome delivery vehicles useful in the present invention comprise one or more lipids selected from the group of DOTMA, DOTAP, DOTIM, DDAB, and cholesterol.

Preferably, the transfection efficiency of a nucleic acid:liposome complex of the present invention is at least about 1 picogram (pg) of protein expressed per milligram (mg) of total tissue protein per microgram (μg) of nucleic acid delivered. More preferably, the transfection efficiency of a nucleic acid:liposome complex of the present invention is at least about 10 pg of protein expressed per mg of total tissue protein per μg of nucleic acid delivered; and even more preferably, at least about 50 pg of protein expressed per mg of total tissue protein per μg of nucleic acid delivered; and most preferably, at least about 100 pg of protein expressed per mg of total tissue protein per μg of nucleic acid delivered.

Complexing a liposome with a nucleic acid molecule of the present invention can be achieved using methods standard in the art. A suitable concentration of a nucleic acid molecule of the present invention to add to a liposome includes a concentration effective for delivering a sufficient amount of recombinant nucleic acid molecule into a target cell of a patient such that the cdk6 protein encoded by the nucleic acid molecule can be expressed in a an amount effective to inhibit the growth of the target cell. Preferably, from about 0.1 µg to about 10 µg of nucleic acid molecule of the present invention is combined with about 8 nmol liposomes. In one embodiment, the ratio of nucleic acids to lipids (µg nucleic acid:nmol lipids) in a composition of the present invention is preferably at least from about 1:10 to about 6:1 nucleic acid:lipid by weight (i.e., 1:10=1 µg nucleic acid:10 nmol lipid).

According to the present invention, a regulatory compound for increasing the expression or biological activity of cdk6, including a recombinant nucleic acid molecule encoding cdk6, is typically administered to a patient in a composition. In addition to the recombinant nucleic acid molecule or other cdk6 regulatory compound (i.e., a protein, antibody, carbohydrate, small molecule product of drug design), the composition can include, for example, a pharmaceutically acceptable carrier, which includes pharmaceutically acceptable excipients and/or delivery vehicles, for delivering the recombinant nucleic acid molecule or other regulatory compound to a patient (e.g., a liposome delivery vehicle). As used herein, a pharmaceutically acceptable carrier refers to any substance suitable for delivering a therapeutic composition useful in the method of the present invention to a suitable in vivo or ex vivo site. Preferred pharmaceutically acceptable carriers are capable of maintaining a recombinant nucleic acid molecule of the present invention in a form that, upon arrival of the nucleic acid molecule to a target cell, the nucleic acid molecule is capable of entering the cell and being expressed by the cell. Suitable excipients of the present invention include excipients or formularies that transport or help transport, but do not specifically target a nucleic acid molecule to a cell (also referred to herein as non-targeting carriers). Examples of pharmaceutically acceptable excipients include, but are not limited to water, phosphate buffered saline, Ringer's solution, dextrose solution, serum-containing solutions, Hank's solution, other aqueous physiologically balanced solutions, oils, esters and glycols. Aqueous carriers can contain suitable auxiliary substances required to approximate the physiological conditions of the recipient, for example, by enhancing chemical stability and isotonicity.

Suitable auxiliary substances include, for example, sodium acetate, sodium chloride, sodium lactate, potassium chloride, calcium chloride, and other substances used to produce phosphate buffer, Tris buffer, and bicarbonate buffer. Auxiliary substances can also include preservatives, such as thimerosal, m- or o-cresol, formalin and benzol alcohol. Compositions of the present invention can be sterilized by conventional methods and/or lyophilized.

One type of pharmaceutically acceptable carrier includes a controlled release formulation that is capable of slowly releasing a composition of the present invention into an animal. As used herein, a controlled release formulation comprises recombinant nucleic acid molecule or other cdk6 regulatory compound of the present invention in a controlled release vehicle. Suitable controlled release vehicles include, but are not limited to, biocompatible polymers, other polymeric matrices, capsules, microcapsules, microparticles, bolus preparations, osmotic pumps, diffusion devices, liposomes, liposphures, and transdermal delivery systems. Suitable delivery vehicles have been previously described herein, and include, but are not limited to liposomes, viral vectors or other delivery vehicles, including ribozymes. Natural lipid-containing delivery vehicles include cells and cellular membranes. Artificial lipid-containing delivery vehicles include liposomes and micelles. As discussed above, a delivery vehicle of the present invention can be modified to target to a particular site in a patient, thereby targeting and making use of a nucleic acid molecule at that site. Suitable modifications include manipulating the chemical formula of the lipid portion of the delivery vehicle and/or introducing into the vehicle a targeting agent capable of specifically targeting a delivery vehicle to a preferred site, for example, a preferred cell type. Other suitable delivery vehicles include gold particles, poly-L-lysine/DNA-molecular conjugates, and artificial chromosomes.

As discussed above, a composition of the present invention is administered to a patient in a manner effective to deliver the recombinant nucleic acid molecule comprising a nucleic acid sequence encoding a cdk6 protein having cdk6 biological activity to a target cell, whereby the target cell is transfected by the recombinant molecule and whereby the cdk6 protein is expressed in the target cell. When another cdk6 regulatory compound is to be delivered to a target cell in a patient, the composition is administered in a manner effective to deliver the cdk6 regulatory compound to the target cell, whereby the compound can act on the cell (e.g., enter the cell and act on cdk6 or an inhibitor or stimulator thereof) so that cdk6 expression or biological activity is increased. Suitable administration protocols include any in vivo or ex vivo administration protocol.

According to the present invention, an effective administration protocol (i.e., administering a composition of the present invention in an effective manner) comprises suitable dose parameters and modes of administration that result in transfection and expression of a recombinant nucleic acid molecule encoding a cdk6 protein or an other cdk6 regulatory compound, in a target cell of a patient, and subsequent inhibition of the growth of the target cell, preferably so that the patient obtains some measurable, observable or perceived benefit from such administration. In some situations, where the target cell population is accessible for sampling, effective dose parameters can be determined using methods as described herein for assessment of tumor growth. Such methods include removing a sample of the target cell population from the patient prior to and after the recombinant nucleic acid molecule is administered, and measuring changes in cdk6 expression or biological activity, as well as measuring inhibition of the cell. Alternatively, effective dose parameters can be determined by experimentation using in vitro cell cultures, in vivo animal models, and eventually, clinical trials if the patient is human. Effective dose parameters can be determined using methods standard in the art for a particular disease or condition that the patient has or is at risk of developing. Such methods include, for example, determination of survival rates, side effects (i.e., toxicity) and progression or regression of disease.

According to the present invention, suitable methods of administering a composition comprising a recombinant nucleic acid molecule of the present invention to a patient include any route of in vivo administration that is suitable for delivering a recombinant nucleic acid molecule into a patient. The preferred routes of administration will be apparent to those of skill in the art, depending on the type of delivery vehicle used, the target cell population, and the disease or condition experienced by the patient. Preferred methods of in vivo administration include, but are not limited to, intravenous administration, intraperitoneal administration, intramuscular administration, intracoronary administration, intraarterial administration (e.g., into a carotid artery), subcutaneous administration, transdermal delivery, intratracheal administration, subcutaneous administration, intraarticular administration, intraventricular administration, inhalation (e.g., aerosol), intracerebral, nasal, oral, pulmonary administration, impregnation of a catheter, and direct injection into a tissue. In an embodiment where the target cells are in or near a tumor, a preferred route of administration is by direct injection into the tumor or tissue surrounding the tumor. For example, when the tumor is a breast tumor, the preferred methods of administration include impregnation of a catheter, and direct injection into the tumor.

Intravenous, intraperitoneal, and intramuscular administrations can be performed using methods standard in the art. Aerosol (inhalation) delivery can also be performed using methods standard in the art (see, for example, Stribling et al., *Proc. Natl. Acad. Sci. USA* 189:11277–11281, 1992, which is incorporated herein by reference in its entirety). Oral delivery can be performed by complexing a therapeutic composition of the present invention to a carrier capable of withstanding degradation by digestive enzymes in the gut of an animal. Examples of such carriers, include plastic capsules or tablets, such as those known in the art.

One method of local administration is by direct injection. Direct injection techniques are particularly useful for administering a recombinant nucleic acid molecule to a cell or tissue that is accessible by surgery, and particularly, on or near the surface of the body. Administration of a composition locally within the area of a target cell refers to injecting the composition centimeters and preferably, millimeters from the target cell or tissue.

Various methods of administration and delivery vehicles disclosed herein have been shown to be effective for delivery of a nucleic acid molecule to a target cell, whereby the nucleic acid molecule transfected the cell and was expressed. In many studies, successful delivery and expression of a heterologous gene was achieved in preferred cell types and/or using preferred delivery vehicles and routes of administration of the present invention. All of the publications discussed below and elsewhere herein with regard to gene delivery and delivery vehicles are incorporated herein by reference in their entirety. For example, using liposome delivery, U.S. Pat. No. 5,705,151, issued Jan. 6, 1998, to Dow et al. demonstrated the successful in vivo intravenous delivery of a nucleic acid molecule encoding a superantigen and a nucleic acid molecule encoding a cytokine in a cationic liposome delivery vehicle, whereby the encoded proteins were expressed in tissues of the animal, and particularly in pulmonary tissues. Dow et al. also demonstrated successful in vivo delivery of a nucleic acid molecule by direct injection into a site of a tumor. As discussed above, Liu et al., 1997, ibid. demonstrated that intravenous delivery of cholesterol-containing cationic liposomes containing genes preferentially targets pulmonary tissues and effectively mediates transfer and expression of the genes in vivo. Several publications by Dzau and collaborators demonstrate the successful in vivo delivery and expression of a gene into cells of the heart, including cardiac myocytes and fibroblasts and vascular smooth muscle cells using both naked DNA and Hemagglutinating virus of Japan-liposome delivery, administered by both incubation within the pericardium and infusion into a coronary artery (intracoronary delivery) (See, for example, Aoki et al., 1997, *J. Mol. Cell, Cardiol.* 29:949–959; Kaneda et al., 1997, *Ann N.Y. Acad. Sci.* 811:299–308; and von der Leyen et al., 1995, *Proc Natl Acad Sci USA* 92:1137–1141).

As discussed above, delivery of numerous nucleic acid sequences has been accomplished by administration of viral vectors encoding the nucleic acid sequences. Using such vectors, successful delivery and expression has been achieved using ex vivo delivery (See, of many examples, retroviral vector; Blaese et al., 1995, *Science* 270:475–480; Bordignon et al., 1995, *Science* 270:470–475), nasal administration (CFTR-adenovirus-associated vector), intracoronary administration (adenoviral vector and Hemagglutinating virus of Japan, see above), intravenous administration (adeno-associated viral vector; Koeberl et al., 1997, *Proc Natl Acad Sci USA* 94:1426–1431). A publication by Maurice et al., 1999, ibid. demonstrated that an adenoviral vector encoding a $\beta$2-adrenergic receptor, administered by intracoronary delivery, resulted in diffuse multichamber myocardial expression of the gene in vivo, and subsequent significant increases in hemodynamic function and other improved physiological parameters. Levine et al. describe in vitro, ex vivo and in vivo delivery and expression of a gene to human adipocytes and rabbit adipocytes using an adenoviral vector and direct injection of the constructs into adipose tissue (Levine et al., 1998, *J. Nutr. Sci. Vitaminol.* 44:569–572).

In the area of neuronal gene delivery, multiple successful in vivo gene transfers have been reported. Millecamps et al. reported the targeting of adenoviral vectors to neurons using neuron restrictive enhancer elements placed upstream of the promoter for the transgene (phosphoglycerate promoter). Such vectors were administered to mice and rats intramuscularly and intracerebrally, respectively, resulting in successful neuronal-specific transfection and expression of the transgene in vivo (Millecamps et al., 1999, *Nat. Biotechnol.* 17:865–869). As discussed above, Bennett et al. reported the use of adeno-associated viral vector to deliver and express a gene by subretinal injection in the neural retina in vivo for greater than 1 year (Bennett, 1999, ibid.).

Gene delivery to synovial lining cells and articular joints has had similar successes. Oligino and colleagues report the use of a herpes simplex viral vector which is deficient for the immediate early genes, ICP4, 22 and 27, to deliver and express two different receptors in synovial lining cells in vivo (Oligino et al., 1999, *Gene Ther.* 6:1713–1720). The herpes vectors were administered by intraarticular injection. Kuboki et al. used adenoviral vector-mediated gene transfer and intraarticular injection to successfully and specifically express a gene in the temporomandibular joints of guinea pigs in vivo (Kuboki et al., 1999, *Arch. Oral. Biol.* 44:701–709). Apparailly and colleagues systemically administered adenoviral vectors encoding IL-10 to mice and demonstrated successful expression of the gene product and profound therapeutic effects in the treatment of experimentally induced arthritis (Apparailly et al., 1998, *J. Immunol.* 160:5213–5220). In another study, murine leukemia virus-based retroviral vector was used to deliver (by intraarticular injection) and express a human growth hormone gene both ex vivo and in vivo (Ghivizzani et al., 1997, *Gene Ther.* 4:977–982). This study showed that expression by in vivo gene transfer was at least equivalent to that of the ex vivo gene transfer. As discussed above, Sawchuk et al. has reported successful in vivo adenoviral vector delivery of a gene by intraarticular injection, and prolonged expression of the gene in the synovium by pretreatment of the joint with anti-T cell receptor monoclonal antibody (Sawchuk et al., 1996, ibid. Finally, it is noted that ex vivo gene transfer of human interleukin-1 receptor antagonist using a retrovirus has produced high level intraarticular expression and therapeutic efficacy in treatment of arthritis, and is now entering FDA approved human gene therapy trials (Evans and Robbins, 1996, *Curr. Opin. Rheumatol.* 8:230–234). Therefore, the state of the art in gene therapy has led the FDA to consider human gene therapy an appropriate strategy for the treatment of at least arthritis. Taken together, all of the above studies in gene therapy indicate that delivery and expression of a cdk6 encoding recombinant nucleic acid molecule according to the present invention is feasible.

Another method of delivery of recombinant molecules is in a non-targeting carrier (e.g., as "naked" DNA molecules, such as is taught, for example in Wolff et al., 1990, *Science* 247, 1465–1468). Such recombinant nucleic acid molecules are typically injected by direct or intramuscular administration. Recombinant nucleic acid molecules to be administered by naked DNA administration include a nucleic acid molecule of the present invention, and preferably includes a recombinant molecule of the present invention that preferably is replication, or otherwise amplification, competent. A naked nucleic acid reagent of the present invention can comprise one or more nucleic acid molecule of the present invention in the form of, for example, a dicistronic recombinant molecule. Naked nucleic acid delivery can include intramuscular, subcutaneous, intradermal, transdermal, intranasal and oral routes of administration, with direct injection into the target tissue being most preferred. A preferred single dose of a naked nucleic acid vaccine ranges from about 1 nanogram (ng) to about 100 µg, depending on the route of administration and/or method of delivery, as can be determined by those skilled in the art. Suitable delivery methods include, for example, by injection, as drops, aerosolized and/or topically. In one embodiment, pure DNA constructs cover the surface of gold particles (1 to 3 µm in diameter) and are propelled into skin cells or muscle with a "gene gun."

In accordance with the present invention, a suitable single dose of a recombinant nucleic acid molecule encoding a cdk6 protein as described herein is a dose that is capable of transfecting a host cell and being expressed in the host cell at a level sufficient, in the absence of the addition of any other factors or other manipulation of the host cell, to inhibit the growth of the host cell when administered one or more times over a suitable time period. Doses can vary depending upon the cell type being targeted, the route of administration, the delivery vehicle used, and the disease or condition being treated.

In one embodiment, an appropriate single dose of a nucleic acid:liposome complex of the present invention is from about 0.1 µg to about 100 µg per kg body weight of the patient to which the complex is being administered. In another embodiment, an appropriate single dose is from about 1 µg to about 10 µg per kg body weight. In another embodiment, an appropriate single dose of nucleic acid:lipid complex is at least about 0.1 µg of nucleic acid, more preferably at least about 1 µg of nucleic acid, even more preferably at least about 10 µg of nucleic acid, even more preferably at least about 50 µg of nucleic acid, and even more preferably at least about 100 µg of nucleic acid.

Preferably, an appropriate single dose of a recombinant nucleic acid molecule encoding a cdk6 protein of the present invention results in at least about 1 pg of protein expressed per mg of total tissue protein per µg of nucleic acid delivered. More preferably, an appropriate single dose is a dose which results in at least about 10 pg of protein expressed per mg of total tissue protein per µg of nucleic acid delivered; and even more preferably, at least about 50 pg of protein expressed per mg of total tissue protein per µg of nucleic acid delivered; and most preferably, at least about 100 pg of protein expressed per mg of total tissue protein per µg of nucleic acid delivered.

When the cdk6 regulatory agent is a protein, small molecule (i.e., the products of drug design) or antibody, a preferred single dose of such a compound typically comprises between about 0.01 microgram×kilograms$^{-1}$ and about 10 milligram×kilogram$^{-1}$ body weight of an animal. A more preferred single dose of an agent comprises between about 1 microgram×kilograms$^{-1}$ and about 10 milligram× kilograms body weight of an animal. An even more preferred single dose of an agent comprises between about 5 microgram×kilogram$^{-1}$ and about 7 milligram×kilogram$^{-1}$ body weight of an animal. An even more preferred single dose of an agent comprises between about 10 microgram× kilogram$^{-1}$ and about 5 milligram×kilogram$^{-1}$ body weight of an animal. Another particularly preferred lo single dose of an agent comprises between about 0.1 microgram×kilogram$^{-1}$ and about 10 microgram×kilogram$^{-1}$ body weight of an animal, if the agent is delivered parenterally.

Compositions of the present invention can be administered to any mammalian patient, and preferably to humans. According to the present invention, administration of a composition is useful to inhibit cell growth of a target cell. Typically, it is desirable to inhibit the growth of a target cell to obtain a therapeutic benefit in the patient. Patients whom are suitable candidates for the method of the present invention include, but are not limited to, patients that have, or are at risk of developing (e.g., are predisposed to), cancer or a lymphoproliferative disease. Increasing cdk6 expression or biological activity to inhibit cell growth in the absence of obtaining some therapeutic benefit is useful for the purposes of determining factors involved (or not involved) in a disease and preparing a patient to more beneficially receive another therapeutic composition. In a preferred embodiment, however, the methods of the present invention are directed to the inhibition of growth of a target cell which is useful in providing some therapeutic benefit to a patient. As such, a therapeutic benefit is not necessarily a cure for a particular disease or condition, but rather, preferably encompasses a result which most typically includes alleviation of the disease or condition, elimination of the disease or condition, reduction of a symptom associated with the disease or condition, prevention or alleviation of a secondary disease or condition resulting from the occurrence of a primary disease or condition (e.g., metastatic tumor growth resulting from a primary cancer), and/or prevention of the disease or condition. As used herein, the phrase "protected from a disease" refers to reducing the symptoms of the disease; reducing the occurrence of the disease, and/or reducing the severity of the disease. Protecting a patient can refer to the ability of a composition of the present invention, when administered to a patient, to prevent a disease from occurring and/or to cure or to alleviate disease symptoms, signs or causes. As such, to protect a patient from a disease includes both preventing disease occurrence (prophylactic treatment) and treating a patient that has a disease (therapeutic treatment). In particular, protecting a patient from a disease is accomplished by inhibiting the growth of a target cell in the patient by increasing cdk6 expression or biological activity such that a beneficial effect is obtained. A beneficial effect can easily be assessed by one of ordinary skill in the art and/or by a trained clinician who is treating the patient. The term, "disease" refers to any deviation from the normal health of a mammal and includes a state when disease symptoms are present, a, well as conditions in which a deviation (e.g., infection, gene mutation, genetic defect, etc.) has occurred, but symptoms are not yet manifested.

In one aspect of this embodiment of the present invention, the method further includes the step of inhibiting the expression or biological activity of cdk4 in the cell of the patient. The methods for inhibiting the expression or biological activity of cdk4, include, but are not limited to, administration of an agent to the animal that directly inhibits cdk4 expression or biological activity. Such agents include, but are not limited to: a ribozyme that is specific for cdk4 RNA; a DNA binding protein or a drug that binds to a gene encoding cdk4 and inhibits expression of cdk4; a protein or drug that binds to cdk4 intracellularly and prevents the biological activity of the cdk4; and, an isolated nucleic acid molecule that reduces expression of cdk4 by hybridizing under high stringency conditions to a gene encoding cdk4 in a cell of the animal (i.e., an anti-sense nucleic acid molecule). Ribozymes, DNA binding proteins, drugs, and antisense molecules that selectively inhibit cdk4 expression can be produced using techniques known to those of skill in the art. Methods for administering such reagents are the same as for the agents which regulate cdk6 as described above.

According to the present invention, a ribozyme typically contains stretches of complementary RNA bases that can base-pair with a target RNA ligand, including the RNA molecule itself, giving rise to an active site of defined structure that can cleave the bound RNA molecule (See Maulik et al., 1997, supra). Therefore, a ribozyme can serve as a targeting delivery vehicle for the nucleic acid molecule encoding cdk6, or alternatively, the ribozyme can target and bind to RNA encoding cdk4, and thereby effectively inhibit the translation of cdk4.

As used herein, a cdk4 anti-sense nucleic acid molecule is defined as an isolated nucleic acid molecule that reduces expression of cdk4 by hybridizing under high stringency conditions to a gene encoding cdk4. Such a nucleic acid molecule is sufficiently similar to cdk4 that the molecule is capable of hybridizing under high stringency conditions to the coding or complementary strand of the gene or RNA encoding the natural cdk4. A cdk4 gene includes all nucleic acid sequences related to a cdk4 gene such as regulatory regions that control production of the protein encoded by that gene (such as, but not limited to, transcription, translation or post-translation control regions) as well as the coding region itself. The gene encoding cdk4 has been previously cloned and sequenced and are available to those of skill in the art (See GenBank® Accession No. 4502734).

As used herein, stringent hybridization conditions refer to standard hybridization conditions under which nucleic acid molecules are used to identify similar nucleic acid molecules. Such standard conditions are disclosed, for example, in Sambrook et al., *Molecular Cloning: A Laboratory Manual*, Cold Spring Harbor Labs Press, 1989. Sambrook et al., ibid., is incorporated by reference herein in its entirety (see specifically, pages 9.31–9.62,11.7 and 11.45–11.61). In addition, formulae to calculate the appropriate hybridization and wash conditions to achieve hybridization permitting varying degrees of mismatch of nucleotides are disclosed, for example, in Meinkoth et al., 1984, *Anal. Biochem.* 138, 267–284; Meinkoth et al., ibid., is incorporated by reference herein in its entirety.

More particularly, high stringency hybridization conditions, as referred to herein, refer to conditions which permit isolation of nucleic acid molecules having at least about 70% nucleic acid sequence identity with the nucleic acid molecule being used to probe in the hybridization reaction, more particularly at least about 75%, and most particularly at least about 80%. Such conditions will vary, depending on whether DNA:RNA or DNA:DNA hybrids are being formed. Calculated melting temperatures for DNA:DNA hybrids are 10° C. less than for DNA:RNA hybrids. In particular embodiments, stringent hybridization conditions for DNA:DNA hybrids include hybridization at an ionic strength of 0.1×SSC (0.157 M Na$^+$) at a temperature of between about 20° C. and about 35° C., more preferably, between about 28° C. and about 40° C., and even more preferably, between about 35° C. and about 45° C. In particular embodiments, stringent hybridization conditions for DNA:RNA hybrids include hybridization at an ionic strength of 0.1×SSC (0.157 M Na$^+$) at a temperature of between about 30° C. and about 45° C., more preferably, between about 38° C. and about 50° C., and even more preferably, between about 45° C. and about 55° C. These values are based on calculations of a melting temperature for molecules larger than about 100 nucleotides, 0% formamide and a G+C content of about 50%. Alternatively, $T_m$ can be calculated empirically as set forth in Sambrook et al., supra, pages 11.55 to 11.57.

The following examples are provided for the purpose of illustration and are not intended to limit the scope of the present invention.

EXAMPLES

The following Materials and Methods were used in the experiments described in Examples 1–3.

Cell culture. NIH/3T3 cells (ATCC Accession No. CRL-1658) were cultured in D-MEM (Dulbecco-modified Eagle's medium; Gibco-BRL) containing 10% fetal calf serum(FCS) and antibiotics (penicillin/streptomycin). Cells were always sub-cultured before reaching confluence. For the serum-starvation experiments, cells were placed in medium containing 0.1% FCS and incubated for 48 to 72 hours. Cells were then stimulated to re-enter the cell cycle by replacing the medium with complete growth medium with 10% FCS. Cell viability was determined by trypan blue dye-exclusion.

Transfection. All of the plasmids used (pCMVcdk2dn, pCMVcdk4dn, and pCMVcdk6dn (van den Heuvel et al., 1993, Science, 262:2050–2054) were gifts from Drs. E. Harlow, S. van den Heuvel and J. LaBaer (Massachusetts General Hospital, Charlestown, Mass.). Transfection was performed using Lipofectin® according to the protocol recommended by the supplier (Gibco/BRL). Transfected cells were transferred to 24 well culture dishes and then placed in complete medium containing 200 μg/ml neomycin at 48 hours after transfection. Medium was changed every three days and growing colonies were assessed for cdk protein expression and kinase activity using techniques described below.

Metabolic labeling with $^3$H-thymidine. Cells ($10^5$) were seeded in 6-well culture dishes and permitted to attach and grow for one day, after which serum starvation was performed, as described above. After serum re-stimulation, cells were pulse-labeled for one hour periods at designated times with $^3$H-thymidine (10 μCi/well in 1 ml medium) and then cells were collected, washed several times in PBS to remove free $^3$H-thymidine, and incorporated $^3$H-thymidine was determined by liquid scintillation counting.

Immunoblot analysis. For use in immunoblot analysis (Terada et al., 1991, *J. Immunol.* 147:698–704; Szepesi et al., 1994, *Blood* 84:3413–3421), cells were washed with PBS and then lysed at 4° C. in a buffer containing 10 mM Tris-HCl, 50 mM NaCl, 0.5% sodium deoxycholate, 0.2%

SDS, 1% Nonidet P-40, 1 mM PMSF, 50 mg/ml aprotinin, 50 mM leupeptin, and 0.1 mM sodium orthovanadate. After removal of cellular debris by centrifugation, lysates were prepared for electrophoresis and PAGE was performed as described previously (Terada et al., 1991, supra). After electrophoretic transfer of proteins to nitrocellulose membranes, the membranes were incubated overnight at 4° C. in TBST containing 2% BSA. They were then incubated with the appropriate primary antibody for 2 hr at room temperature. For detection of specific proteins, an enhanced chemiluminescence method was used with an appropriate secondary antibody (a 1:5000 dilution of either horseradish peroxidase-linked sheep anti-mouse Ig or donkey anti-rabbit Ig; Amersham Pharmacia Biotech, Piscataway, N.J.). The latter reagents were incubated with the membrane for 45 minutes. Reagents for the chemiluminescence immunoblotting detection method were obtained from Amersham. Anti-cdk4, anti-cdk6, anti-cdk2, anti-cyclin D2 antibodies (all rabbit polyclonal) and anti-cyclin D1 (a mouse monoclonal) were obtained from Santa Cruz Biotechnology (Santa Cruz, Calif.).

Immunoprecipitation. Metabolic labeling of cellular protein was performed (Lucas et al., 1995, Blood 86:2268–2280) by placing cells in methionine-free medium containing dialyzed FCS (10%) and incubating for 2 h with 100 µCi/ml of [$^{35}$S]-methionine (specific activity: 1200 Ci/mmol; Dupont NEN, Wilmington, Del.). Cells were suspended in a solution containing 50 mM HEPES (pH 7.5), 150 mM NaCl, 1 mM EDTA, 2.5 mM EGTA, 1 mM dithiothreitol, 10% glycerol and 0.1% (v/v) Tween® 20. They were disrupted by sonication for 15 seconds at 4° C. After preclearing of lysates with recombinant protein G-coupled Sepharose® beads (Zymed, San Francisco, Calif.), specific immune complexes were precipitated with anti-cdk4 or anti-cdk6 antibody. Immunoprecipitates were washed five times in the Tween® 20-containing solution described above and then resuspended in a sample buffer for electrophoresis. The sample were boiled at 95° C. for 5 min and then either frozen or used immediately for analysis.

Determination of cdk2, cdk4 and cdk6 kinase activities. The procedures used were based on those described for isolation and assay of cdk2, cdk4 and cdk6 (Matsushime et al., 1994, Mol. Cell. Biol. 14:2066–2076; Meyerson et al., 1994, Mol. Cell. Biol. 14:2077–2086; Lucas et al., 1995, J. Immunol. 154:6275–6284; and Lucas et al., 1995, J. Cell. Physiol. 165:406–416). For cdk2 kinase assay, cells were lysed in a solution containing 50 mM Tris-HCl(pH 7.4), 250 mM NaCl, 5 mM EDTA, 0.1% Nonidet NP-40, 1 mM PMSF, 50 mg/ml aprotinin, 50 mg/ml leupeptin, and 100 mM sodium orthovanadate. For cdk4 and cdk6 kinase assays, cells were lysed in a solution containing 50 mM HEPES (pH 7.5), 150 mM NaCl, 1 mM EDTA, 2.5 mM EGTA, 1 mM dithiothreitol, 10% glycerol, 0.1 % (v/v) Tween® 20,0.1 mM PMSF, 10 µg/ml aprotinin, 20 µg/ml leupeptin, 100 mM sodium orthovanadate and 10 mM β-glycerophosphate. They were then disrupted by sonication for 15 sec at 4° C. After preclearing of lysates with recombinant protein G-coupled Sepharose® beads (Zymed, San Francisco, Calif.), specific immune complexes were precipitated with anti-cdk2, anti-cdk4 or anti-cdk6 antibody. Immunoprecipitates were washed several times with the lysis solutions described above and then one time with kinase reaction buffer, which contained 50 mM Tris-HCl (pH 7.4), 10 mM magnesium chloride, 1 mM DTT for the cdk2 kinase assay and 50 mM HEPES (pH 7.2), 10 mM magnesium chloride, 5 mM manganese chloride, and 1 mM dithiothreitol for cdk4 and cdk6 kinase assays. The immunoprecipitates were then suspended in kinase reaction buffer containing 1.0 µg histone H1 (Boehringer Mannheim, Indianapolis, Ind.) or 0.5 µg of recombinant p60Rb protein (QED/Canji, San Diego, Calif.), 100 mM ATP, and 20 µCi of [$\gamma^{32}$]-ATP in a final volume of 25 µl and incubated at 30° C. for 15 min for cdk2 kinase assay and for 30 min for cdk4 and cdk6 kinase assays. Reactions were stopped by addition of the SDS-containing sample buffer. After heating at 95° C. for 5 min and then cooling, the protein G immunobeads were pelleted by centrifugation and proteins in the reaction mixture were resolved by 10% PAGE. The histone H1 or p60Rb bands were visualized by a brief staining of the gels with Coomasie Blue (R-250) in fixative (7% acetic acid/40% methanol/53% water). The gels were then dried and the labeled bands were detected by autoradiography.

Measurement of c-jun kinase(JNK) activity. GST-c-Jun fusion protein was purified from bacterial lysates using GSH-Sepharose® beads at room temperature with gentle rocking. Cells lysates were prepared and assayed for JNK activity as described by Sakata et al. (Sakata et al., 1995, J. Biol. Chem. 270:30823–30828). In brief, following cell stimulation, $2 \times 10^6$ cells we e lysed in lysis buffer (20 mM Tris-HCl, pH 7.6, 250 mM NaCl, 3 mM EDTA, 3 mM EGTA, 0.5% NP-40, 2 mM $Na_3VO_4$, 1 mM DTT, 1 mM PMSF, 20 µg/ml aprotinin, 5 µg/ml leupeptin). The lysates were mixed with 10 µl of GST-c-Jun (1–79) coupled to GSH-Sepharose® beads. The mixture was rotated at 4° C. for 3 hr in a microcentrifuge tube and pelleted by centrifugation at 14,000 rpm for 5 min. The pelleted beads were washed 2 times in lysis buffer and once in kinase buffer (20 mM HEPES, pH 7.5, 20 mM β-glycerophosphate, 10 mM $MgC_2$, 1 mM DTT, 50 mM $Na_3VO_4$, 10 mM p-nitrophenyl phosphate), and then resuspended in 40 µl of kinase buffer containing 10 µCi of [$\gamma^{32}$P]-ATP. After 20 min at 30° C., the reaction was terminated by adding 3×Laemmli sample buffer and boiling for 3 min. Samples were resolved by 12% SDS-PAGE and visualized by autoradiography.

Example 1

This example demonstrates that cell cycle regulatory proteins increase in amount after 3T3 cells are stimulated to leave a quiescent (GO) state.

The 3T3 cell line has been often used as a model for analyzing "normal growth control" in an in vitro system (Todaro et al., 1963, J. Cell Biol. 17:299–313). For the following studies, NIH/3T3 cells (ATCC Accession No. CRL-1658) were cultured in 10% fetal calf serum (FCS). initial analysis of randomly growing 3T3 cells indicated that the cells contained cdk2, cdk4 and cdk6 proteins. However, whereas cdk2 nd cdk4 kinase activities were readily detected, virtually no cdk6 activity above the background levels associated with the assay were detected (data not shown). Therefore, cultures of resting 3T3 cells were examined as they were induced to synchronously enter and proceed through the cell cycle. For growth arrest, cells were incubated for 72 hrs in medium containing 0.1% serum. At this time they were in a pseudo-G0 arrested state, characterized by little or no content of many important cell cycle regulatory molecules (data not shown). The cells had a low amount of cdk4 and cdk2 but little or no detectable cdk6, cyclin D1 or cyclin D2. When the resting cell cultures were replenished with normal growth medium with 10% serum, the amounts of all five molecules rapidly increased in amount. All reached peak levels by about 8 hrs and then declined somewhat by 24 hrs. To place this within the context of the major cell cycle transitions, it was observed that cultures entered S-phase by 8–9 hrs after release (as measured by $^3$H-thymidine incorporation into DNA); mitosis, detected by microscopic observation of the cultures, occurred at about 18–20 hrs after release from G0 (data not shown). The kinase activities of cdk2, cdk4 and cdk6 were also examined over a similar time course (data not shown). Little or no activity was seen in resting cells. Both cdk4 and cdk2 activity increased as early as 3 hrs after cell cycle entry, reaching maximal levels by about 14 hrs. Both activities decreased by 24 hrs. Cdk6 activity was virtually unchanged throughout the time course studied, except for an increase at 24 hrs which may be due to the fact that cell number had also doubled by this time point. These observations suggested that cdk6 and cdk4 might have different functions in cell growth. To further probe possible functions of the enzymes, cell lines were developed following transfection with dominant-negative forms of the kinases.

Example 2

The following example describes the isolation and characterization of stable transfectant cell lines expressing dominant-negative forms of cdk2, cdk4 or cdk6.

Plasmids encoding putative dominant-negative (dn) forms of the cdk2, cdk4 and cdk6 kinases were obtained (van den Heuvel et al., 1993, supra) and used to transfect 3T3 cells. Colonies stably expressing the encoded proteins were isolated and expanded. Although many colonies were isolated, the analyses presented here were limited primarily to two cdk2 dn clones, four cdk4 dn clones and three cdk6 dn clones. No discernible morphological differences among clonal lines were observed. The dn proteins are mutated in their ATP-binding sites and are thus inactive because they do not bind the nucleotide (van den Heuvel et al., 1993, supra). Since they can still bind appropriate cyclins, it is surmised that their dominant-negative effects are achieved through sequestration of the cyclins needed by the wild-type enzymes. In the original description of these proteins (van den Heuvel et al., 1993, supra), evidence that the cdk4 or cdk6 dn forms indeed inhibited endogenous kinase activities was not provided. More recently, Jiang et al. (Jiang et al., 1998, *Mol. Cell. Biol.* 18:5284–5290) have demonstrated that a U2OS cell line expressing the dominant-negative form of cdk4 have a markedly reduced level of cdk4 enzyme activity. A direct demonstration of the efficacy of the dominant-negative forms of the enzymes in abrogating endogenous kinase activity therefore became an important part of characterization of the isolated clonal lines described here.

Rb-kinase activities associated with cdk4 immunoprecipitates in proliferating parental 3T3 cells and in the four cdk4 dn clonal lines (cdk4dn clones 36, 38, 39 and 41) were determined (data not shown). Immunoblot analysis revealed that the four dn lines all had elevated levels of cdk4 protein (combination of endogenous wild-type and dn forms of the protein). Quantitative analysis of the cdk4 kinase levels in these and several other clones (data not shown) indicated that clonal line 36 had the most dramatic reduction in cdk4 kinase activity, with a 96% reduction in activity in proliferating cultures, as compared to the level in parental 3T3 cells. In general, lines with the highest amounts of protein (e.g., cdk4dn lines 36 and 41) exhibited the greatest reductions in kinase activity. Since cdk4 kinase levels vary throughout the cell cycle, cdk4 kinase and protein levels were compared in parental 3T3 cells and in a cdk4dn line as arrested cells were serum-stimulated to re-enter the cell cycle. Immunoblot analysis confirmed that the cdk4dn41 line had a greater amount of cdk4 protein, which appeared to fluctuate little in amount throughout the cycle. In the parental cells, cdk4 kinase activity reached a maximal level at about 4 to 8 hrs after cell cycle entry and then declined slightly in amount. In the cdk4dn41 line, a maximal level was not achieved until at least 18 hrs; furthermore, this level was much less than that seen in the parental cells at a corresponding time. This analysis is shown for the cdk4dn41 line and not cd4dn36 because the level seen in the latter line is so low that any significant changes throughout the cycle could not be adequately detected (data not shown). It was thus clear that the cdk4 dn form indeed inhibited endogenous cdk4 kinase activity and that stable proliferating cell lines with greatly reduced levels of kinase activity but an apparently normal morphological appearance could be isolated.

A similar analysis was performed with the cdk6dn lines 3, 15 and 17 (data not shown). As compared to parental cells, cdk6dn lines had elevated levels of cdk6 protein. cdk4 protein and kinase levels were little changed in the cdk6dn lines. Since cdk4 and cdk6 can both bind to cyclins D1 and D2, it was initially expected that introduction of either dn form(cdk4 or cdk6) would affect the other kinase. Possible reasons why the cdk6dn form had little or no affect on cdk4 kinase levels are discussed below. To demonstrate that the dn form of cdk6 indeed bound to cyclins, parental and cdk6dn3 cells were metabolically labeled with $^{35}$S-methionine and cdk6 was immunoprecipitated. Results demonstrated that the cdk6dn line indeed had a greatly elevated level of cdk6 (data not shown). Proteins with the electrophoretic mobilities of cyclins D1 and D2 (19, 31) were co-immunoprecipitated with the cdk6. Since the parental cells have a much lower level of cdk6, these bands are barely seen in the exposure level used in this assay. Ascertaining that the cdk6dn protein inhibited endogenous cdk6 kinase activity proved more complicated than the analysis performed for cdk4. As noted above, initial analysis of parental 3T3 cells indicated that although the cells had cdk6 protein, virtually no Rb-kinase activity was associated with it. cdk6 protein and kinase levels were measured as resting 3T3 cells entered the cell cycle. Immunoblot analysis showed that cdk6 protein levels increased rapidly in amount by 0.5 hrs and peaked at 1 hr after stimulation. The protein amount then declined to the amount present at 0.5 hr and remained at this basal level. The rapid fluctuation in cdk6 protein amount was reflected in increased Rb-kinase levels. This increased kinase activity was blunted in the cdk6dn3 line. Although some activity w as seen at 1 hr after stimulation, it returned to background levels by 2 hrs, whereas the parental 3T3 cells still exhibited significant activity at this time point. It was also shown by immunoblot analysis that the cdkdn3 line had very high levels of cdk6 protein throughout this time course.

Finally, cdk2 levels were examined in proliferating parental 3T3 cells and in cdk4 and cdk6dn lines (data not shown). Cdk2 is thought to act downstream of cdk4/cdk6 in the cell cycle. Cells growing with reduced levels of cdk4 kinase activity also had reduced levels of cdk2. In contrast, abrogation of cdk6 levels had no effect on cdk2 kinase activity, again suggesting differential functions for the cdk4 and 6 kinases. The results also indicated that cdk4 activation was an upstream requisite for complete cdk2 activation. This was also indicated by an analysis of cell lines which expressed a dominant-negative form of cdk2 and therefore had reduced levels of cdk2 kinase activity. The results demonstrated that D2f2 and D2f5 clonal lines produced by transfection overproduced cdk2 protein and had reduced cdk2 kinase activity. Despite this greatly reduced cdk2 activity, cdk4 activity was only marginally affected in the cell lines. Since cdk2 and cdk4 activities change through the cell cycle, they were examined in the 3T3 parental line and the cdk2dn line D2f2. In the parental line, cdk2 and cdk4 kinase levels increase after serum stimulation of resting cells, as described above. The increase in cdk2 activity is greatly reduced and delayed in the cdk2dn line. However, the kinetics of increase of cdk4 activity were very similar in the two lines. In fact, in this experiment cdk4 activity was somewhat greater in the cdk2dn line than in the parental cells, again indicating that cdk4 accumulation and activity were independent of cdk2.

Example 3

The following example demonstrates the growth properties of cell lines expressing dominant-negative forms of cdk2, cdk4 or cdk6.

From the analyses described in Examples 1 and 2 above, it was clear that cdk2, cdk4 or cdk6 kinase activities were substantially abrogated in the cdk2dn, cdk4dn or cdk6dn lines, respectively. The effects on cellular proliferation were next examined. Growth curves were derived by examination of proliferation over a period of 5 days for parental 3T3 cells, two cdk2 dn lines (clones D2f2 and D2f5), three cdk4dn lines (clones 38, 39 and 41), and three cdk6dn lines (clones 3, 15 and 17) in medium containing 1%, 3% or 10% serum. Optimal growth of 3T3 cells is seen at 10% serum. Results showed that the growth of the cdk2dn and cdk4dn lines was clearly less than the parental cells, at all serum levels examined (data not shown). In contrast, no significant effects of cdk6dn expression on growth were seen. The growth curves for the three cdk6dn lines were virtually identical to those seen for parental 3T3 cells. Even at the lowest serum concentration, the cdk6dn line grew at a rate comparable to the parental 3T3 cells. In FIG. 1, growth curves for seven of the lines in regular growth medium with 10% serum are presented (parental 3T3 cells; cell lines expressing the dn form of cdk2 are lines D2f2 and D2f5; cell line expressing the dn form of cdk6 is line 6d3 and cell lines expressing the dn form of cdk4 are lines 4d38, 4d39 and 4d41). Clearly, presence of the dn form of cdk2 or cdk4 but not of cdk6 markedly affects growth rate. Molecular analysis indicated that cdk4 kinase levels of parental 3T3 cells growing in medium with the low serum content were comparable to cdk4 kinase levels seen in cdk4dn lines growing in the high serum content (data not shown).

In order to determine whether or not cdk4 abrogation resulted in delayed S-phase entry, growth-arrested 3T3, cdk2D2f2, cdk6dn3, and cdk4dn4l cells were released from G0 and then pulse-labeled, at various times after release, with $^3$H-thymidine. DNA synthesis was observed in the 3T3 and cdk6dn3 cells at about 8 to 9 hrs after serum addition. This was delayed to about 11 to 12 hrs for the cdk4dn41. In addition, the magnitude of incorporation for the parental and cdk6dn3 lines was virtually identical, but much decreased in the cdk4dn line. It thus appears that G1 phase was substantially increased in length in cells expressing low levels of cdk4. As expected, abrogation of cdk2 kinase activity also resulted in increased G1-phase length and decreased incorporation of $^3$H-thymidine.

An alternative explanation for delayed S-phase entry is that events involved in the G0 to G1 phase transition itself are compromised by abrogation of cdk4 activity. To address this question, a very early event which occurs after serum or growth factor stimulation of resting cells, activation of c-jun kinase or JNK (Woodgett et al., 1996, *Cancer Surveys* 27:127–138) was examined. The results demonstrated that JNK activity peaks as early as 30 min after serum stimulation of parental 3T3 cells and then declines in amount (data not shown). The kinetics of appearance and decline of JNK appeared virtually identical in the cdk4dn41 and cdk6dn3 lines. Similarly, Erk2 kinase activation appeared to occur with similar kinetics and to a similar extent in the three cell types (data not shown). The data suggest that at least some of the very earliest events that occur after serum-stimulation occurred normally in cells with either decreased cdk6 or cdk4 levels.

Figure 2:
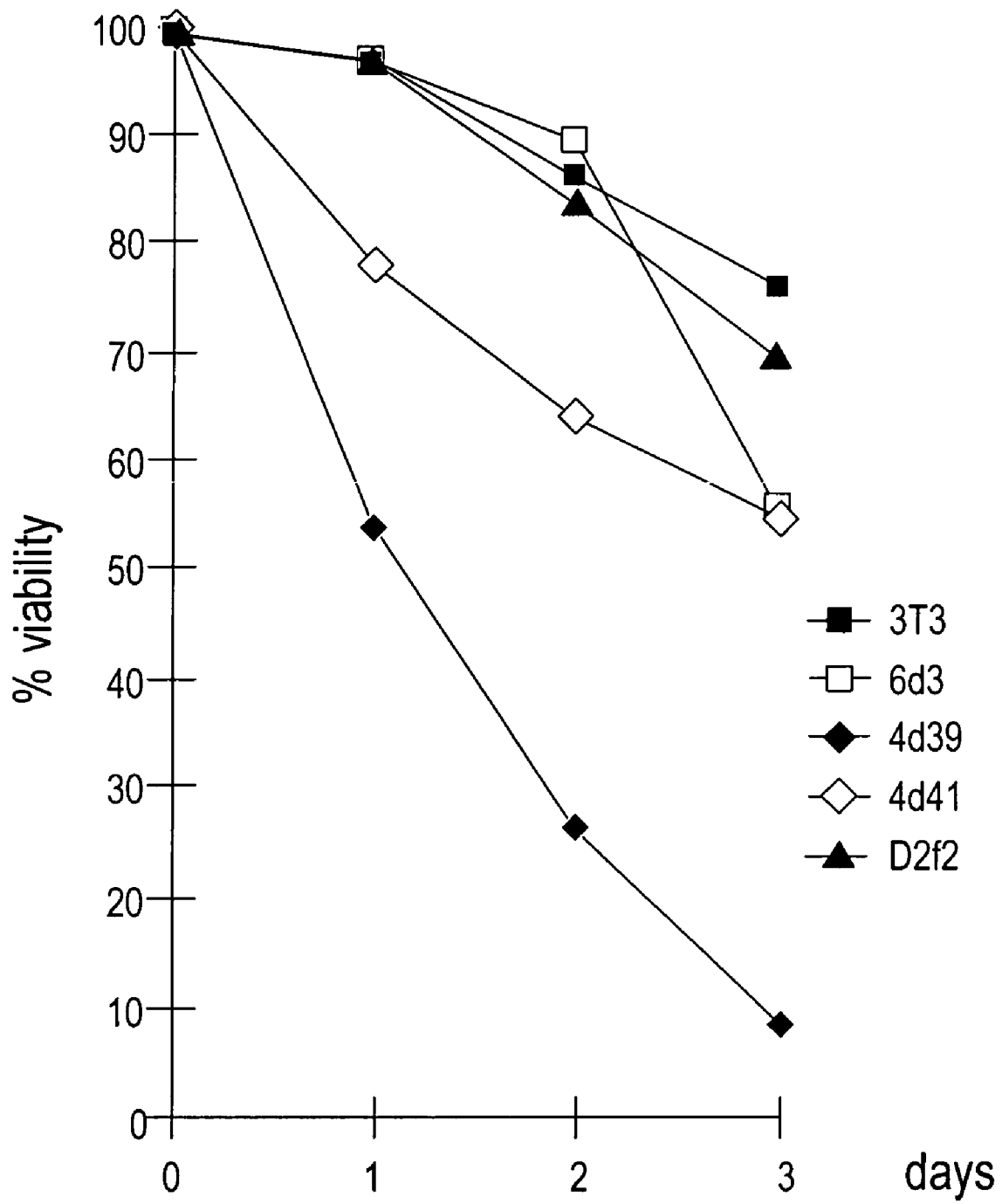
FIG. 2 is a line graph illustrating viability of parental 3T3 cells and of cell lines expressing the dn forms of cdk2 (line D2f2), of cdk6 (line 6d3) or cdk4 (lines 4d39 and 4d41) after transfer of growing cultures to medium containing 0.1% FCS.

A last property related to the normal growth control of 3T3, viability during serum starvation, was also examined, as shown in FIG. 2 (Viability of parental 3T3 cells and of cell lines expressing the dn forms of cdk2 (line D2f2), cdk6 (line 6d3) and cdk4 (lines 4d39 a 4d41) after transfer of growing cultures to medium containing 0.1% FCS). Growing cultures of the five cell lines were transferred from medium containing 10% FCS to medium with 0.1% FCS. The viability of the cells was determined after staining of cells with trypan blue. When parental 3T3 cells were transferred to medium containing 0.1% serum, there was a gradual decrease in viable cell number. By day 2, about 10% of the cells were dead; this increased to about 20% by day 3. Results obtained with a cdk2dn line were similar. A cdk6dn line also showed a similar low level of cell death during the first two days of serum starvation, with significantly more cell death by three days. In contrast, cdk4dn cells showed a much more dramatic and rapid cell death.

Here, the present inventors have shown that cdk4 and cdk6 also have different properties in 3T3 fibroblasts. In proliferating 3T3 cells, cdk4 activity is high whereas cdk6 activity is not detectable. After re-entry of resting cells into the cell cycle, both activities appear relatively rapidly, but cdk6 activity wanes within several hours whereas cdk4 activity is maintained at relatively high levels. In summary, results presented in Examples 1–3 above clearly support important roles for cdk4 and cdk2 in 3T3 cell growth. Little discernible effect of cdk6 abrogation was observed. It is possible that in 3T3 cells, cdk4 may compensate for decreased cdk6 function. However, since cdk6 activity is limited to a short period in the cell cycle and is relatively low compared to cdk4 activity, cdk6 may not be able to compensate for decreased cdk4. Alternatively, these results indicate that cdk4 and cdk6 may each have specific non-overlapping functions in cells.

From these studies, it appears that cdk4 may play a special role in the G0 or very early G1 phase in 3T3 cells. In contrast, abrogation of cdk6 activity exerted none of the dramatic effects of decreased cdk4 activity, suggesting that it is not essential for 3T3 cell growth itself. Since cdk6 is activated soon after stimulation of resting 3T3 cells or T lymphocytes, it was expected that the kinase may play an important role in cell cycle entry or the very early G1 phase of cells entering the cycle. However, abrogation of cdk6 activity in early G1 appeared to have no affect on the kinetics of cell cycle entry, G1 progression, nor on activities, such as JNK or Erk2, which occur very early in G1 phase.

One significant effect of cdk6 abrogation on a cell growth property was shown in that reduced cdk4 activity levels rapidly decreased the viability of cdk4-deficient, serum-starved cells, as compared to parental cells, whereas reduced cdk6 activity levels had little effect on viability, until after 48 hrs, at which time these cells also began to die more quickly than parental cells. Analysis of parental 3T3 cells subjected to serum-starvation showed that by 48 hrs after starvation, cdk6 levels were reduced to almost nothing, whereas cdk4 levels remained high; by 72 hrs, however, cdk4 levels were dramatically lower as well. Without being bound by theory, the present inventors believe that expression of the cdk6 dn form in serum-starved cells is not sufficient to markedly reduce cdk4 activity until 72 hours of starvation, when cdk4 protein levels have dramatically fallen. Thus, the effect of the cdk6 dn form in this case may be due to sequestration of cyclin D and an indirect effect on cdk4 activity, which appears necessary for cells to remain viable under conditions of serum-starvation.

A previous study (Latham et al., 1996, *Mol. Cell. Biol.* 16:4445–4455) which utilized the wild-type and dominant-negative forms of cdk4 and cdk6 suggested that ectopic expression of any of these four proteins could enable cells to overcome p53-mediated growth arrest. In the present inventors' studies, however, it is clear that the dominant-negative form of cdk4 effectively blocks cdk4 activity and exerts a profound inhibitory effect on cell growth. Furthermore, as shown in Examples 4–7, over-expression of the wild-type form of cdk6 is also growth-suppressing. The present inventors' detailed analysis of the growth properties of transfected 3T3 cells has demonstrated dramatic effects of decreased cdk2 or cdk4 activities on cell growth and little discernible effect of cdk6 abrogation. Such differences may be due to the use of different cell types having varying complements of cyclins, cdks and CDKIs, and to different experimental protocols used. However, the data provided in Examples 4–13 below demonstrate that cdk6 plays a different role than cdk4 which heretofore was not known.

The following Materials and Methods were used in the experiments described in Examples 4–7.

Cell culture. NIH3T3 cells were cultured as described in Examples 1–3. For irradiation of cells with ultraviolet light (UV-C), growth medium was removed from the cells and they were washed once with phosphate-buffered saline (PBS). The cells were then covered with PBS (5 ml for a 100 mm tissue culture dish; 3 ml for a 60 mm dish). The cells were irradiated with a UV lamp (Model UVM-57; UVP Inc., San Gabriel, Calif.) to provide a dose of 20 J/m$^2$. PBS was removed and the cells were incubated in complete growth medium.

Transfection. The plasmids used (pCMVcdk6wt and pCMVcdk6dn) and the methods of transfection were as described in Examples 1–3.

Immunoblot analysis. Immunoblot analysis was performed as described in Examples 1–3. Rabbit polyclonal anti-cdk4, cdk6, p130, p107, p53 (pan-specific) and Bax antibodies were obtained from Santa Cruz Biotechnology (Santa Cruz, Calif.).

Immunoprecipitation of p53 protein. Metabolic labeling of cellular protein was performed as described in Examples 1–3. After preclearing of lysates with recombinant protein G-coupled Sepharose® beads (Zymed, San Francisco, Calif.), specific immune complexes were precipitated with an anti-p53 antibody (Ab-1 from Oncogene Research Products, Cambridge, Mass.). Immunoprecipitates were washed five times in NT-40 containing solution described above and then resuspended in a sample buffer for electrophoresis. The sample were boiled at 95° C. for 5 min and then either frozen or used immediately for analysis.

Determination of cdk6 kinase activity. cdk6 kinase activity was determined as described in Examples 1–3.

Northern Blot Analysis. Methods for the extraction of total cellular RNA and for Northern blot analysis were as described previously (Lucas et al., 1995, *J. Cell. Physiol.,* 165, 406–416 and Lucas et al., 1995, *Blood,* 86, 2268–2280). The probe used for detection of p53-specific mRNA was the excised insert from a plasmid containing a full-length human p53 cDNA, which was kindly provided by Dr. B. Vogelstein (Johns Hopkins, Baltimore, Md.).

Example 4

The following example demonstrates the isolation and characterization of stable transfectant cell lines over-expressing cdk6.

As described in Examples 1–3 above, abrogation of cdk6 kinase activity appeared to have little affect on the growth, arrest or cell-cycle re-entry of 3T3 cells. In order to further explore the possible functions of cdk6, stable cell lines with elevated cdk6 levels of the wild-type(wt) form of cdk6 were isolated. Levels of cdk6 protein in proliferating 3T3 cells and five clonally-derived lines over-expressing cdk6 were determined (data not shown). The results demonstrated that levels of cdk4 protein remained essentially unchanged in all of the lo lines. The Rb-kinase activity associated with cdk6 immnunoprecipitates isolated from growing 3T3 cells, the cdk6dn3 line and the cdk6wt1 line were compared. The kinase activity from the first two cell types is little different from background levels observed in the control, that associated with a mock-immunoprecipitate prepared without cell lysate. As noted in Examples 1–3, proliferating 3T3 cells have almost no endogenous cdk6 kinase activity. In contrast, the kinase activity associated with the cdk6 immunoprecipitate from the cdk6wt1 line was very high. It appeared that ectopic expression of cdk6 resulted in high levels of activity, even in proliferating cells.

Figure 3:
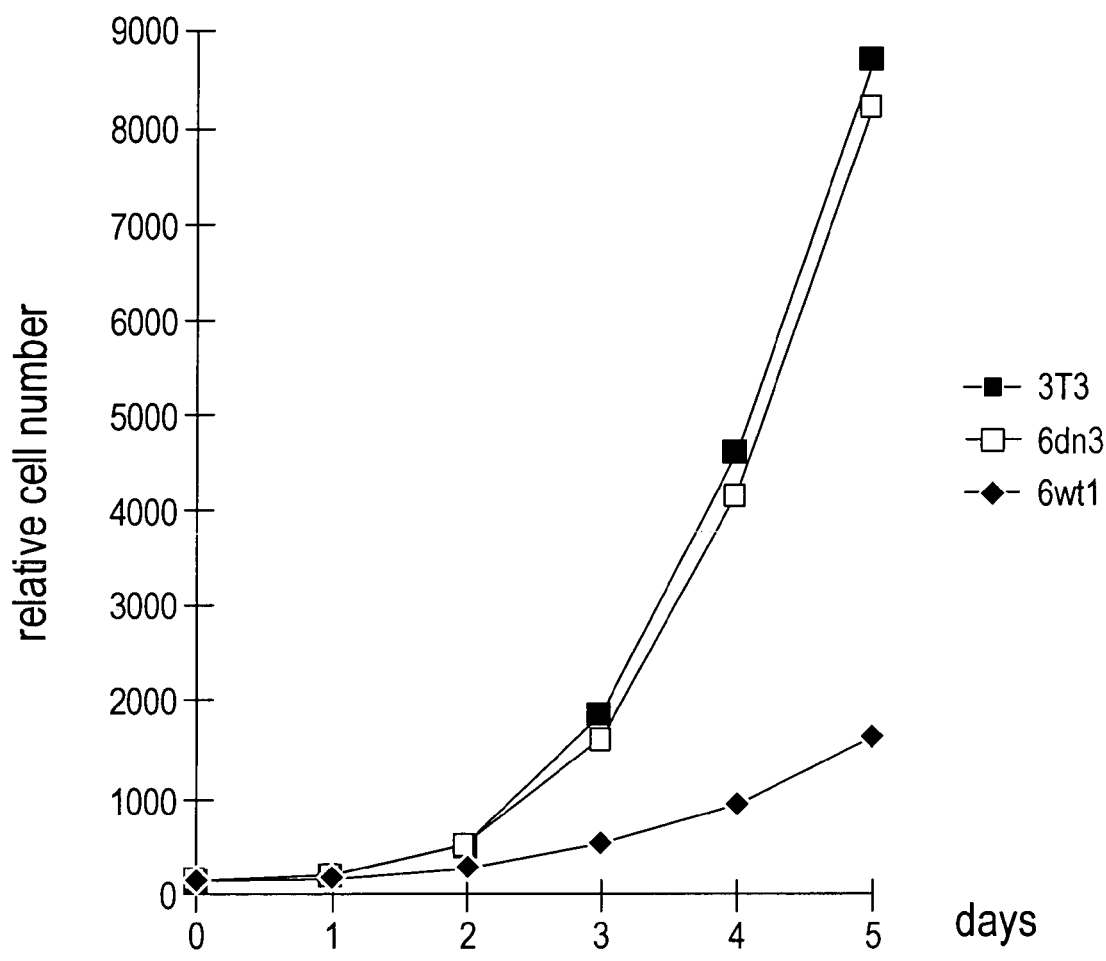
FIG. 3 is line graph showing the growth of parental 3T3 cells and of cells over-expressing the wild-type (line3T3-cdk6wt1) or dominant-negative (line 3T3-cdk6dn3) form of cdk6.

The levels of cdk6 protein in the three immunoprecipitates were further assessed by immunoblotting. At the exposure level used, the endogenous protein levels present in parental cells was undetectable, whereas protein levels seen in the cdk6dn and cdk6wt lines were elevated. In all lines analyzed so far, it appeared that levels of protein expression of the dn form achieved were much higher than cdk6 wt levels. This suggested that whereas inhibition of cdk6 activity has little effect on the growth and health of 3T3 cells in culture, over-expression of the wild-type form might be potentially detrimental. Analysis of the growth properties of cdk6wt lines as performed in Examples 1–3 suggested some differences in growth parameters, as compared to parental cells. Similar to parental 3T3 cells, the cdk6wt lines remain healthy in serum-depleted medium for several days and re-enter the cell cycle after serum addition. However, after sub-culturing of growing cells, the growth rate of cells over-expressing cdk6 was significantly decreased, as shown in FIG. 3 (growing cultures of cells were sub-cultured into fresh medium and cell numbers were determined at 0, 1, 2, 3, 4 and 5 days after sub-culturing. Cell numbers were determined after removal of the cells from growth vessels by trypsinization). As described in Examples 1–3, expression of a dominant-negative form of cdk6 had no effect on growth rate.

Example 5

The following example shows that cell lines stably over-producing cdk6 also overproduce p53 and p130.

Because it appeared that cdk6 kinase activity was expressed at high levels and also at inappropriate times in the cell cycle of cdk6wt lines, it was expected that some effects on cell growth or function would be observed in these lines. A molecular analysis of several molecules known to be important in cellular growth control, such as p53 and Rb-family members, was begun. Results showed that two molecules, the p53 protein and the p130 member of the Rb family, were grossly over-produced in every cdk6wt line examined (data not shown). Molecules examined which showed no difference from normal levels included cdk4, the Rb protein itself, and the p107 member of the Rb-family. At the exposure level used in this experiment, the parental 3T3 line and three cdk6dn lines had no detectable p53 protein. In contrast, all five cdk6wt lines contained very high levels. In normal cells, p53 protein is usually present in low amounts in the resting state, peaks in amount as cells approach S-phase (i.e., 8–9 hrs after serum-stimulation of 3T3 cells) and then declines in amount (Mercer and Baserga, 1985, *Exp. Cell Res.* 160, 31–46; Terada et al., 1991, supra). Despite enormous levels of p53 in the cdk6wt1 cell line, a relatively normal pattern of accumulation and decay was observed (data not shown). Moreover, it was shown that growing 3T3 cells contain some p130 protein (data not shown). Levels are dramatically increased in all of the cdk6wt clonal lines. In contrast, p130 was undetectable in the cdk6dn lines. The involvement of cdk6 in production of p130 is also suggested by the results shown in the next experiment. Specifically, when resting 3T3 cells were stimulated to enter the cell cycle, there was a rapid increase in the amount of p130. In the cdk6dn3 line (described in Examples 1–3), which contains less p130 in the resting state, this increase in amount was both delayed and greatly decreased in amount. In the cdk6dn3 line, the burst of cdk6 activity associated with cell cycle re-entry was greatly abrogated (Examples 1–3).

The cellular content of p53, which has been called the "cellular gatekeeper for growth and division" (Levine, 1997, *Cell*, 88, 323–331) is highly regulated in normal cells, usually at the level of protein stability (Levine, 1997, supra; Ko and Prives, 1996, *Genes & Develop.*, 10, 1054–1072). In the next set of experiments, the basis for the highly elevated amounts of p53 in the cdk6wt lines was examined. First, the half-life of p53 in the cdk6wt3 line was estimated by pulse-chase analysis. Cells were labeled for a brief period with $^{35}$S-methionine and then, at various times thereafter, cells were harvested and p53 was prepared by immunoprecipitation. Results showed that a substantial incorporation into p53 was observed during the labeling period (data not shown). As soon as 30 min after the labeling it period, a dramatic decrease in incorporated isotope was detected. After this time, virtually no labeled p53 was detected, although substantial p53 protein levels were present throughout the experiment (data not shown). The results indicate a turn-overtime (half-life) of less than 15 minutes, a result consistent with the normal turn-over of wild-type p53 (Reich et al., 1983, *Mol. Cell. Biol.* 3, 2143–2150.). A comparable analysis in the parental 3T3 cells used by the present inventors was not possible because of the very low levels of endogenous p53 present.

Since the half-life of p53 in the cdk6wt cells appeared to be very short, other parameters which could account for the high levels of p53 observed were investigated. Northern-blot analysis demonstrated that whereas parental 3T3 cells and cdk6dn3 cells had undetectable levels of p53 mRNA, the cdk6wt1 line had substantial amounts (data not shown). It appears then that either the rate of transcription of the p53 gene, or the stability of its mRNA, was greatly enhanced in the cdk6wt line.

Example 6

The following example demonstrates the functionality of the p53 protein over-expressed in cdk6 wt cells.

Gross over-production of wild-type p53 is rarely seen in normal cells because of the powerful growth-suppressing capabilities of the protein. It was remarkable therefore that growing cell lines containing such grossly aberrant levels of p53 could be obtained. However, p53 function is not only regulated by protein amount. To be functional, p53 must also be phosphorylated and transported to the nucleus (see, for example, Martinez et al., 1997, *Oncogene* 14:2511–2520; Kapoor and Lozano, 1998, *Proc. Natl. Acad. Sci. USA*, 95, 2834–2837. It was therefore possible that the high level of p53 seen in the cdk6wt lines was in an inactive, non-growth suppressing form.

Figure 4:
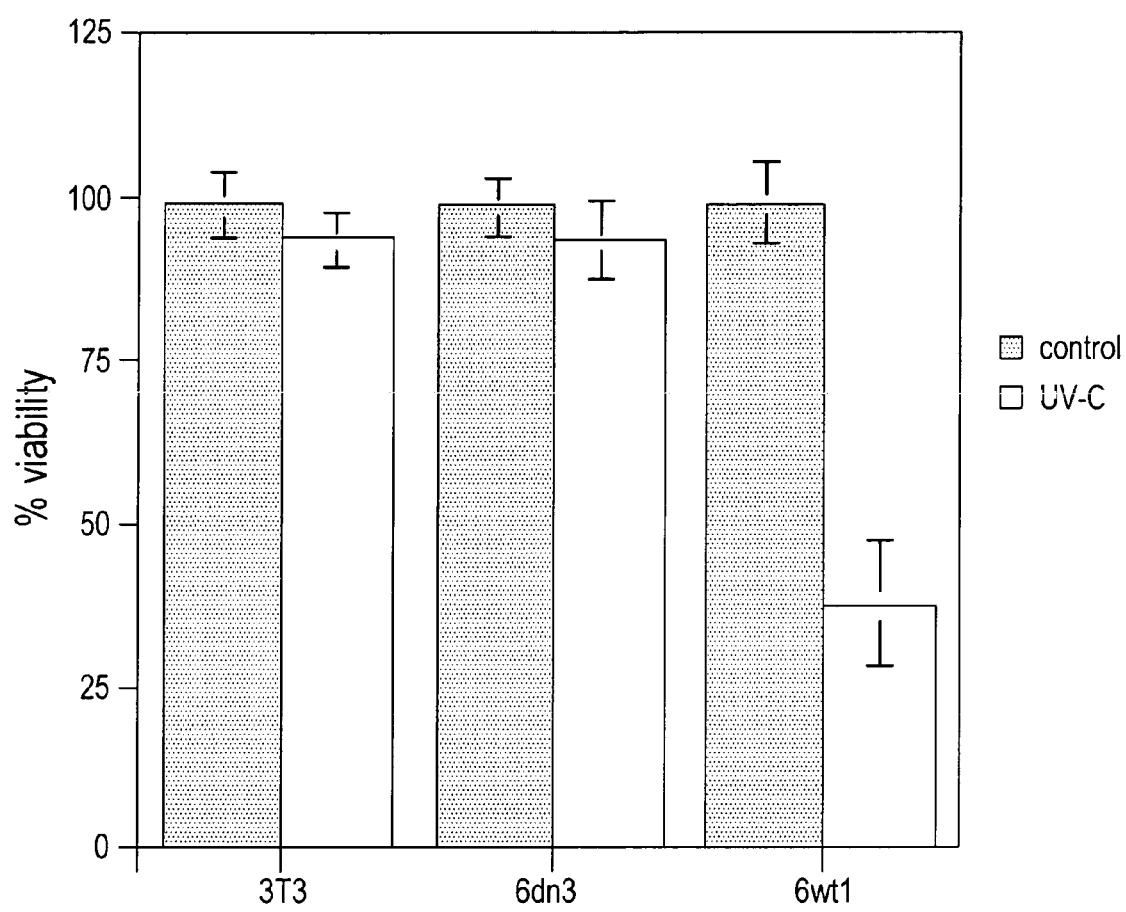
FIG. 4 is a bar graph illustrating the susceptibility of parental 3T3 and transfectant cell lines to irradiation by ultraviolet light.

Increased p53 function can often be seen after UV-irradiation of cells (Lu and Lane, 1993, *Cell*, 75, 765–778 Haapajarvi et al., 1997, *Mol. Cell. Biol.*, 17:3074–3080. Induction of p53 function can be assessed by examining the expression of various p53-regulated genes, which include the cyclin-dependent kinase inhibitor, p21, and the apoptosis-inducing member of the Bcl-2 family, Bax (El-Diery et al., 1993, *Cell*, 75, 817–825 Miyashita and Reed, 1995, *Cell*, 80, 293–299. Therefore, duplicate proliferating cultures of parental 3T3, cdk6dn3 and cdk6wt1 cells were exposed to UV-irradiation (UV-C cultures)and examined for expression of several gene products. In addition, at 24 hrs after irradiation, the viability of the cells was examined by trypan blue dye-exclusion as described in Materials and Methods. As shown in FIG. 4, the viability of the 3T3 or cdk6dn3 cells was little changed by the UV-irradiation protocol used. In contrast, many cells (about 65%) in the cdk6wt1 cell culture were dead by 24 hrs after irradiation. At the time of treatment (0 time), only the cdk6wt3 cells had high levels of p53 and p130, as described above (data not shown). All three lines had high levels of the p107 protein and little or no Bax gene product. Upon UV-irradiation, the Bax-gene protein increased greatly only in the cdk6wt3 cell line. The p53-regulated gene product p21 was also induced in these cells (data not shown). Little or no change occurred in the cellular contents of any of the molecules in the 3T3 or cdk6dn3 cells. By 24 hrs after irradiation, the cellular content of all four molecules in cdk6wt1 cells decreased in amount. As noted above, these cell cultures contained many dead cells by 24 hrs after irradiation. That the cells were dying by a process of apoptosis was suggested by the fact that there was also an increase in amount and cleavage of the enzyme poly(ADP-ribosyl) transferase (data not shown), events often observed during cell death (Lazebnik et al., 1994, *Nature* 371:346–357 Tewari et al., 1995, *Cell*, 81, 801–809. It appears then that overproduction of cdk6 in 3T3 cells resulted in a markedly enhanced sensitivity to UV-induced apoptosis, likely by a p53-dependent process.

Example 7

The following examples demonstrates the reversibility of the cdk6wt phenotype by inhibition of cdk6 activity.

In the experiments described above (Examples 4–6), stable transfectants maintained in culture were used. Attempts to over-express wt and dn cdk6 in transient transfections E s were also attempted. However, although it was possible to prepare cultures which expressed the dn form of cdk6, little over-expression of the wt form could be achieved. In the stably transfected lines, over-expression of the dn form was always higher than the wt form, perhaps suggesting that the latter is far more detrimental to cell viability. As a result, it was not possible to directly determine if transient over-expression of cdk6 resulted in over-expression of p53 and p130. However, since very high levels of the dn form could be expressed in transient transfections, the affect of cdk6dn expression on a cell line already over-expressing cdk6wt was examined. The present results showed that ransfection of the cdk6dn form into cdk6wt1 cells led to a great increase in overall cdk6 protein production, with little affect on cdk4 production. However, by 24 hrs after transfection, abrogation of cdk6 activity by expression of the dn form led to a decrease in cellular content of p53 and p130. Although indirect, these data indicate that maintenance of high levels of p53 and p130 are the result of over-expression of cdk6.

In summary, stable cell lines over-expressing cdk6 throughout the cell cycle were obtained and showed a markedly decreased growth rate. However, molecular analysis revealed that all cell lines over-expressing cdk6 also exhibited marked increases in their levels of the p53 and p 130 proteins. It is of interest that over-expression of cyclin D1 in 3T3 cells also resulted in increased levels of p53 and also of the cyclin-dependent kinase inhibitory protein, p21 (Hiyami et al., 1997, Oncogene, 14, 2533–2542). Although growth rate appeared unaffected in the latter study, the 3T3 cells over-expressing cyclin D1 also acquired the property of anchorage-independent growth.

Both the p53 and p130 proteins play important roles in the negative regulation of growth. For example, the p53 transcription factor, when activated, regulates production of the p21 CDKI (cyclin-dependent kinase inhibitor) and the pro-apoptotic member of the Bcl-2 family, Bax, proteins which can induce GI-phase arrest and cell death, respectively (El-Diery et al., 1993, supra; Miyashita and Reed, 1995, supra; Sherr and Roberts, 1995, Genes & Develop., 9, 1149–1163; Levine, 1997, supra). The p130 protein is a member of the Rb pocket protein-family and appears to play a role in G0 and early G1-phases of the cell cycle (Moberg et al., 1996, Mol. Cell. Biol., 16,1436–1449; Smith et al., 1996, EMBO J. 12, 3133–3142).

Over-production of p53 and p130 were observed in all lines over-expressing wild-type cdk6 but in none expressing the dominant-negative form of the kinase, indicating that the generation of the phenotype was not simply a result of the transfection or cell cloning procedures. Both wt and dn cdk6 constructs were cloned in the same vector and identical selection procedures were used. Furthermore, enhanced production of p53 and/or p130 was not observed in lines producing the dominant-negative form of cdk4, a condition which is also growth-suppressing (Examples 1–3).

Although over-expression of p53 generally signals growth arrest, the cdk6/p53/p130 over-expressing lines described here were all viable but grew at a reduced rate. It was surmised, therefore, that the p53 protein was in at least a partially active form in the cell lines. This notion was supported by the fact that UV-irradiation of the cells led to p21 and Bax protein over-production and rapid cell death, presumably through a p53-mediated mechanism.

All cell lines over-expressing cdk6 activity throughout the cell cycle also overproduced the p53 and p130 proteins. In addition, evidence for a direct link between the two phenomenon is provided by the experiments that showed that, in transient transfections, expression of a dominant-negative form of cdk6 in cells already over-expressing cdk6, p53 and p130 led to a dramatic decrease in abundance of the latter two proteins, implying cause and effect for the role of cdk6 in their accumulation.

A major form of regulation of p53 cellular content is at the level of protein stability. However, over-production of p53 in the cell lines described here appeared to be at the level of mRNA expression and/or stability. Cell lines over-expressing cdk6 may therefore prove useful in probing further the mechanisms regulating p53 mRNA production and accumulation. Although much is known about the means by which p53 controls the expression of genes, such as p21 or Bax, little is yet known about how expression of the p53 gene itself is regulated.

The following Materials and Methods were used in the experiments described in Examples 8–10.

Cell culture. Normal human mammary epithelial cells (HMECs) were obtained from Clonetics (Walkersville, Md.). Most of the experiments described in Examples 8–10 were performed with cells established from two different donors, a 41 yr old Black female and a 22 yr old Caucasian. The cells obtained from the two donors appeared morphologically identical, were positive for cytokeratins 14 and 18, and negative for cytokeratin 19. They were demonstrated to be free of mycoplasma and of HIV, HBV and HCV DNA. They were maintained in Clonetics MEGM® medium supplemented with bovine pituitary extract (52 µg/ml), human recombinant EGF (0.01 µg/ml), insulin (5 µg/ml), hydrocortisone (0.5 µg/ml), Gentamycin (50 µg/ml) and Amphotericin-B (50 µg/ml). Cells were passaged and used for experiments until there was a noticeable change in growth rate and/or a change in morphology. For growth-arrest of normal HMECs, cells were incubated for 7 days in the complete medium except that the pituitary extract content was reduced to 0.052 µg/ml. Growth was reinitiated by adding complete medium with 52 µg/ml pituitary extract. The ten cell lines used were all obtained from the American Type Culture Collection® (Rockville, Md.). The lines used and their culture medium were as follows. The BT-20 and MCF-7 lines were maintained in Eagle's MEM supplemented with 10% fetal calf serum (FCS). MCF-7 medium also contained 10 µg/ml insulin. The BT-474, BT-549, T-47D, ZR-75-1, MDA-MB-157, MDA-MB-453, and MDA-MB-468 lines were grown in RPMI 1640 medium supplemented with 10% FCS. The BT-47 and T-47D medium also contained 10 µg/ml insulin and the BT-549 medium contained 1 µg/ml insulin. The MDA-MB-134-VI* cell line was maintained in RPMI 1640 supplemented with 20% FCS.

Immunoblot analysis. Immunoblot analysis was performed as described in Examples 1–3. Anti-cdk4, anti-cdk6, anti-cdk2, anti-cyclin D2, anti-cyclin D3, anti-p21, anti-p27, anti-p57 antibodies(all rabbit polyclonal) and anti-cyclin D1 antibodies(a mouse monoclonal) were obtained from Santa Cruz Biotechnology (Santa Cruz, Calif.).

Determination of cdk6 kintase activity. cdk6 kinase activity was determined as described in Examples 1–3 (immunoprecipitates were suspended in kinase reaction buffer containing 0.5 µg of recombinant p60Rb protein (QED/Canji, San Diego, Calif.), 100 mM ATP, and 20 µCi of[$\gamma$-$^{32}$]ATP in a final volume of 25 µl and incubated at 30° C. for 30 min).

Example 8

The following example describes a comparison of cell-cycle regulatory molecules in normal HMECs and MCF-7 tumor cells.

Overproduction of many growth-promoting molecules, such as cyclin D1, has been observed in breast tumor cells. Often, previous studies have focused on a single molecule of interest, and do not investigate whether or not the observed difference is due solely to overall growth status, in which case it might be expected that many molecules associated with normal growth might also be overproduced in the cells.

Like many tumors, growing cultures of the MCF-7 tumor-derived cell line has a higher cellular content of cyclin D1 than proliferating normal human mammary epithelial cells (data not shown). Furthermore, the species recognized by the cyclin D1-specific antibody appear to be different. A major band of immunoreactivity is seen in both cell types. However, in the normal cells, an additional band of higher mobility is also seen; two bands of lower mobility are seen in the tumor cell line. When a variety of cell cycle-regulatory molecules were compared in the normal and tumor cell types, it was found that the MCF-7 line also had relatively more of cyclin D3, cdk2, cdk4, and of the CDKIs p21(cip1), p27(kip1) and p57(kip2). Quantitative and qualitative differences in the patterns of immunoreactive molecules were observed for the cyclin D2 molecule. Although the normal and transformed cell extracts appeared to share two species of immunoreactive proteins, other bands were also detected in the immunoblots. Since others have reported that cyclin D2, found predominantly in normal lymphoid cells (Meyerson et al., 1992, *EMBO J.* 11:2909–2917; Meyerson et al., 1994, *Mol. Cell. Biol.* 14:2077–2086; and Lucas et al., 1995, *J. Immunol.* 154:6275–6284)is virtually undetectable in many breast-derived cells (Bartkova et al., 1998, *Oncogene* 17:1027–1037), further analysis of cyclin D2 was not performed in these experiments. Of all of the molecules analyzed, only cdk6 appeared to be in higher amount in the proliferating normal cells, as compared to in growing tumor cells (data not shown).

Like many growth-controlled cell types, HMECs can be induced to enter a resting state by depletion of growth medium. An effective way to induce growth-arrest in the cells is to transfer them into medium containing a greatly reduced content of growth factors. In the HMEC cell culture system utilized here, cells were maintained in a defined medium with added bovine pituitary cell extract (PCE). Reduction of the content of PCE to 0.1% of that added to normal growth medium caused a complete growth arrest by 7 days of culture (data not shown). Since cdk6 levels have been shown to vary early in the cell cycle of other cell types, such as normal T lymphocytes (Meyerson et al., 1994, supra; Lucas et al., 1995, *J. Immunol.*, 154:6275–6284; and Nagasawa et al., 1997, *J. Immunol.* 158:5146–5154) and growth-controlled 3T3 fibroblasts (Examples 1–3), the protein was compared in resting HMECs and cells induced to re-enter the cell cycle.

As in other normal cell types studied, many cell cycle regulatory molecules in HMECs decreased in amount in the resting as compared to the growing state. As demonstrated by immunoblots (data not shown), comparing growth-arrested HMECs with proliferating HMECs, the cellular contents of cyclins D1 and D3, of cdks 2, 4 and 6, and of p27 decreased in amount. The content of p57 was little changed in the resting as compared to the growing state. All of the proteins were examined in HMECs after one and two hours after release from the resting state by reconstitution of medium to the normal content of PCE. The most dramatic changes were seen for the cdk6 and p21 proteins, with both increasing to levels greater than that seen in the proliferative phase. The level of p21 protein at 2 hrs after release was now similar to that seen in growing MCF-7 cells. The level of cdk6 present at 2hrs was even greater than that seen when proliferating MCF-7 cells and HMECs were compared.

Example 9

The following example shows a comparative analysis of HMECs and ten tumor-derived cell lines for cellular content of cyclin D1, cyclin D3, cdk2 and cdk6 protein.

As noted in Example 8, proliferating MCF-7 cells appeared to contain relatively more of the cyclin D1, cyclin D3 and cdk2 proteins and less cdk6 than normal HMECs. To determine the generality of this pattern of protein content, HMECs were compared to ten different tumor-derived cell lines.

Immunoblot analysis of the eleven cell types for cyclin D1 and cyclin D3 was performed and the data are summarized in Table 1. Five of the ten cell lines appeared to have a cellular content of cyclin D1 greater than HMECs, a figure similar to that derived from previous analyses of both primary tumors and tumor-derived lines (Buckley et al., 1993, *Oncogene* 8:2127–2133; Gillett et al., 1994, *Cancer Res.* 54:1812–1817; Sutherland et al., 1995, *Acta Oncologica* 34:651–656; Weinstat-Saslow et al., 1995, *Nature Medicine* 1:1257–1260). Surprisingly, an even higher number, seven of ten lines, appeared to over-produce cyclin D3, as compared to normal cells. Next, cdk2 and cdk6 levels were assessed by immunoblot analysis as shown in Table 2. The results in Table 2 show that nine of 10 lines had more cdk2 than normal cells, whereas all ten lines possessed less cdk6. In all of the analyses reported here, samples were adjusted to be derived from equal cell numbers, and are thus reflective of the cellular contents of the proteins. However, when samples were adjusted to be of equal protein content, the same trends and differences were observed (data not shown). In particular, cdk6 was always lower in amount in the tumor-derived lines than in normal cells.

TABLE 1

The relative contents of cyclin D1 and cyclin D3 proteins in HMECs and ten breast tumor-derived cell lines

| Cell Line | Cyclin D1 content[a] | Cyclin D3 content[a] |
|---|---|---|
| HMEC | ++ | ++ |
| MCF-7 | ++++ | ++++ |
| BT-20 | + | ++ |
| BT-474 | +++ | +++ |
| BT-549 | + | +++ |
| MDA-MB-453 | +++ | +++ |
| MDA-MB-468 | + | +++ |
| T-47D | ++ | +++ |
| ZR-75-1 | ++++ | +++ |
| MDA-MB-157 | ++++ | ++ |
| MDA-MB-134-VI* | − | + |

[a]The relative intensity of each band in the immunoblot was estimated on a scale of "−" (indicating little or no signal) to "++++" (indicating the maximum intensity seen for the eleven samples).

TABLE 2

The relative contents of cdk2 and cdk6 proteins and cdk6 enzyme activity in HMECs and ten breast tumor-derived cell lines

| Cell line | cdk2 content[a] | cdk6 content[a] | cdk6 activity[a] |
|---|---|---|---|
| HMEC | ++ | ++++ | ++++ |
| MCF-7 | +++ | + | +++ |
| BT-20 | +++ | + | +++ |
| BT-474 | ++++ | + | ++++ |
| BT-549 | +++ | +++ | ++ |
| MDA-MB-453 | +++ | − | +/− |
| MDA-MB-468 | +++ | ++ | +++ |

TABLE 2-continued

The relative contents of cdk2 and cdk6 proteins and cdk6 enzyme activity in HMECs and ten breast tumor-derived cell lines

| Cell line | cdk2 content[a] | cdk6 content[a] | cdk6 activity[a] |
|---|---|---|---|
| T-47D | +++ | – | – |
| ZR-75-1 | +++ | – | – |
| MDA-MB-157 | +++ | +++ | ++++ |
| MDA-MB-134-VI* | + | – | – |

[a]The relative intensity of each band in the immunoblot or autoradiogram was estimated on a scale of "–" (indicating little or no signal) to "++++" (indicating the maximum intensity seen for the eleven samples). The "+/–" symbol indicates that a trace of a signal was detected.

Example 10

The following example shows a comparative analysis of HMECs and ten tumor-derived cell lines for cdk6 kinase activity.

The enzyme activity of cdk6 in cells is regulated not only by amount of cdk6 protein, but also the presence of the D-type cyclins. In addition, activity can also be modulated by the presence of the cyclin-dependent kinase inhibitors (CDKIs), cyclin-dependent kinase activating kinases (CAKs) and cdc25 activating phosphatases. Thus, cdk6 protein content may not always correlate directly with enzyme activity. Therefore, cell extracts were prepared from normal HMECs and the ten tumor cell lines and cdk6 activity was measured using an in vitro kinase assay with truncated recombinant Rb protein as a substrate. The activity of the samples is shown in Table 2. For HMECs and for seven of the cell lines (MDA-MB-468, 157, 453, and 134-VI*, BT-549, T-47D and ZR-75-1) there was a fairly good correlation between cdk6 protein and enzyme activity levels. Three of the lines (MCF-7, BT-20 and BT-474) had higher levels of enzyme activity than might be expected from cdk6 protein levels.

Kinase activity for an extract prepared from the T-cell derived Jurkat cell line was included as a positive control. T cells are reported to have a higher level of cdk6 activity than most other cell types examined so far (Meyerson et al., 1994, supra; Lucas, 1995, supra; Nagasawa et al., 1997, supra). Results showed that the normal HMECs and some of the breast tumor-derived cell lines have levels of cdk6 activity comparable to that of T cells. Also of interest, two labeled proteins are observed in the kinase reactions for some cell lines. Such a doublet has also been seen when extracts prepared from normal human T cells treated under certain conditions were analyzed (Lucas, 1995, supra; Nagasawa et al., 1997, supra). One of the proteins represents phosphorylated recombinant pRb protein. Comparison of MDA-MB-157 without pRb protein added to kinase reaction to MDA-MB-157 with added Rb showed that the second protein (referenced as protein "X") is not a form of Rb (data not shown). It is present even when the reaction is performed with an extract from MDA-MB-157 cells, without added pRb substrate. When pRb is included in the reaction with this cell line, two bands are seen. It is surmised that X is an endogenous substrate of cdk6, co-immunoprecipitated with the cdk6/cyclin D complexes. It is also of interest that phosphorylation of X is increased when the exogenous pRb substrate is added, an observation also seen with the T cell system (data not shown).

Figure 5A:
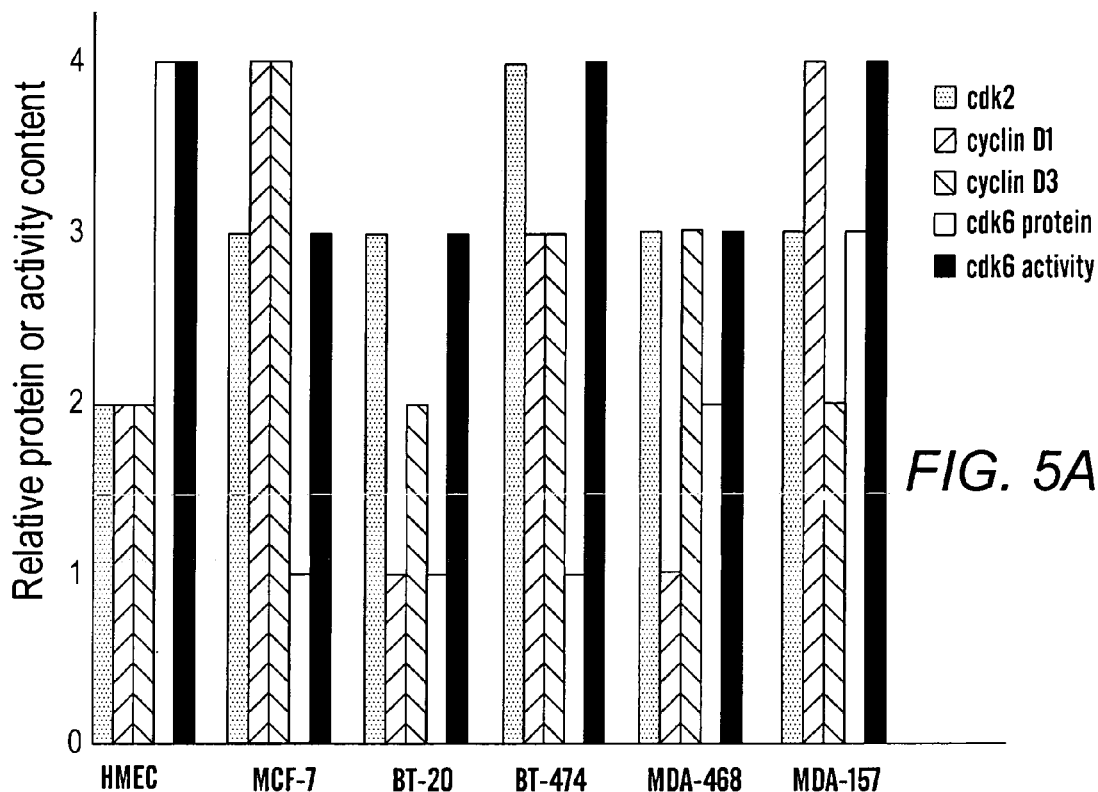
FIG. 5A is a bar graph showing the relative amounts of cdk2, cyclin D1, cyclin D3 and cdk6 proteins and of cdk6 kinase activity in HMECs compared to the amounts in the MCF-7, BT-20, BT-474, MDA-MB-468 and MDA-MB-157 cell lines.
Figure 5B:
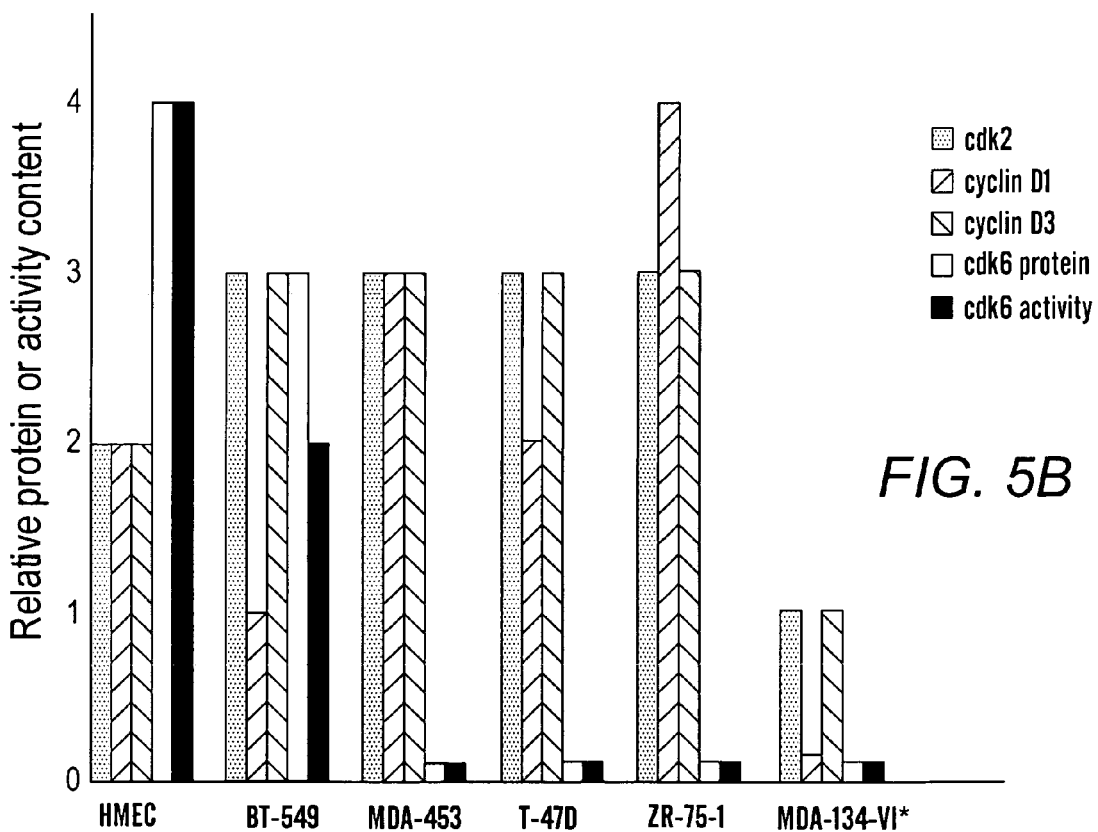
FIG. 5B is a bar graph showing the relative amounts of cdk2, cyclin D1, cyclin D3 and cdk6 proteins and of cdk6 kinase activity in HMECs compared to the amounts in the BT-549, MDA-MB-453, T-47D, ZR-75–1 and MDA-MB-134-VI* cell lines.

In order to determine the possible reasons for the discordance of protein and activity levels in some lines, all of the data was compiled into the graphs shown in FIGS. 5A and 5B. FIG. 5A shows the relative amounts of cdk2, cyclin D1, cyclin D3 and cdk6 proteins and of cdk6 kinase activity in HMECs compared to the amounts in the MCF-7, BT-20, BT-474, MDA-MB-468 and MDA-MB-157 cell lines. FIG. 5B shows the relative amounts of cdk2, cyclin D1, cyclin D3 and cdk6 proteins and of cdk6 kinase activity in HMECs compared to the amounts in the BT-549, MDA-MB-453, T-47D, ZR-75-1 and MDA-MB-134-VI* cell lines. The scale of measurement of relative protein or activity contents is as described in Tables 1 and 2, with 0 being equivalent to "–" and increasing to 4, or "++++." Bars representing the "0," "–" or "+/–" amounts are shown slightly raised above the x-axis (in FIGS. 5A and 5B, the names of the MDA-MB-468, 157, 453 and 134-VI* cell lines are shortened to MDA-468, 157, 453 and 134-VI*, respectively). As shown in FIGS. 5A and 5B, all lines with little or no detectable cdk6 protein (MDA-MB 453 and 134-VI*, T-47D and ZR-75-1) had little cdk6 enzyme activity, despite their levels of cyclin D proteins. Two of the lines with low cdk6 protein levels but very high activity levels (MCF-7 and BT-474) were found to have elevated levels of both cyclin D1 and cyclin D3. Thus, these lines may have compensated for low cdk6 protein levels by elevating cyclin D amounts. The third line with relatively high activity but low cdk6 protein (BT-20) had a relatively normal level of D-type cyclins. Cells with relatively high cdk6 protein levels (HMECs, MDA-MB-468 and 157, BT-549) had high activity levels. MDA-MB-468 and MDA-MB-157 levels may even have been enhanced by overproduction of the cyclins.

In summary, in all of the breast-tumor derived cell lines investigated, the cell lines had reduced levels of cdk6 protein. In some case, it appeared that normal levels of enzyme activity were restored by elevations in cyclin D contents. In other cases, almost no cdk6 protein was seen. It was of interest that examination of the cell lines suggested that those with highest cdk6 protein content most resembled the normal HMECs in morphology and growth properties (data not shown).

The following Materials and Methods were used in the experiments described in Examples 11–13.

Cell preparation and culture. Peripheral blood T cells were isolated from healthy volunteers. Mononuclear cell suspensions were prepared by Ficoll-Hypaque gradient centrifugation and T cells (E+) were obtained by E-rosette enrichment (Kumagai et al., 1987, J. Immunol. 139, 1393–1400). This population contained greater than 95% T cells as determined by immunofluorescence with anti-CD3 (Kumagai et al., 1987, ibid.). Cells were cultured in RPMI medium containing 10% (v/v) fetal calf serum and 2 mM glutamine. T cells were activated by the addition of phytohemraglutinin (PHA) at a concentration of 10 μg/ml (Kumagai et al., 1987, ibid.).

Immunoblot Analysis. Cells (4×10⁶) were incubated in the presence or absence of PHA as indicated in the text. Immunoblot analysis was performed essentially as described previously (Melamed et al., 1992, J. Immunol. 149, 169–174; Lucas et al., 1995, J. Cell. Physiol., 165,406–416; Lucas et al., 1996, J. Immunol. 154,6275–6284). Briefly, cells were quickly pelleted and then lysed in 5×SDS-gel sample buffer, followed immediately by boiling for 5 min. Lysates were frozen, thawed, centrifuged at 12,000×g for 5 min, and supernatants analyzed by SDS-PAGE. The separated proteins were electrophoretically transferred to nitrocellulose or Immobilon® (Millipore), and the unreacted sites on the membranes were blocked overnight with 5% BSA (essentially fatty acid and globulin-free BSA, Calbiochem, San Diego, Calif.) in 10 mM Tris, 150 mM NaCl, and 0.01% NaN$_3$, pH 8.0 (blocking solution). The blot was then incubated with the specific antibody in 4 ml of blocking solution. Anti-cdk6 (a rabbit polyclonal) and anti-Fyn (a mouse monoclonal) were obtained from Santa Cruz Biotechnology (Santa Cruz, Calif.). The blot was then washed twice for 10 min in blocking solution. This was followed by a 10 min wash with blocking solution containing 0.5% Nonidet P-40 and twice more with blocking buffer. Specific bands were detected by the chemiluminescent method, as described previously (Lucas et al., 1995, ibid.; Lucas et al., 1996, ibid.).

Immunoprecipitation. Cells ($2\times10^7$) were washed with PBS and resuspended in lysis buffer containing 20 mM HEPES (pH 7.4), 125 mM NaCl, 1% Triton® X-100, 10 mM EDTA, 2 mM EGTA, 2 mM Na$_3$VO$_4$, 50 mM sodium fluoride, 20 mM ZnCl$_2$, 10 mM sodium pyrophosphate, 1 mM PMSF, and 5 µg/ml leupeptin (Melamed et al., 1992, ibid.; Lucas et al., 1995, ibid.). After cell lysis, the samples were centrifuged for 15 min at 12,000×g to remove cellular debris. After preclearing lysates with recombinant protein G-coupled Sepharose® beads (Zymed, San Francisco, Calif.), specific immune complexes were precipitated with the indicated antibodies. The Sepharose® beads containing the immunoprecipitates were washed 3 times with washing buffer (lysis buffer without PMSF and leupeptin), once with 0.5 M LiCl, 0.1 M Tris hydrochloride (pH 7.5) and once with 0.1 m NaCl, 1 mM EDTA, 2 mM Tris hydrochloride, pH 7.5. SDS-sample buffer was added to the washed immunoprecipitates and the samples were electrophoretically separated on a 10% SDS-polyacrylamide gel.

Co-immunoprecipitation. Interactions between two molecules were examined using a sensitive method of co-immunoprecipitation, modified from the procedure described previously (Pleiman et al., 1993, *Mol. Cell. Biol.*, 13, 5877–5887). T cells ($20\times10^6$) were stimulated for the indicated times with PHA. The cells were than lysed in 1% NP-40 lysis buffer, clarified, and then precleared with pro-tein A-Sepharose® beads for 4 hours at 4° C. Anti-cdk6 was added and allowed to bind for 2 hours at 4° C. Immune complexes were then precipitated by adding protein A-Sepharose® CL4B beads (Pharmacia, Uppsala, Sweden). The beads were washed three times in lysis buffer and twice in an in vitro kinase assay buffer (150 nM NaCl, 10 nM HEPES, 1 mM phenylmethylsulfonylfluoride, and 2 mM sodium orthovanadate) resuspended in 20 µl of kinase buffer, and then incubated for 15 minutes at 30° C. in the presence of 10 MCI of γ-$^{32}$P-ATP. Beads were than washed twice in lysis buffer to remove free ATP and boiled in 1 volume of 20 mM Tris-HCl (pH 8.0) containing 0.5% SDS and 1 mM dithiothreitol to disrupt protein-protein interactions. Secondary immunoprecipitation was performed by adding anti-Fyn and protein A beads to samples after diluting the SDS to 0.1% with 4 volumes of lysis buffer. Beads were then washed in lysis buffer and boiled in sample buffer. Samples were divided into two parts and proteins were resolved in two duplicate SDS-10% polyacrylamide gels. One gel was dried and radio labeled proteins were detected by autoradiography. The other gel was subjected to immunoblot analysis for cdk6 and Fyn. That is, after electrophoretic transfer to a membrane, proteins were detected using a mixture of anti-cdk6 and anti-Fyn, followed by incubation with two secondary antibodies directed against the mouse monoclonal and rabbit polyclonal primary antibodies. Specific bands were detected by chemiluminescence, as described above. Exposure times for the chemiluminescence (<1 min) were not sufficient to detect the radio labeled material.

Determination of cdk kinase activity. Assays for cdk2 or cdk6 were performed as described in Examples 1–3. After washing, immunoprecipitates were then suspended in a kinase reaction buffer containing 100 mM ATP, 20 µCi of γ-$^{32}$P-ATP and 1 µg of recombinant Fyn protein in a final volume of 25 µl and incubated at 30° C. for 30 min. The Fyn proteins used as substrates were the GST-fusion proteins described previously (Pleiman et al., 1993, supra). The protein referred to as Fyn contained amino acids 1 through 255 but lacked the carboxyl half of the enzyme containing the kinase domain. The protein referred to as Δ Fyn contained amino acids 1 through 144 and hence also lacked the SH2 domain of the Fyn protein. The fusion proteins migrated in 10% polyacrylamide gels with apparent molecular masses of 60 and 42 kDa, respectively. Reactions were stopped by addition of the SDS-containing sample buffer. After heating at 95° C. for 5 min and then cooling, the protein G immunobeads were pelleted by centrifugation and proteins in the reaction mixture were resolved by 10% PAGE. The Fyn bands were visualized by a brief staining of the gels with Coomasie Blue (R-250) in fixative (7% acetic acid/40% methanol/50% water). The gels were then dried and the labeled bands were detected by autoradiography.

Digital immunofluorescence microscopy. The techniques used were similar to those described in detail previously (Kupfer et al., 1991, *Proc. Natl. Acad. Sci. U.S.A.* 88, 775–779; Kupfer et al., 1994, *J. Exp. Med.* 179, 1507–1515; Nagasawa et al., 1997, *J. Immunol.* 158, 5146–5154). Cell samples ($2\times10^5$) were removed from the culture, placed on glass coverslips that had been treated with poly-D-lysine, and fixed with freshly prepared 3% paraformaldehyde. The cells were treated with 0.2% Triton-100 to enable intracellular labeling, than incubated with primary antibodies, that is, rabbit polyclonal anti-cdk-6 and/or mouse monoclonal anti-Fyn or rabbit polyclonal anti-cdk4 or anti-cdk2. All antibodies(Santa Cruz Biotechnology) were used at a concentration of 10 µg/ml. After extensive washing, samples were labeled with Cy-3 tagged donkey anti-rabbit and/or anti-mouse IgG at a concentration of 5 µg/ml. The specificity of the primary antibodies used was demonstrated by immunoprecipitation and immunoblotting experiments as described previously (Modiano et al., 1994, *J. Biol. Chem.*, 269, 32972–32978; Lucas et al., 1995, *Blood*, 86, 2268–2280; Lucas et al., 1995, supra; Lucas et al., 1996, sulpra). Furthermore, the specific immunofluorescence patterns seen here were not observed if the primary antibody was first incubated with the peptide against which the antibody was raised. The immunofluorescence and corresponding Nomarski images were recorded by a chilled coupled device digital camera (SensiCam, Cooke Inst.) that was mounted on a Zeiss Axiophot® microscope, equipped with narrow band optical filters (Chormatech). Images were captured using Slidebook software (Intelligent Imaging Innovations, Inc.). Out-of-focus haze was removed from the images using the no-neighbor deconvolution module of Slidebook.

Example 11

The following example demonstrates the co-localization of cdk6 and Fyn early after T-cell activation.

Fyn plays a key role in early activation events in T lymphocytes (Howe and Weiss, 1995, *Trends Biochem. Sci.*, 20, 59–64; Qian and Weiss, 1997, *Curr. Opin. Cell Biol.*, 9,205–212). In order to examine a possible role for cdk6 in such early events, the intracellular localization of cdk6 and Fyn were compared during stimulation of resting T cells using digital immunofluorescence microscopy. In these experiments, human peripheral blood T cells were stimulated with PHA, and at various times were examined for the presence and localization of both cdk6 and Fyn. Briefly, purified, resting T-cells were isolated and activated with PHA. At 0, 10, 30 and 60 minutes and at 24 hrs after activation, cells were isolated and prepared for digital immunofluorescence microscopy. Fyn and cdk6 proteins were detected using specific antibodies as described in Materials and Methods. The results (data not shown) demonstrated that, in resting T cells, both proteins are present throughout the entire cytoplasm. By 10 minutes after T-cell activation, the two proteins co-localize in a sharp ring along the plasma membrane. The same pattern is also seen at 30 minutes. At both of these time points, an obvious co-localization of cdk6 and Fyn is seen at the plasma membrane. By 60 minutes after activation this membrane co-localization is no longer seen. Most cdk6 has translocated to the nucleus and while some Fyn labeling also appears to be nuclear, most of this kinase remains in the cytoplasm. By 24 hours, little co-localization is observed, indicating that cdk6 and Fyn are now largely in different cellular compartments.

Next, immunofluorescence localization of the cdk4 and cdk6 proteins in resting and activated human T cells was investigated. Briefly, purified resting T cells were isolated and activated with PHA. At 60 minutes after activation, cells were isolated and prepared for digital immunofluorescence microscopy. The cdk4 and cdk6 proteins were detected using specific antibodies as described in Materials and Methods. The results demonstrated that Cdk4, which is activated in T cells several hours after cdk6, is also present in resting T-cells (data not shown). Even at 60 min after PHA-stimulation, its localization remains unchanged. Immunofluorescence localization of the cdk2 protein in resting and activated human T cells was also investigated. Similarly, cdk2, another cdk present in resting T cells, remains localized in the cytoplasm for several hours after T cell stimulation (data not shown). Only at later times in the G1-phase, cdk4, and then cdk2, also migrate to the cell nucleus (data not shown). In summary, both cdk6 and Fyn, present in the cytoplasm of resting cells, become enriched and co-localized at the cell periphery within minutes of T-cell activation. However, this co-localization is transient and by 60 minutes, most cdk6 is translocated to the nucleus whereas Fyn remains primarily in the cytoplasm.

Example 12

The following example demonstrates the physical association of cdk6 and Fyn after T-cell activation.

The possible interaction of cdk6 and Fyn was examined in co-immunoprecipitation experiments. In these experiments, cdk6 was immunoprecipitated under gentle conditions from resting and activated T cells. An in vitro kinase assay was performed and then Fyn was immunoprecipitated from the reaction mixture. Briefly, resting human T cells were activated with PHA and harvested at 0, 10, 30 and 60 minutes after activation. Cdk6 was prepared by immunoprecipitation; an in vitro kinase assay was performed and then Fyn was isolated from the reaction mixtures by immunoprecipitation. Samples were divided into two parts and proteins were resolved in two duplicate polyacrylamide gels. One gel was dried and radio labeled bands were detected by autoradiography. The second gel was used for immunoblot analysis. Proteins with the molecular masses of the cdk6 and Fyn kinases were observed after gel electrophoresis and autoradiography. The level of phosphorylation of the two proteins increased after activation, reaching a maximal level by 10 to 30 minutes, followed by a decline. Whether or not the two kinases became labeled by mutually phosphorylating each other, by autophosphorylation, or by a third kinase present in the immunoprecipitates cannot be distinguished by this technique. The presence of cdk6 and Fyn was confirmed by immunoblot analysis of a duplicate gel using the chemiluminesence technique. Briefly, proteins were electrophoretically transferred to a membrane and specific bands were detected by the chemiluminescent method, using a mixture of primary antibodies to the cdk6 and Fyn proteins. The association of the two kinases appeared to be very strong, as indicated by the fact that the complex of cdk6 and Fyn was present throughout the experimental procedure, which included conditions which would disrupt many protein/protein interactions.

In an additional experiment, the possible associations of cdk6 with Fyn and Lck, another Src-family kinase present in T cells were compared. Briefly, T cells were stimulated with PHA for 10 minutes. Resting and stimulated cells were harvested, extracts were prepared, and either Lck or Fyn was immunoprecipitated. After in vitro kinase assays were performed, cdk6 was immunoprecipitated from the reaction mixtures. The samples were subjected to gel electrophoresis, and proteins were detected by autoradiography. A radiolabeled protein with the electrophoretic mobility of cdk6 was found to be co-immunoprecipitated with Fyn but not Lck (data not shown).

Example 13

The following example demonstrates the phosphorylation of Fyn by cdk6.

Phosphorylation of Fyn after co-immunoprecipitation suggested that it could be a substrate for cdk6. Although the primary mode of regulation of Fyn activity is through tyrosine phosphorylation (Courtneidge et al., 1993, *Develop. Suppl.* pp. 57–64; Davidson et al., 1994, *J. Biol. Chem.* 269, 10956–10963), the kinase is also known to have several potential serine and threonine phosphorylation sites, which may play secondary roles in the regulation of Fyn activity (Peters et al., 1990, *Oncogene*, 5, 1313–1319; Cheng et al., 1991, *J. Virol.*, 65, 170–179). Therefore, the ability of cdk6 to phosphorylate Fyn-derived proteins in vitro was assessed. In these experiments, cdk6 was prepared from resting or activated T-cells and examined for its ability to phosphorylate Fyn in vitro. Briefly, resting T cells were activated by PHA and cells were harvested at 0, 10, 30 and 60 minutes after stimulation. Cdk6 and cdk2 were immunoprecipitated and used in vitro kinase assays. First, cdk6 was assayed with a Fyn substrate which was a GST-Fyn fusion protein containing amino acid residues 1 through 255 of Fyn results demonstrated that cdk6 could effectively phosphorylate a Fyn protein which contained amino acid residues 1 through 255 fused to GST (labeled as Fyn). This recombinant Fyn protein, which migrates as a protein of 60 kDa, lacks the carboxyl half of the protein containing the kinase domain, but it contains the SH3 and SH2 domains of Fyn (Pleiman et al., 1993, supra). Since it lacks the kinase domain of Fyn the observed phosphorylation of the protein could not be due to autophosphorylation. Most activity was present from 10 to 30 minutes after T-cell activation, and then declined. Since the cdk6 protein increases in amount throughout most of the G1-phase, this result suggests that the cdk6 present after 30 min is not in a form which can optimally phosphorylate Fyn.

When the substrate Δ Fyn, which migrates in gels as a 42 kDa protein, was used in the kinase reactions, no phosphorylation of the protein was observed (data not shown). In this experiment, cdk6 was assayed with the Δ Fyn substrate, which was a GST-Fyn fusion protein containing amino acid residues 1 through 144 of Fyn. The Δ Fyn protein lacks not only the kinase domain but also the SH2 region of Fyn. The lack of phosphorylation of Δ Fyn indicates that the phosphorylation of the 60 kDa protein occurred in the SH2 domain of Fyn. Also of importance, the differential phosphorylation of the 60 kDa and 42kDa proteins indicates that the phosphorylation observed did not occur in the GST portion of the molecule, as this is shared by both recombinant proteins. Furthermore, cdk2 immunoprecipitates failed to phosphorylate the 60kDa Fyn fusion protein (data not shown). Together, these studies indicate that cdk6 and Fyn associate with each other early after T-cell activation and that the Fyn tyrosine kinase may be a substrate for cdk6.

In summary, it is proposed that cdk6 is involved in the regulation of Fyn activity, through serine/threonine phosphorylation, during T-cell activation. As described above, Fyn can be phosphorylated in co-immunoprecipitates of Fyn and cdk6. Although some of the phosphorylation sites may reside in the carboxyl-, kinase domain-containing region of the enzyme, the results presented herein clearly indicate that the SH2 domain of Fyn contains one or more cdk6 phosphorylation sites. This is of interest as it suggests the possibility that cdk6 may be regulating the ability of the tyrosine kinase to bind to other proteins, rather than, or in addition to, regulating its enzymatic activity. The SH2 domain of Fyn contains 12 serine/threonine residues. These data indicate the possibility that cdk6, expressed in the resting T-cell, plays a role in regulating the activity of Fyn through phosphorylation of serine/threonine residues. Alternatively, or additionally, cdk6 may play a role in transducing the signals initiated with tyrosine kinase activation.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims.

What is claimed is:

1. A method for diagnosing breast cancer in a patient, comprising:
   a) detecting the level of cdk6 expression in a breast tissue cell sample from a patient to be diagnosed;
   b) detecting the level of cdk6 expression in a normal control breast tissue cell sample;
   c) comparing the level of cdk6 expression detected in step (a) to the level of cdk6 expression detected in step (b); and
   d) determining a difference between the levels of cdk6 expression;
   wherein a determination of a reduced level of cdk6 expression in the breast tissue cell sample from a patient to be diagnosed, as compared to the level of cdk6 expression in the normal control breast tissue cell sample, is indicative of a positive diagnosis of breast cancer in the patient; and,
   wherein a determination of an increased or a substantially similar level of cdk6 expression in the breast tissue cell sample from a patient to be diagnosed, as compared to the level of cdk6 expression in the normal control breast tissue cell sample, is indicative of a negative diagnosis of breast cancer in the patient.

2. The method of claim 1, wherein said step (a) and step (b) of detecting comprise detecting cdk6 mRNA transcription in said cell sample.

3. The method of claim 2, wherein said step (a) and step (b) of detecting is are by a method selected from the group consisting of polymerase chain reaction (PCR), reverse transcriptase-PCR (RT-PCR), in situ hybridization, Northern blot, sequence analysis and detection of a reporter gene.

4. The method of claim 1, wherein said step (a) and step (b) of detecting comprise detecting cdk6 translation in said cell sample.

5. The method of claim 4, wherein said step (a) and step (b) of detecting are by a method selected from the group consisting of immunoblot, enzyme-linked immunosorbant assay (ELISA), radioimmunoassay (RIA), immunoprecipitation, immunohistochemistry and immunofluorescence.

6. The method of claim 1, wherein said cell sample in step (a) and step (b) is from a mammary epithelial cell.

7. The method of claim 1, wherein a determination of a statistically significant reduction in the level of cdk6 expression in said patient cell sample as compared to the level of cdk6 expression in said normal control cell sample, with a confidence of $p<0.05$, indicates a positive diagnosis of breast cancer in said patient.

8. The method of claim 1, wherein a determination of an at least about 30% reduction in the level of cdk6 expression in said patient cell sample as compared to the level of cdk6 expression in said normal control cell sample, with a confidence of $p<0.05$, indicates a positive diagnosis of breast cancer in said patient.

9. The method of claim 1, wherein a determination of an at least about 50% reduction in the level of cdk6 expression in said patient cell sample as compared to the level of cdk6 expression in said normal control cell sample, with a confidence of $p<0.05$, indicates a positive diagnosis of breast cancer in said patient.

10. The method of claim 1, wherein a determination of an at least about 1.5 fold reduction in the level of cdk6 expression in said patient cell sample as compared to the level of cdk6 expression in said normal control cell sample, with a confidence of $p<0.05$, indicates a positive diagnosis of breast cancer in said patient.

11. The method of claim 1, wherein, when said level of cdk6 expression detected in step (a) is reduced as compared to said level of cdk6 expression detected in step (b), said method further comprises:
   c) comparing said level of cdk expression as detected in step (a) to levels of cdk6 expression established from a panel of positive tumor control samples, wherein each of said positive tumor control samples is correlated with a different stage of tumor development, and determining a difference between said levels of cdk6 expression; and,
   d) identifying a level of cdk6 expression from one of said positive tumor control samples which is statistically significantly most similar to said level of cdk6 expression detected in step (a), to diagnose a stage of tumor development in said patient.

12. The method of claim 11, wherein said panel of tumor control samples comprises one tumor control sample from each of a stage I, stage II, stage III, and stage IV, breast cell tumor.

13. The method of claim 1, wherein the normal control breast tissue cell sample is selected from the group consisting of:

i) an autologous breast tissue sample from said patient;
ii) a previous breast tissue cell sample from said patient, wherein said previous sample was determined to be negative for breast cancer; and,
iii) a normal breast tissue cell sample from one or more matched individuals.

* * * * *

UNITED STATES PATENT AND TRADEMARK OFFICE
CERTIFICATE OF CORRECTION

PATENT NO. : 7,160,681 B2
APPLICATION NO. : 10/154272
DATED : January 9, 2007
INVENTOR(S) : Gelfand et al.

It is certified that error appears in the above-identified patent and that said Letters Patent is hereby corrected as shown below:

Claim 3:

Column 66, line 7, delete the word "is".

Signed and Sealed this

Tenth Day of April, 2007

JON W. DUDAS
*Director of the United States Patent and Trademark Office*